United States Patent
Bashir et al.

(10) Patent No.: US 11,732,293 B2
(45) Date of Patent: Aug. 22, 2023

(54) BIOMARKER DETECTION FROM FLUID SAMPLES

(71) Applicant: The Board of Trustees of the University of Illinois, Urbana, IL (US)

(72) Inventors: Rashid Bashir, Champaign, IL (US); Anurup Ganguli, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 544 days.

(21) Appl. No.: 16/649,894

(22) PCT Filed: Oct. 5, 2018

(86) PCT No.: PCT/US2018/054634
§ 371 (c)(1),
(2) Date: Mar. 23, 2020

(87) PCT Pub. No.: WO2019/071142
PCT Pub. Date: Apr. 11, 2019

(65) Prior Publication Data
US 2020/0263244 A1 Aug. 20, 2020

Related U.S. Application Data

(60) Provisional application No. 62/569,119, filed on Oct. 6, 2017.

(51) Int. Cl.
| | | |
|---|---|---|
| C12Q 1/68 | (2018.01) | |
| C12Q 1/6848 | (2018.01) | |
| B01L 3/00 | (2006.01) | |
| C12Q 1/6806 | (2018.01) | |
| C12Q 1/6851 | (2018.01) | |
| C12Q 1/689 | (2018.01) | |
| G01N 27/414 | (2006.01) | |
| B03C 1/01 | (2006.01) | |
| B03C 1/28 | (2006.01) | |
| B03C 1/30 | (2006.01) | |

(52) U.S. Cl.
CPC .......... *C12Q 1/6848* (2013.01); *B01L 3/5027* (2013.01); *C12Q 1/6806* (2013.01); *C12Q 1/689* (2013.01); *C12Q 1/6851* (2013.01); *G01N 27/4145* (2013.01); *B01L 2200/0689* (2013.01); *B01L 2300/0861* (2013.01); *B01L 2300/0893* (2013.01); *B01L 2300/161* (2013.01); *B03C 1/01* (2013.01); *B03C 1/288* (2013.01); *B03C 1/30* (2013.01); *B03C 2201/18* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 9,376,713 B2 * | 6/2016 | Bashir | .................... B03C 5/026 |
| 10,175,195 B2 | 1/2019 | Bashir et al. | |
| 10,527,579 B2 | 1/2020 | Bashir et al. | |
| 10,724,089 B2 | 7/2020 | Bashir et al. | |
| 2006/0068398 A1 | 3/2006 | McMillan | |
| 2009/0266713 A1 | 10/2009 | Falk-Jordan et al. | |
| 2012/0270332 A1 | 10/2012 | Wimberger-Friedl et al. | |
| 2016/0253584 A1 | 9/2016 | Fodor et al. | |
| 2017/0022546 A1 | 1/2017 | Bashir et al. | |
| 2017/0114369 A1 | 4/2017 | Donohoue et al. | |
| 2019/0011349 A1 | 1/2019 | Bashir et al. | |
| 2020/0391169 A1 | 12/2020 | Han et al. | |
| 2021/0010079 A1 | 1/2021 | Bashir et al. | |
| 2021/0339244 A1 | 11/2021 | Ganguli et al. | |

FOREIGN PATENT DOCUMENTS

| | | | |
|---|---|---|---|
| WO | WO 2020/190871 A1 | 9/2020 | |
| WO | WO 2021/174068 A1 | 9/2021 | |

OTHER PUBLICATIONS

Navolotskii et al. (Appl Biochem and Microbiol, 2011, vol. 47, No. 2, p. 221-227) (Year: 2011).*
Liu et al. (Sensors, 2009, vol. 9, p. 3713-3744 (Year: 2009).*
Tomazou et al. (Nature Methods, 2013, 10(7):641-648) (Year: 2013).*
Hurley et al. (Jian-Bing Fan (ed.), Next-Generation MicroRNA Expression Profiling Technology: Methods and Protocols, Methods in Molecular Biology, vol. 822, 2012, Chapter 3, p. 33-52) (Year: 2012).*
Zetsche et al. (2016, bioRxiv 049122; doi: doi.org/10.1101/049122, later published as Nature Biotechnology, 2017, 35, p. 31-34) (Year: 2017).*
Jokerst et al. (Small, 2011, 7(5):613-624) (Year: 2011).*
Akhmetov, I. & Bubnov, R. V. Assessing value of innovative molecular diagnostic tests in the concept of predictive, preventive, and personalized medicine. *Epma J.* 6, 19 (2015).
Arrayit Microarray Printing Pins and Printheads—Professional 946 Stealth ChipMakerTM Spotting Gene Chips Bead Array Manufacturing. Available at: http://www.arrayit.com/Products/Microarray_Printing/microarray_printing. html(Accessed: Apr. 30, 2017).
Bain, B. J. Diagnosis from the Blood Smear. N. Engl. J. Med. 353, 498-507 (2005).

(Continued)

*Primary Examiner* — Stephanie K Mummert
(74) *Attorney, Agent, or Firm* — Leydig, Voit & Mayer, Ltd.

(57) ABSTRACT

Described herein are systems and methods which utilize an array of wells to isolate pathogens and nucleic acid detection techniques to accurately and rapidly detect pathogens in fluid samples, even in very low concentrations, including from solid or semi-solid samples that have been fluidized. The provided systems and methods dry the fluid sample to deposit a fraction of the total volume in a number of wells and perform nucleic acid detection on individual wells to detect even individual pathogens and provide a quantitative analysis of the amount of pathogen within the sample. Also provided are methods and systems for precise delivery of dried materials, including biomolecules that are enzymes of use in the process, to microwells.

40 Claims, 29 Drawing Sheets

(56) References Cited

OTHER PUBLICATIONS

Barker, R. H. et al. A simple method to detect Plasmodium falciparum directly from blood samples using the polymerase chain reaction. Am. J. Trap. Med. Hyg. 46, 416-426 (1992).
Brambilla, D. et al. Multicenter Evaluation of Use of Dried Blood and Plasma Spot Specimens in Quantitative Assays for Human Immunodeficiency Virus RNA : Measurement , Precision , and RNA Stability Multicenter Evaluation of Use of Dried Blood and Plasma Spot Specimens in Quan. J. Clin. Microbiol. 41, 1888-1898 (2003).
Brittain-Long, R. et al. Multiplex real-time PCR for detection of respiratory tract infections. J. Clin. Virol. 41, 53-56 (2008).
C. Schrader, A. Schielke, L. Ellerbroek and R. Johne, PCR inhibitors—occurrence, properties and removal, Journal of Applied Microbiology 113, 1014-1026, 2012.
Cepheid | GeneXpert IV. Available at: http://www.cepheid.com/us/cepheid-solutions/systems/genexpertsystems/genexpert-iv. (Accessed: Apr. 30, 2017).
Curtis, K., Rudolph, D., Nejad, I. & Singleton, J. Isothermal amplification using a chemical heating device for point-of-care detection of HIV-1. PLoS One (2012).
Damhorst, G. L. et al. Smartphone-Imaged HIV-1 Reverse-Transcription Loop-Mediated Isothermal Amplification (RT-LAMP) on a Chip from Whole Blood. Eng. (Beijing, China) 1, 324-335 (2015).
De Bruin et al. "A Method for Assessing Efficiency of Bacterial Cell Disruption and DNA Release" BMC Microbiol., 16(197): 1-10 (2016).
Duarte-Guevara, C. et al. On-chip electrical detection of parallel loop-mediated isothermal amplification with DG-BioFETs for the detection of foodborne bacterial pathogens. RSC Adv. 6, 103872-103887 (2016).
Fauci, A. S. & Morens, D. M. The Perpetual Challenge of Infectious Diseases. *N. Engl. J. Med.* 366, 454-461 (2012).
Ganguli et al. "Hands-free smartphone based diagnostics for simultaneous detection of Zika, Chikungunya, and Dengue at point-of-care." Biomed Microdevices, 2017. 19(4) pp. 1-13.
Ganguli et al. "Spatially Mapped Gene Expression Analysis from Tissue," University of Illinois at Urbana-Champaign, 2016 pp. 1-40.
Ganguli, A., Ornob, A., Spegazzini, N. et al. Pixelated spatial gene expression analysis from tissue. Nat Commun 9, 202 (2018).
Gole et al. "Massively parallel polymerase cloning and genome sequencing of single cells using nanoliter microwells" Nature Biotechnology 31, pp. 1126-1132 (2013).
Grün et al. "Design and Analysis of Single-Cell Sequencing Experiments." Cell 163(4): 799-810 (2015).
Gunson, R., Collins, T. & Carman, W. Real-time RT-PCR detection of 12 respiratory viral infections in four triplex reactions. J. Clin. Virol. (2005).
Hashimshony et al. "CEL-Seq: Single-Cell RNA-Seq by Multiplexed Linear Amplification." Cell Reports 2(3): 666-673 (2012).
International Preliminary Report on Patentability dated Apr. 16, 2020 in PCT/US2018/054634.
Islam, et al. "A Review on Macroscale and Microscale Cell Lysis Methods" Micromachines, Mar. 2017, 8, 83 pp. 1-27.
Jaitin et al. "Massively parallel single cell RNA-Seq for marker-free decomposition of tissues into cell types." Science 343(6172): 776-779 (2014).
Lawn, S. D. et al. Advances in tuberculosis diagnostics: The Xpert MTB/RIF assay and future prospects for a point-of-care test. Lancet Infect. Dis. 13, 349-361 (2013).
Lone Rossen, Pernille Norskov, Kim Hoimstrom and Ole F. Rasmussen, Inhibition of PCR by components of food samples, microbial diagnostic assays and DNA-extraction solutions, International Journal of Food microbiology, 17 (1992) 37-45.
Loonen et al. "Comparison of Pathogen DNA Isolation Methods from Large Volumes of Whole Blood to Improve Molecular Diagnosis of Bloodstream Infections", PLoS One, 2013, 8, 1-7.
Lundborg, C., Mölstad, S. & Olsson, E. Antibiotic prescribing in outpatients: a 1-week diagnosis-prescribing study in 5 counties in Sweden. Scand. J. (2002).
Mabey, D., Peeling, R. W., Ustianowski, A. & Perkins, M. D. Diagnostics for the developing world. Nat. Rev. Microbiol. 2, 231-240 (2004).
Mancini "The Era of Molecular and Other Non-Culture Based Methods in Diagnosis of Sepsis" Clin. Microbiol. 23(1): 235-251 (2010).
Martin et al., "National Health Spending in 2014: Faster Growth Driven by Coverage Expansion and Prescription Drug Spending" Health Aff., 2016, 35, 150-160.
May et al. A Flash Storage Technical and Economic Primer. ActualTech Media (2015).
McNerney, R. & Daley, P. Towards a point-of-care test for active tuberculosis: obstacles and opportunities. Nat. Rev. Microbiol. 9, 204-213 (2011).
Micron Technology, Inc.—3D XPointTM Technology. Available at: https://www.micron.com/about/ourinnovation/3d-xpoint-technology. (Accessed: Apr. 30, 2017).
Notomi, T. et al. Loop-mediated isothermal amplification of DNA. 28, (2000).
Oh et al. "Application of Bio-Cell Chip Technology to Rapid Genomic DNA Preparation and PCR Amplification." Blood 2009, 114:4197.
Owano, Nancy. "Taiwan engineers defeat limits of flash memory." phys.org (2012).
Packard, et al. "Performance Evaluation of Fast Microfluidic Thermal Lysis of Bacteria for Diagnostic Sample Preparation" Diagnostics 2013, 3, 105-116.
Perner et al. "Sepsis: frontiers in diagnosis, resuscitation and antibiotic therapy" Intensive care (2016) 42:1958-1969.
Peters et al. "New Developments in the Diagnosis of Bloodstream Infections" Lancet Infect. Dis., 2004, 4, 751-760.
Picelli et al. "Full-length RNA-seq from single cells using Smart-seq2" Nat Protoc. Jan. 2014;9(1):171-81.
Priye, A. et al. A smartphone-based diagnostic platform for rapid detection of Zika, chikungunya, and dengue viruses. Sci. Rep. 7, 44778 (Mar. 2017).
Rosenberg et al. "Single-cell profiling of the developing mouse brain and spinal cord with split-pool barcoding." Science 360(6385), 176-182 (Apr. 2018).
Song, J. et al. Instrument-Free Point-of-Care Molecular Detection of Zika Virus. Anal. Chem. 88, 7289-7294 (2016).
Stahl et al. "Visualization and analysis of gene expression in tissue sections by spatial transcriptomics." Science 353(6294), 78-82 (2016).
Taylor et al. "Real-time PCR detection of Plasmodium directly from whole blood and filter paper samples" Malaria Journal 10:244 (2011) 8pp.
Toumazou, C. et al. Simultaneous DNA amplification and detection using a pH-sensing semiconductor system. Nat. Methods 10, 641-6 (2013).
Vincent et al. "Sepsis definitions: time for change" Lancet 381(9868): 774-775 (2013).
Wang et al. "Current Trends in Detecting Non-O157 Shiga Toxin-Producing *Escherichia coli* in Food" Foodborne Pathogens and Disease, 2013. 10(8):1-13.
WHO | A WHO external quality assurance scheme for malaria nucleic acid amplification testing. Meeting report. WHO (2016).
WHO | Global tuberculosis report 2016. WHO (2017).
Wu et al. "Single-Cell Transcriptional Analysis." Annual Review of Analytical Chemistry 10: 439-462 (Mar. 2017).

* cited by examiner

Large clumps of beads observed

Beads encapsulated in a ring of oil in the primary water phase

Smaller clumps – better mixing

Beads in a single phase after centrifugation

Very little clumping observed after mixing

Beads in a single phase after centrifugation

BIOMARKER DETECTION FROM FLUID SAMPLES

CROSS-REFERENCE TO RELATED APPLICATIONS

This application is a U.S. National Stage Application under 35 U.S.C. § 371 of International Application No. PCT/US2018/054634, filed Oct. 5, 2018, which claims the benefit of priority to U.S. Pat. App. 62/569,119 filed Oct. 6, 2018, which is hereby incorporated by reference to the extent not inconsistent herewith.

STATEMENT REGARDING FEDERALLY SPONSORED RESEARCH OR DEVELOPMENT

This invention was made, at least in part, with United States governmental support awarded by National Science Foundation award no. SBC 5710003967, United States Department of Agriculture award nos. 8000063044, 80000069085 and 8000074077 and National Institutes of Health award no. MGH-APF 087126. The United States Government has certain rights in this invention.

BACKGROUND OF INVENTION

Detection of low concentration pathogens is important in many applications, including food samples, environmental samples and patient samples, including blood, saliva and urine, remains a challenge for medical diagnostic professionals. Many diagnostic techniques common today are methods which have been utilized for decades with minimal improvements in efficacy and efficiency. Currently, many diagnostic tests rely on cell cultures, microscopy or immunoassays which are lacking in sensitivity, costly and time consuming. Additionally, many common testing techniques are directed to single pathogens or conditions, requiring multiple tests to make a diagnosis. These constraints often force pathologists to rely on experience and guesswork, sometimes resulting in misdiagnoses or the overreliance on antibiotics when they may not actually be necessary, which in turn contributes to drug resistance.

For example, diagnosis of sepsis, a bacterial infection of the blood resulting from dysregulated inflammatory response, remains a challenge for medical professionals to quickly diagnosis. The most common test for sepsis is a blood culture followed by nucleic acid amplification, which requires days to a week for a bacteria to grow to detectable quantities and has a high false negative rate. The time required for testing is problematic, as within days of the onset of infection a patient may progress into advance stages leading to organ failure, causing sepsis to have high morbidity and mortality rates. As a result, sepsis remains one of the highest cost patient diagnoses.

Even as technology surrounding nucleic acid amplification techniques have advanced, significant hurdles remain in rapid, low cost identification of pathogens in bodily fluids. While tests have been developed for mRNA biomarkers and pathogen nucleic acids, current RNA/DNA based techniques often require expensive equipment and are directed towards single pathogens, as multiplexing increases costs. The nucleic acid tests also often require costly and time consuming purification steps before the sample may be analyzed. For detection of low concentrations of pathogens, nucleic acid testing is often preceded by a bacterial culture, requiring days to a week of culture time, thereby significantly increasing runtime.

As can be seen from the foregoing, there remains a need in the art for sensitive, rapid diagnostic tests based on nucleic acid detection, including by amplification, that are sufficiently sensitive to detect pathogens in very low concentrations within fluid samples within hours or less. Further, multiplexed testing techniques, which can accurately detect a panel of potential pathogens directly from the sample, are desirable.

SUMMARY OF THE INVENTION

Described herein are systems and methods which utilize an array of wells to isolate pathogens directly from fluid, including liquefied solid samples, body fluids, food samples, environmental samples, with nucleic acid detection, including amplification techniques, to accurately and rapidly detect target analytes, such as pathogens or cell-indicating markers, in fluid samples, even in very low concentrations. The provided systems and methods dry the fluid sample, including a solid or semi-solid sample that has been liquefied, to deposit the total volume or a fraction of the volume in a number of wells and perform nucleic acid detection, such as by amplification, on each of the individual wells to detect the presence of even a single individual target analyte and provide a quantitative analysis of the amount of target analyte within the sample. The systems and methods are robust, and ensure that reagents required for detection, such as amplification or crispr enzyme, reach each individual well, and that reliable detection occurs, even approaching a single target analyte in a well. The technique is compatible with various bodily fluids, including blood, urine, saliva, sputum, etc. Similarly, the technique is compatible with solid and/or semi-solid samples that have been liquefied, including tissue, stool, food, environmental, and the like.

The described systems and methods may also be applied to water, liquid food, and solid food samples that is liquefied to a slurry-like paste or liquid. Testing of food samples to detect pathogens directly without nucleic acid amplification provides numerous benefits and has been seen as a holy grail in the food testing industry.

The systems and methods provided herein facilitate rapid and efficient detection of multiple target analytes. For example, a plurality of nucleic acid sequences or pathogen biomarkers may be capable of being detected for a run-time that is less than or equal to 45 minutes, greatly reducing the time required for an accurate diagnosis and allowing for treatment to occur much more quickly when compared to conventional testing techniques. Further, the provided techniques are multiplexible and facilitate detection of multiple pathogens with a single assay, reducing costs and leading to more accurate diagnoses.

Provided are methods of detecting one or more target analytes from a liquid sample, the method comprising the steps of: applying a liquid sample to a substrate, wherein the substrate has an array of wells; drying the liquid sample to generate a plurality of dried sample islands, with each sample island confined to a unique well; applying a reagent to each well, wherein the reagent is used for nucleic acid detection; eluting a nucleic acid from the dried sample islands with a liquid phase having the applied reagent; detecting a target nucleic acid if present in a dried sample island by a bi-phasic reaction, wherein the detecting is by electrical or optical detection; thereby detecting the one or more target analytes from the liquid biological sample.

"Eluting" is used broadly to refer to the ability of a material (e.g., nucleic acid) in a solid sample to contact liquid (e.g., reagent in the liquid). In the context of a dried sample, eluted nucleic acid refers to lysis of cells to expose nucleic acid to the liquid, including by thermal, chemicals or enzymes, or any technique that can reliably release nucleic acid from the sample. The eluted nucleic acid may continue to reside within the boundaries formed by the outer surface of the dried sample, such as be liquid that has penetrated the dried sample. The eluted nucleic acid may diffuse into the bulk liquid phase, referred herein as "supernatant", that surrounds the dried sample.

The reagent is used for the detecting step, and so may correspond to reagents useful for nucleic acid amplification or may be for a more direct form of detection that does not require amplification, such as by a crispr enzyme. The liquid sample may be dried multiple times, with reagents added between the repeated drying steps. The reagent may be added in the form of a reagent that is provided in a liquid, such as a reagent that is suspended in liquid and that is in intimate contact with the dried sample. The liquid sample may be a crude liquid sample, for example, a liquid sample that has not undergone any processing or purification. In any of the systems and methods described herein, one or more reagents may be introduced into the wells of the array before the liquid sample to be analyzed, after the liquid sample, or some reagents applied before and some after. In any of the described methods, each well of the array may be isolated from other wells, for example, by using one or more barrier layers, such as hydrophobic liquid layers, solid layer barriers and liquid-tight barriers between adjacent wells, thereby limiting or eliminating cross talk between each individual well. The reagents may be specially delivered to the wells, including by reagents released from the barrier layer under a force, such as a centrifugal force.

Any of the methods may further comprise forming microchannels and/or nanochannels in the dried sample islands to facilitate introduction of reagent-containing liquid into an interior portion of the dried sample islands. The eluted nucleic acid may remain in the microchannels and/or nanochannels, may diffuse from the microchannels and/or nanochannels to the liquid phase that is a supernatant to the dried sample islands, may be released directly from the solid to the liquid supernatant, or be a combination thereof. The nano and microchannels may form as part of the drying process, or may be actively induced such as by the use of degradable scaffolds over which the liquid sample is deposited, so that upon drying and degradation, a network of fluidic channels traverse the dried sample. Similarly, beads with reagents connected thereto may be used, so that reagent is introduced into the interior portion of the subsequently dried liquid sample.

Drying and/or eluting (e.g., thermal, chemical, enzymatic) of the sample produces a high surface area to volume ratio, including by producing channel-like structures with passages and/or openings of micro (e.g., less than 1000 μm dimension) and/or nano (e.g., less than 1 μm dimension) scale pores, such as diameters between 0.1 μm and 1000 μm, and any sub-ranges thereof. Such micro and nano vasculature and channels facilitates introduced reagent to access the pathogens and the DNA within the dried sample. Also, when wetted, the high surface area to volume ratio structures with micro and nano vasculature and channels allows for the DNA from the pathogens to escape the blood and access the reagents, such as the polymerase or crispr enzymes, in the supernatant (e.g., bi-phasic reaction). Either way, the combination of drying and introducing the reagents in the appropriate sequence allows for even a single DNA from the pathogen to be detected and/or amplified. Other detection modalities include by crisper enzymes, such as crispr-cpf1.

The impurities and microscale debris/contaminants can be tethered as precipitate or solid phase as a result of drying (not mobile and cannot effectively mix with the reagents) and nanomolecules responsible for reactions (enzymes, dna, and the like) can freely roam around in the liquid phase owing to their small size and high diffusion coefficients in liquid. This allows reactions to proceed smoothly even in the presence of debris from unpurified samples.

In embodiments, the liquid sample is a biological sample. In an embodiment, for example, the liquid sample is minimally processed, including an unprocessed raw sample. Depending on the liquid sample of interest, some minimal processing may be desired. For example, a blood sample may be obtained with an anti-coagulant, to avoid unwanted coagulation. Viscous samples may be diluted with a lower viscosity solvent, thereby facilitating uniform liquid application over the array. For other samples having inherently desired liquid parameters, such as saliva, urine, etc., the obtained bulk sample may be applied directly to the wells. Preferably, the wells have sharp or sloped edges of varying angles so no liquid sample remains outside wells, thereby ensuring more robust capture of liquid containing a target analyte of interest. In an embodiment, the applying the reagent step is before or after the applying the liquid sample step. In an embodiment, the bi-phasic reaction comprises the dried sample island and the reagent suspended in a buffer fluid, wherein the buffer fluid is positioned over the dried sample island in the well.

The method may further comprise a step of forming high surface area structures in the plurality of dried sample islands and/or a reagent liquid positioned over the dried sample islands. The high surface area structures may be formed by mixing gas with the liquid biological sample before or during the drying step. The high surface area structures may comprise a reagent-connected bead suspended in the reagent liquid. The high surface area structures can be formed by degradable micro-nano substrates that will degrade post sample drying and create channels/cavities in the process. In this manner, micro and/or nano-structures may be placed onto the bottom of the well, liquid sample provided thereto that is dried. Upon degradation of the micro and/or nano-structures the remaining dried sample has passages therein.

The provided systems and methods utilize advanced techniques to ensure that enzymes or reagents are provided in each individual well, and thus nucleic acid amplification is performed on each of the dried sample islands. For example, molecules or enzymes may be covalently or non-covalently connected to the surfaces of beads and positioned in each well by various means including gravity or magnetism. This leads to the capability of detecting small concentrations, as small as individual target analytes or pathogens, by ensuring replication on small volume dried sample islands which represent a small fraction of the total volume of the liquid sample.

Any of the methods provided herein may further comprise a bead-based molecule delivery system, wherein the molecule(s) connected to the bead surface is used in the amplifying step. For example, the molecule may be an enzyme, including a polymerase. In an embodiment, the bead-based molecule delivery system comprises a liquid bi-layer application, wherein: a) a buffer mixture covers the dried sample, b) a carrier fluid having the bead-molecule suspended therein is disposed over the buffer mixture, and c) the method further comprising a step of forcing the bead-molecule into the buffer mixture, including settling by gravity or magnetic force for magnetic beads.

In an embodiment, for example, the bead-based molecule delivery system comprises a liquid tri-layer application, wherein: a) a buffer mixture covers the dried sample islands, b) an immiscible separating fluid that covers the buffer mixture, c) a carrier fluid having the bead-molecule suspended therein is disposed over the immiscible separating fluid, wherein the carrier fluid further comprises a surfactant that forms micelles around the bead-molecule to protect the molecule from denaturing, and d) the method further comprising a step of forcing the bead-molecule into the buffer mixture In an embodiment, the bead-based molecule delivery system comprises a liquid layer and frozen liquid layer application, wherein: a) a buffer mixture covers the dried sample islands, b) a carrier fluid having the bead-molecule suspended therein, wherein the carrier fluid has a freezing point less than a freezing point of the buffer mixture, and c) the method further comprising the steps of: i) freezing the buffer mixture by cooling the buffer mixture to a temperature that is below the buffer mixture freezing point and that is above the carrier fluid freezing point, ii) applying the carrier fluid on top of the frozen buffer mixture, iii) forcing the bead-molecule to the frozen buffer mixture-liquid carrier fluid interface, iv) thawing the frozen buffer mixture, and v) forcing the bead-molecule into the buffer mixture.

In embodiments, the high surface area structures comprise a microrelief structure having a molecule connected thereto, the method further comprising the steps of: a) aligning the microrelief structure with the array of wells; b) inserting the microrelief structure into a buffer mixture that occupies the wells and covers the dried fluid sample; and c) wherein the inserted microrelief structure introduces the molecule to the buffer mixture and prevents evaporation from the wells.

The systems and methods are capable of providing rapid and multiplexed testing to quickly identify or quantify multiple analytes in an unprocessed, or crude, sample. In some embodiments, for example, the testing may be completed in less than or equal to 45 minutes, or optionally, less than or equal to 30 minutes. In embodiments, the multiplexed methods and systems may test for more than one analyte, 10 or more analytes, or optionally, 100 or more analytes. The device may have a high number of wells, including between 1,000 to 10,000,000 wells or more that are homogeneously filled with a volume of between 1 μL and up to 10 μL to 100 μL, or between 1 μL and 1000 nL, over a rapid timeframe, including within 15 seconds or within about 60 seconds.

In an embodiment, the liquid sample undergoes minimal or no sample processing, for example, no purification or processing steps are performed on the liquid sample prior to drying, except application of a liquid to achieve desired volume and/or an anti-coagulant to avoid clots and minimize non-uniform dispersion in the wells. In embodiments, the method is rapid and highly-multiplexed. In embodiments, the method has a high sensitivity, with as low as 1 copy of a target nucleic acid per reaction well, in a total liquid sample volume of up to 10 mL. The liquid sample may undergo thermal lysing. The liquid sample may undergo chemical lysing, such as with an application of a chemical such as Triton x 100 to selectively lyse red blood cells, thereby reducing overall cellular debris before drying.

The described systems and methods are versatile, and may be used for detection of nucleic acids in a variety of biological or non-biological liquid samples. The analyte of interest may be a pathogen (e.g. a bacterium, virus, fungus or mold), a cancerous or genetically altered host cell or other biological target containing nucleic acid. Further, various techniques may be used to analyze and/or quantify an amplified sample as described herein, including optical detection (e.g. imaging, fluorescent dyes), mechanical detection (e.g. resonant frequency, stress induced mechanical bending), and electrical detection, for example, using FETs.

In an embodiment, the provided method is used in an application selected from the group consisting of: a) cancer molecular screening; b) pathogen detection from body fluids, including for diagnosis of sepsis; c) treatment efficacy assessment; d) detection of pathogens from food and water samples; e) detection of rare cells in biological sample, including circulating tumor cells; and f) detection of cell-free DNA from a body fluid sample. The systems and methods described herein may detect pathogens from solid foods, liquid foods or both solid and liquid foods.

For example, the methods and systems provided herein are compatible with pathogen susceptibility testing to different drugs, including in a patient's blood. The approaches provided herein are configured so that after dispensing whole or diluted whole blood into the wells, a bacterial culture is performed within the wells for 1-2 doubling cycles to ensure that the wells with the single bacteria have at least 2-3 bacteria. The presence of the live versus dead bacteria can be detected by using optical/fluorescence based approaches. Then drugs are introduced on the array and the viability of the cells are again optically mapped and detected. Similarly in another approach, after a brief cell growth is performed, the sample can be split and one well array can be used for the drug susceptibility testing and the other for the pathogen detection testing.

The method of any of the above claims, wherein the liquid sample is selected from the group consisting of: whole blood; saliva; urine; sweat; throat swab; vaginal swab; sputum; drinkable fluid; edible food; and environmental samples. A sample more on the solid phase of the liquid-solid phase characterization, may be dissolved in a solution with a solvent, including water, for use in any of the methods or devices described herein. In embodiments, the nucleic acid amplification comprises PCR or isothermal processes, for example, LAMP or RT-LAMP. In embodiments, the one or more target analytes comprise a nucleic acid sequence indicative of a pathogen or a disease state.

In an embodiment, for example, the buffer fluid comprises: a) an amplification enzyme and primers for nucleic acid amplification of a target analyte; and b) the amplification occurs in both the solid phase dried sample and in the solution phase buffer fluid through simultaneous diffusion of enzymes and buffer components into the dried fluid sample and target nucleic acid into the buffer fluid.

In embodiments, each of the wells has a well volume selected from the range of 1 μL to 100 μL, 1 pL to 10 μL, 1 pL to 1000 nL, 1 pL to 1 nL, or optionally, 1 pL to 250 pL. In an embodiment, the method further comprises a step of thermally lysing biological cells contained in the liquid sample. In embodiments, the substrate is part of a microfluidic chip formed of silicon, glass, polymer, or plastic. In embodiments, the detecting step comprises optically detecting fluorescent output of each of the wells or electrically detecting an electrical parameter in each of the wells, for example, by measuring a change in pH in each well by ion sensitive field effect transistors (ISFET). In embodiments, the detecting step comprising mechanically detecting a parameter, such as resonant frequency or stress induced mechanical bending, for example, by using a quartz crystal microbalance or a MEMs cantilever.

In an embodiment, for example, the method further comprises the steps of: a) filling all wells with the fluid sample;

and b) removing excess fluid sample that is not contained in the wells by introducing a gas over the wells at a pressure that is sufficient to remove excess fluid while fluid in the wells are maintained with the wells by capillary forces. In an embodiment, the gas is an inert gas, for example, inert with respect to the amplification reaction such as Nitrogen.

In an aspect, provided is a device for performing any of the methods described herein. The device may be functionally described as a 'pixelated petri dish'—a large circular substrate with the wells, and the number of wells and size of wells selected to hold the entire fluid sample and be subdivided into the wells. For example, the device may further include an instrument reader configured to perform real time imaging of each pixel to examine output from the well, including fluorescent intensity change as an indication of amplification.

The sample may be from a fluid sample or may be from a solid sample, including food, environmental, animal, or the like, that is processed by the techniques herein by converting the solid into a liquid through various methods such as blending and/or homogenization.

Any of the methods may further comprise the step of thermally lysing the sample.

Any of the methods may further comprise the step of connecting a dried material to a hydrophobic substrate release surface; fluidically sealing the array of wells by providing the hydrophobic substrate onto a top portion of the array of wells, wherein the substrate release surface faces toward the array of wells; and releasing the dried material from the hydrophobic substrate to wells.

The dried material may comprise a lyophilized or dried biomolecule connected to a bead surface. The bead surface can provide a convenient handle, with the material covalently or non-covalently bonded to the bead surface in a well-controlled and well-defined manner. The bead may then connect the material to the hydrophobic substrate and be utilize to help facilitate release into the microwell. A magnetic bead may be magnetically released. A gravitational force may be used to release the bead and material to the microwell. The material may be chemically released, including by a release agent in the microwell supernatant phase that cleaves the bead from the hydrophobic substrate and/or the material from the bead surface.

The releasing step may comprise centrifuging the fluidically sealed array of wells and hydrophobic substrate to release the dried material from the hydrophobic substrate to the array of wells.

The dried materials may comprise Crispr-cpf1, Crisper-Cas, polymerases, ligases, or other enzymes to edit, add, delete, or modify nucleic acids, or any other materials targeted to the application of interest.

At least 100 different target anlaytes are identifiable by sequential addition of Crispr-cpf1 and corresponding sequential optical detection of a fluorescent signal generated by bound cpf1 to a target analyte, including up to between 100 and 1000.

Also provided herein are systems for introducing a biomolecule to a plurality of wells in an array for target analyte detection, including for any of the methods provided herein. The system may comprise: a plate having a plurality of microwells, each microwell having: a well surface; a top portion that is physically accessible; and wherein adjacent microwells are separated by a separation surface; a hydrophobic substrate having a release surface; a biomolecule that is connected to the hydrophobic substrate release surface; wherein the hydrophobic substrate release surface with biomolecules connected thereto is configured to connect to the microwell separation surface and fluidically seal the microwells to prevent fluid transmission between different microwells filled with a fluid.

The biomolecule may be connected to the hydrophobic substrate release surface by a bead. The bead has a bead volume ($V_{bead}$) and the microwell has a microwell volume ($V_{well}$) and, optionally, $V_{well}/V_{bead}>1000$.

The system may have a plurality of hydrophobic substrates, wherein each hydrophobic substrate comprises a unique biomolecule that is different than any other hydrophobic substrate biomolecule, wherein the plurality of hydrophobic substrates provides multiplexed detection of target analytes.

Representative claims of the invention include:

1. A method of detecting one or more target analytes from a liquid sample, the method comprising the steps of: applying a liquid sample to a substrate, wherein the substrate has an array of wells; drying the liquid sample to generate a plurality of dried sample islands, with each sample island confined to a unique well; applying a reagent to each well, wherein the reagent is used for nucleic acid detection; eluting a nucleic acid from the dried sample islands with a liquid phase having the applied reagent; detecting a target nucleic acid if present in a dried sample island by a bi-phasic reaction, wherein the detecting is by electrical or optical detection; thereby detecting the one or more target analytes from the liquid sample.

2. The method of claim 1, wherein the eluting comprises: forming microchannels and/or nanochannels in the dried sample islands to facilitate introduction of reagent-containing liquid into an interior portion of the dried sample islands; wherein eluted nucleic acid remains in the microchannels and/or nanochannels; diffuses from the microchannels and/or nanochannels to the liquid phase that is a supernatant to the dried sample islands; or both.

3. The method of claim 1-2, wherein the eluting step comprises one or more of thermally, chemically and enzymatically eluting the nucleic acid of the dried sample islands.

4. The method of claim 1-3, wherein the liquid sample is a biological sample.

5. The method of claim 4, wherein the liquid sample is minimally processed, including an unprocessed raw sample.

6. The method of claims 1-5, wherein the applying the reagent step is before or after the applying the liquid sample step.

7. The method of claim 1-6, wherein the detecting step comprises amplifying a target nucleic acid in the liquid phase.

8. The method of claim 1-7, wherein the bi-phasic reaction comprises the dried sample island and the reagent suspended in a buffer fluid, wherein the buffer fluid is positioned over the dried sample island in the well.

9. The method of claim 1-8, further comprising a step of forming high surface area structures in the plurality of dried sample islands and/or a reagent liquid positioned over the dried sample islands.

10. The method of claim 9, wherein the high surface area structures are formed by mixing gas with the liquid sample before or during the drying step.

11. The method of claim 9, wherein the high surface area structures comprise a reagent-connected bead suspended in the reagent liquid.

12. The method of claim 1-11, comprising a bead-based molecule delivery system, wherein the molecule is used in an amplifying or detecting step.

13. The method of claim 12, wherein said molecule is an enzyme.

14. The method of claim 12-13, wherein said bead-based molecule delivery system comprises a liquid bi-layer application, wherein: a buffer mixture covers the dried sample islands; a carrier fluid having said bead-molecule suspended therein is disposed over said buffer mixture; and the method further comprising a step of forcing said bead-molecule into the buffer mixture.

15. The method of claim 12-13, wherein said bead-based molecule delivery system comprises a liquid tri-layer application, wherein: a buffer mixture covers the dried sample islands; an immiscible separating fluid that covers said buffer mixture; a carrier fluid having said bead-molecule suspended therein is disposed over said immiscible separating fluid, wherein the carrier fluid further comprises a surfactant that forms micelles around the bead-molecule to protect the molecule from denaturing; and the method further comprising a step of forcing said bead-molecule into the buffer mixture 16. The method of claim 12-15, wherein said bead-based molecule delivery system comprises a liquid layer and frozen liquid layer application, wherein: a buffer mixture covers the dried sample islands; a carrier fluid having said bead-molecule suspended therein, wherein said carrier fluid has a freezing point less than a freezing point of said buffer mixture; and the method further comprising the steps of: freezing the buffer mixture by cooling the buffer mixture to a temperature that is below the buffer mixture freezing point and that is above the carrier fluid freezing point; applying the carrier fluid on top of the frozen buffer mixture; forcing the bead-molecule to the frozen buffer mixture-liquid carrier fluid interface; thawing the frozen buffer mixture; and forcing said bead-molecule into the buffer mixture.

17. The method of claim 9-16, wherein the high surface area structures comprise a microrelief structure having a molecule connected thereto, the method further comprising the steps of: aligning the microrelief structure with the array of wells; inserting the microrelief structure into a buffer mixture that occupies the wells and covers the dried sample islands; and wherein the inserted microrelief structure introduces a reagent molecule to the buffer mixture and prevents evaporation from the wells.

18. The method claim 1-17, having a sensitivity as high as 1 copy of a target nucleic acid per reaction well in a total liquid sample volume of between 1 mL and 10 mL.

19. The method of claim 1-18, used in an application selected from the group consisting of: cancer molecular screening; pathogen detection from body fluids, including for diagnosis of sepsis; treatment efficacy assessment; detection of pathogens from food and water samples; detection of rare cells in biological sample, including circulating tumor cells; and detection of cell-free DNA from a body fluid sample.

20. The method of claim 1-19, wherein the liquid sample is selected from the group consisting of: whole blood; saliva; urine; sweat; throat swab; vaginal swab; sputum; drinkable fluid; environmental sample and edible food.

21 The method of claim 1-20, wherein the detecting step comprises a nucleic acid amplification process, such as a PCR or an isothermal process.

22. The method of claim 1-21, wherein the one or more target analytes comprise a nucleic acid sequence indicative of a pathogen or a disease state.

23. The method of claim 1, wherein the buffer fluid comprises: an amplification enzyme and primers for nucleic acid amplification of a target analyte; and the amplification occurs in both the solid phase dried sample and in the solution phase buffer fluid through simultaneous diffusion of enzymes and buffer components into the dried fluid sample and target nucleic acid into the buffer fluid.

24. The method of claim 1-23, wherein each well has a well volume selected from the range of 1 μL to 10 μL.

25. The method of claim 1-24, wherein the eluting step comprises thermally lysing biological cells contained in the liquid sample.

26. The method of claim 1-25, wherein the substrate is part of a microfluidic chip formed of silicon, glass or plastic.

27. The method of claim 1-26, wherein the detecting step comprises optically detecting fluorescent output of each of the wells.

28. The method of claim 1-27, wherein the detecting step comprises electrically detecting an electrical parameter in each of the wells.

29. The method of claim 28, wherein the electrically detecting is by measuring a change in pH in each well by ion sensitive field effect transistors (ISFET).

30. The method of claim 1, further comprising the steps of: filling all wells with the fluid sample; and removing excess biological fluid sample that is not contained in said wells by introducing a gas over said wells at a pressure that is sufficient to remove excess fluid while fluid in said wells are maintained with said wells by capillary forces.

31. The method of claim 30, wherein said gas is an inert gas.

32. The method of claim 1-31, further comprising the step of: connecting a dried material to a hydrophobic substrate release surface; fluidically sealing the array of wells by providing the hydrophobic substrate onto a top portion of the array of wells, wherein the substrate release surface faces toward the array of wells; and releasing the dried material from the hydrophobic substrate to wells.

33. The method of claim 32, wherein the dried material comprises a lyophilized or dried biomolecule connected to a bead surface.

34. The method of claim 1-33, wherein the releasing step comprises centrifuging the fluidically sealed array of wells and hydrophobic substrate to release the dried material from the hydrophobic substrate to the array of wells.

35. The method of claim 32-34, wherein the dried materials comprises Crispr-cpf1.

36. The method of claim 35, wherein at least 100 different target analytes are identifiable by sequential addition of Crispr-cpf1 and corresponding sequential optical detection of a fluorescent signal generated by bound cpf1 to a target analyte.

37. A system for introducing a biomolecule to a plurality of wells in an array for target analyte detection, the system comprising: a plate having a plurality of microwells, each microwell having: a well surface; a top portion that is physically accessible; and wherein adjacent microwells are separated by a separation surface; a hydrophobic substrate having a release surface; a biomolecule that is connected to the hydrophobic substrate release surface; wherein the hydrophobic substrate release surface with biomolecules connected thereto is configured to connect to the microwell separation surface and fluidically seal the microwells to prevent fluid transmission between different microwells filled with a fluid.

38. The system of claim 37, wherein the biomolecule is connected to the hydrophobic substrate release surface by a bead.

39. The system of claim 38, wherein the bead has a bead volume ($V_{bead}$) and the microwell has a microwell volume ($V_{well}$) and $V_{well}/V_{bead}>1000$.

40. The system of claim 37-39, comprising a plurality of hydrophobic substrates, wherein each hydrophobic substrate comprises a unique biomolecule that is different than any other hydrophobic substrate biomolecule, wherein the plurality of hydrophobic substrates provides multiplexed detection of target analytes.

Also provided is a system for practicing any of the methods described herein. Also provided are methods for practicing any of the systems described herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 7A. 1. Whole blood is dried at the bottom of a PCR tube. For non-thermophilic polymerase enzyme, 2a. nuclease-free water is added to the tube and the tube is heated at 95 C to elute the bacterial DNA. 3a. reaction mix with the polymerase enzyme is added to the tube post-elution. For thermophilic enzyme, 2b. reaction mix with the polymerase is added directly to the dried blood. 3b. Thermal lysis of cells is carried out at 95 C directly in the reaction mix. 4a. Lamp reaction is carried out at 65 C in a commercial thermocycler for thermophilic polymerase, and at the appropriate temperatures when using thermophilic polymerase. FIG. 7B. LAMP amplification curve for the detection of *E. coli* O157:H7 strain using our dried blood biphasic reaction.

FIG. 8A. Fluorescence intensity curves showing the amplification reaction of the three different reaction types. Blue=our dried blood bi-phasic approach. Red=single phase reaction with thermal lysis. Green=single phase reaction using a blood lysis buffer.[12] FIG. 8B. Threshold time bar graph of the corresponding splits in FIG. 8A. The dried blood-based biphasic reaction (blue) gave much shorter threshold times compared to other LAMP reactions using whole blood (red and green). The bi-phasic nature of the reaction reduces the effective concentration of contaminants in the reaction mix, thereby increasing the reaction efficiency.

FIG. 9A. 1. Whole blood is dried at the bottom of a 0.2 mL PCR tube. 2. Nuclease-free water is added to the tube and the tube is heated at 95 C to lyse the cells and elute the bacterial DNA. 3a. In the first split, reaction mix is added on top of the water and LAMP reaction is carried out. 3b. In the second split, supernatant post-elution is taken out and mixed with the reaction mix. LAMP reaction was carried out at 65 C. FIG. 9B. Threshold time bar graph of the amplification reaction. Red=reaction with the supernatant only. Blue=Complete biphasic reaction (reaction with both the supernatant and the dried blood). The complete dried blood approach gave shorter threshold times indicating that not all template DNA is eluted in the nuclease-free water added.

FIG. 10A. Real-time fluorescence curves of the LAMP amplification reaction using two strains of *E. coli* (gram-negative bacteria). FIG. 10B. Real-time fluorescence curves of the LAMP amplification reaction using two strains of *Staphylococcus Aureus* (gram-positive bacteria). The dried blood approach compatible with both gram-negative and gram-positive bacteria. The concentration for each pathogen was kept constant at 1.25e3CFU per reaction.

FIG. 11A. wzy primer set specific to the O157:H7 (non-drug resistant strain) of *E. coli* only. FIG. 11B. NDM-1 primer set specific to the drug-resistant strain of *E. coli* only. FIG. 11C. femA primer set specific to *Staphylococcus Aureus* regardless of the strain type FIG. 11D. mecA primers specific to the Methicillin Resistant *S. aureus* only.

FIG. 16A. Protocol of the bi-layered bead loading approach for the introduction of polymerase enzyme. 1-2. Blood is dried and eluted as per previous protocol. 3. Reaction mix without the polymerase enzyme is added on top of the eluted water. 4. Beads containing lyophilized polymerase enzyme, suspended in a mixture of a surfactant and mineral oil (or any other similar immiscible liquid such as hexane or toluene), is added on top of the reaction mix without the polymerase. 5a. The beads are pulled down from the mixture of Triton-X 100 and mineral oil via centrifugation. 5b. Magnetic beads are pulled down to the bottom using a strong magnet. FIG. 16B. 1.5 mL centrifuge tube containing beads mixed in mineral oil and Triton-X 100 added on top of water. FIG. 16C. The beads move down from the mixture of mineral oil and Triton-X 100 upon centrifugation (observed as brown bolus at the bottom of the tube).

FIGS. 18A-18B. Beads suspended in a mixture of mineral oil. Large clumps of beads are observed suggesting the tendency of beads to agglomerate in hydrophobic conditions. FIGS. 18C-18D. Beads in water after centrifugation. The beads are observed to be surrounded by a ring of mineral oil and are not available to interact with the template. LAMP reaction with this split yielded no amplification. FIGS. 18E-18F. Beads suspended in a mixture of mineral oil (or any other immiscible liquids such as hexane and toluene) and TritonX-100 (or any other surfactant). Clumps of beads, though smaller than in FIGS. 18A-18B, can be seen due to the non-homogenous nature of bead mixing in the mixture of mineral oil and Triton-X 100. The beads are stabilized by the presence of Triton-X 100 in the mineral oil. FIGS. 18G-18H. Beads in water after centrifugation. The beads appear in a single phase indicating that the lyophilized enzyme is free to interact with the template.

FIG. 20A. Protocol of the tri-layered bead loading approach for the introduction of polymerase enzyme. 1-2. Blood is dried and eluted as per previous protocol. 3. Reaction mix without the polymerase enzyme is added on top of the eluted water. 4. Mineral oil is added on top to prevent the mixing of the reaction mix with the polar solvent (to be added in step 5). 5. Beads containing lyophilized polymerase enzyme, suspended in a solution of Triton-X 100 and ethanol (or any solvent that do not mix with the mineral oil, and is less dense than both water and the mineral oil), is added on top of the reaction mix without the polymerase. 6a. The beads are pulled down from the mixture of Triton-X 100 and ethanol solution via centrifugation. 6b. Magnetic beads are pulled down to the bottom using a strong magnet.

FIG. 20B. Stacked layer of beads in ethanol and Triton-X 100 on top of mineral oil and the reaction mix with dried blood before centrifugation. FIG. 20C. Stacked layer of beads in ethanol and Triton-X 100 on top of mineral oil and the reaction mix after centrifugation. The brown color of the beads is no longer visible in the topmost layer after centrifugation.

FIGS. 22A-22B. Beads suspended in a mixture of TritonX-100 and ethanol. The beads are homogenously spaced with very few clumps. FIGS. 22C-22D. The beads appear homogenously mixed in a single phase indicating that the lyophilized enzyme is free to interact with the template.

DETAILED DESCRIPTION OF THE INVENTION

Figure 1A:
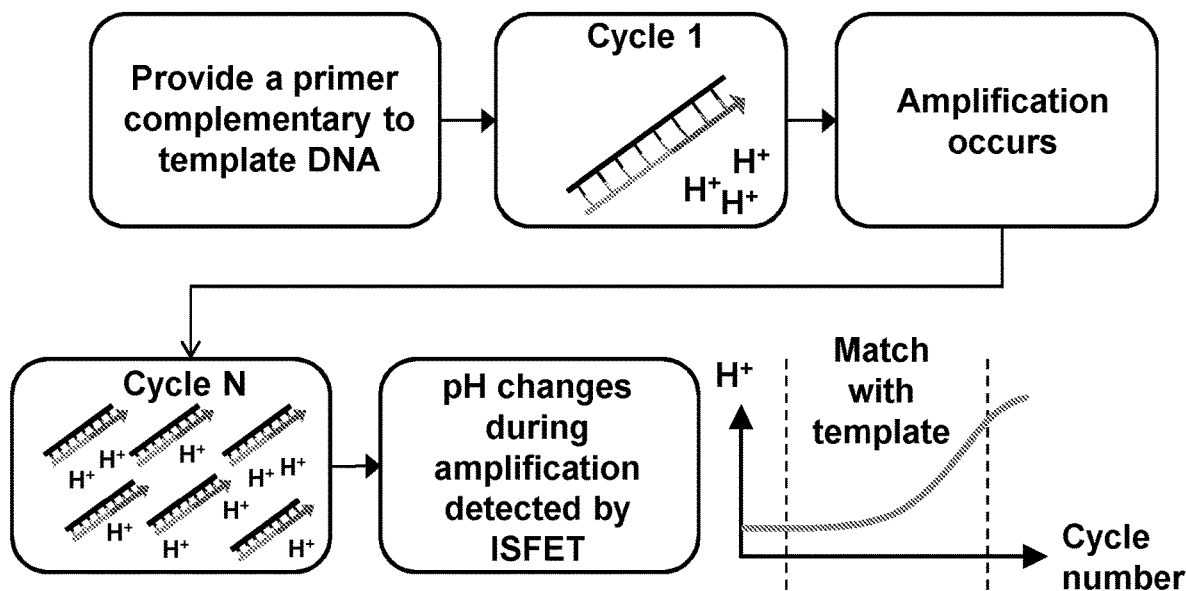
FIGS. 1A-1B. Process flow showing the principle for change in pH during LAMP reaction (FIG. 1A), and the associated measured signal from ISFET chip (red=positive, blue=negative) (FIG. 1B)[18].

As used herein, "substrate" refers to a material, layer or other structure having a surface, such as a receiving surface, supporting one or more components or devices including a microarray. Arrays may be embedded in substrates so that the array is formed within and made with the same material as the substrate. Arrays embedded in substrate may be manufactured from a single piece of material. In some embodiments, the array is a microarray. Substrates which may be useful in the methods and devices described herein include silicon, glasses, metals, insulators and/or dielectrics. Substrates may be composite materials. The substrate and/or supported microarray may be referred to as a chip herein.

"Array" refers to material or device having a number of wells, receiving chambers, void spaces or is otherwise configured to hold a number of liquid tissue samples.

Arrays may have any number of wells and may be provided in various configurations including a grid, as described herein. Wells useful in the described arrays may have any geometric shape including pyramids, cones, and rounded bottom wells with circular, square or polygonal cross-sections. Arrays may include wells having more than one dimension (e.g. depth, width), volume and/or shape. Arrays may have greater than or equal to 10,000 individual wells, greater than or equal to 100,000 wells, or optionally, greater than or equal to 1,000,000 wells. A "microarray" refers to an array of wells where at least one dimension is less than 1 mm.

"Target analyte" refers to a molecule that is desired to be detected. An example of a target analyte is a molecule that is capable of being amplified, such as a nucleic acid (DNA or RNA), so that a single target analyte may be exponential amplified by a technique such as PCR or an isothermal technique such as LAMP.

"Liquid sample" is used broadly to refer to any sample that is capable of flowing under applied shear. Accordingly, the sample may originally be a non-fluid, such as a tissue or food, but that is suspended in a fluid solvent material, so that the original solid sample is a liquid sample. Alternatively, the sample may originate as a generally liquid sample. The sample may be a "biological sample" from a human, animal, a tissue, or a cell line. "Minimally processed" refers to the obtained liquid sample where no undue processing, purification, preservation has occurred. The methods and devices, of course, are compatible with processing, including a minimally processed harvest such as application of an anti-coagulant or fluid to achieve a desired fluid parameter (e.g., viscosity) to facilitate fluid spreading over the array. "Unprocessed" refers to direct application of a fluid sample to the array, without intervening processing steps.

"Dried sample islands" refers to those portions of the originally-applied liquid sample that are positioned in wells and are capable of being contact with relevant liquid-suspended reagents, for potential amplification of one or more target analytes, if present.

"Bi-phasic reaction" refers to a reaction that occurs in each of two phases, such as a liquid phase and a solid or semi-solid phase over which the liquid phase is suspended. In the context of the instant technology, the dried sample in the well may contain target analyte of interest, and the liquid phase the necessary components for amplification of the target analyte. Target analyte may diffuse or be otherwise conveyed into the liquid phase for corresponding reaction. Similarly, the necessary components from the liquid phase my diffuse or otherwise mix into the solid dried phase, with corresponding reaction. For example, the liquid with reagents may penetrate into an interior portion of a dried sample by passive diffusion and/or be guided by a network of passages or pores formed in the dried sample, with the reaction then considered within the dried sample, particularly for passages or pores that are micro (up to 1 mm) or nano (up to um) sized. Conceptually, then, the amplification may be considered to arise from each of the "original" liquid and dried solid phases.

"High surface area structures" refers to structures that are specially configured to present increased surface area to ensure appropriate reactions. The term is used broadly, and encompasses bubbles in the solid that readily increase surface area of the dried sample available to reagent or any other process that results in passages or pores in the structure. Similarly, the reagent liquid may contain the high surface area structure, including beads to which one or more reagents are connected. The beads may then be used as a means to ensure intimate contact between reagents and target analyte, including in the solid phase.

"Reagent connected bead" refers to a reagent that is connected to the bead. The connection may be covalent or non-covalent. The connection may be via one or more linkers or receptors on the surface of the bead having specificity for the reagent.

"Microrelief structure" refers to a high surface area structure with one surface having a plurality of features that extend in a direction away from a planar surface. This effectively increases the surface area of the structure, and specifically is used to accommodate attachment of molecules, thereby increasing the number of molecules while maintaining good accessibility to liquid phase in the wells. The relief structure that is a microrelief structure refers to at least one dimension of the relief structure or spacing that is less than 1 mm. This particularly includes the thickness of the relief structure.

Example 1: Dried Liquid Sample (Blood, Urine, Saliva, Etc.) Digital Amplification Described herein is dried sample digital amplification (LAMP, PCR etc.) on a substrate (Glass, plastic, silicon etc.) with an array of microwells and with no/minimal sample processing. The drying of the sample allows processing of larger sample volumes (up to several milliliters of blood for e.g.) and preservation of pathogen nucleic acids in the sample for room temperature transportation and storage. Additional fixation of samples can be performed of the samples using common fixatives such as Formalin or acetone for extended storage of the samples for analysis.

Digital amplification (digital lamp, digital per etc.) is performed on the array of wells or microwells with dried sample in it. The array may have large number of wells (1e5-1e6) in line with large number of partitions required for digital amplification. This technique combines higher sample volume processing capability with superior sensitivity and limits of detection from digital amplifications down to single molecules starting from crude-non-purified samples. This allows the targeting of low abundance pathogens for example in sepsis, where the bacteria count can be as low 1-3 cfu/ml and unless a few ml of blood is processed, the pathogen may be excluded from the sample. Currently, no such technique exists in the literature and thus conditions such as sepsis requires culture of the pathogens before any amplification. Also, as with all digital reactions, the technique will be end-point, won't require any standard curve needed for qPCR etc., and give the exact count of pathogens at the end.

In conclusion, this technique provides a new simpler way of doing digital amplification on a petri-dish with microwells, process large sample volumes and without the usual sample purification steps. This will replace the culture method for sepsis and other conditions and make the purification steps before amplification obsolete.

To perform the reactions and amplify DNA/RNA from dried samples, high surface area structures may introduced or produced in the sample using microbubbles, microposts, etc. These high surface area structures allow easy accessibility of amplification enzymes to the pathogen even in the presence of other sample debris. High surface area structures formed in dried blood are described herein and shown in provided SEM images.

Detection Modality:

Optical—Using fluorescent probes or dyes (e.g., Sybrgreen).

Electrical—Using pH change through Ion sensitive field effect transistors (ISFET) chips.

Dried sample processing—Blood smear, urine, saliva, or a solid sample that has been liquefied.

Targeted Problem: Current primary healthcare screening and diagnosis still primarily relies on age-old techniques such as culture, microscopy, immunoassays, and on a physician's own experience. All these techniques are very time-consuming, qualitative and laborious, or lack the appropriate sensitivity and functionality to measure parameters such as drug resistance. Even after significant breakthroughs in sensitive and quantitative nucleic acid amplification testing in the past decade, information on panel of nucleic acids (mRNA biomarkers and pathogen nucleic acids) associated with a pathology (such as viral vs bacterial respiratory tract infection, their specific strains and drug resistance) is usually not available due to the limited capacity to multiplex and the associated costs and time. This has not only led to sub-optimal patient diagnosis and poor experience but also given rise to other problems such as drug resistance due to antibiotic overuse[1]. We describe a minimal sample preparation, highly multiplexed (100 or more targets from single crude sample—blood, saliva etc.), sensitive, quantitative and low-cost nucleic acid amplification technique (NAAT) from dried crude sample using loop mediated isothermal amplification (LAMP) on commercially available ion-sensitive field effect transistors or using optical detection systems (for labs).

Significance: The translation of molecular testing into routine clinical practice has been hindered by several factors such as time, multiplexing capability and cost. The current protocol for molecular testing usually involves collecting sample from the patient (Blood/oral swab/vaginal swab/urine etc.), purifying the analytes (proteins or nucleic acids) and finally running immunoassay or NAATs[2,3]. For instance, in cervical cancer screening, a pap smear microscopy and a HPV DNA test through PCR are both performed on separate samples (PCR done after analyte purification) to check for abnormal lesions and viral infection, respectively. These separate isolated tests usually take days to complete and the patient must visit the doctor's office multiple times until a diagnosis. Moreover, using the same sample, tests for other common sexually transmitted infections (STI) such as *Chlamydia* and Gonorrhea are usually not performed as it significantly adds to costs and time to multiplex higher number of targets in the current process flow. Rapid and cheap multiplexed tests can be extremely helpful for conditions such as *chlamydia* or gonorrhea, which are the most prevalent STIs worldwide, and for which up to 80% of the patients can be asymptomatic and undetected infections can lead to tubal infertility and other complications[4]. Among other frequently ordered tests at primary healthcare facilities, common infectious diseases form a major portion. For respiratory tract infections, it is often difficult for the clinician to distinguish between viral and bacterial etiologies, and this results in overuse of antibiotics[1,5]. Conventional diagnosis using culture, antigen detection or serology is either too slow or too insensitive[6] and although sensitive nucleic acid amplification methods exist, the cost to multiplex several targets prevents its use as the first choice for diagnosis[5]. This is yet another scenario where a rapid, cheap and highly multiplexed NAAT is extremely useful. For tuberculosis, where the majority of disease burden lies in low or middle income countries, the conventional diagnosis relies on sputum microscopy, solid culture and chest radiography, all of which lack in sensitivity and specificity. Recently developed immunoassays such as QuantiFERON®-TB perform satisfactorily but cannot detect multidrug resistance or HIV-associated tuberculosis[7,8]. Laboratory based sensitive nucleic acid amplification tests have been developed but few platforms (e.g. Cepheid® GeneXpert®, Roche® LightCycler® SeptiFast) provide point-of-care and rapid results[7]. This platform performs automated sample purification making it extremely expensive (GeneXpert® IV instrument-US$17000, individual cartridge ~15 US$) and multiplexing cannot be performed on the same cartridge[9]. For developing countries where sophisticated automated cell counters are still rare, blood smear microscopy is the primary technique for complete blood count and diagnosis of blood related conditions such as Malaria and Anemia[10]. Cheap and rapid nucleic acid testing without any sample preparation and on the same smear substrate for possible demographic infections will allow termination of continuous residual transmission of many infectious diseases[11,12]. For viral infections such as HIV, the point-of-care immunoassay based tests are nonquantitative and cannot be used for early diagnosis, antiretroviral therapy or infant diagnosis[4].

All the issues discussed above call for a technique that demonstrates the following features: 1. no/minimal sample preparation—reactions directly from crude biological samples; 2. highly multiplexed detection of molecular markers and co-infections from a single sample—Complete pathological profile of the patient leading to data driven decision making; 3. sensitive, specific and quantitative; 4. low instrument cost and cost per test; 5. preferably without expensive and bulky optical detection systems which also limit the number of reactions (Field-of-view for imaging is usually small); 6. preferably without active pumps or similar flow systems which require high power and are one of the main causes of experiment failures.

Molecular testing on your USB stick: Loop-mediated isothermal amplification (LAMP), which has emerged within the last two decades as an alternative to PCR for nucleic acid amplification, has been leveraged for higher specificity of its 4-6 primers, single-temperature incubation (60 C), single molecule sensitivity and increased resistance of the Bst polymerase to inhibitors that prevent PCR[13]. We and two other groups have demonstrated RT-LAMP reactions from whole blood and with excellent sensitivity down to 100 pfu/ml of viral targets such as Zika or HIV[14-16]. LAMP reactions with good sensitivities (50-100 pfu/ml) using minimally processed saliva and urine samples have also been[14,17].

The robustness of LAMP to biological contaminants in multiple unpurified sample types makes it suitable for use in our detection technique. However, the detection modality for all previous nucleic acid amplification techniques has been primarily optical making the instrument expensive and limiting the number of reactions that can be simultaneously performed (Limited field-of-view). Recently, Ion sensitive field effect transistors (ISFET) have been shown in literature for the direct detection of LAMP products through a pH based approach[18,19].

Figure 1B:
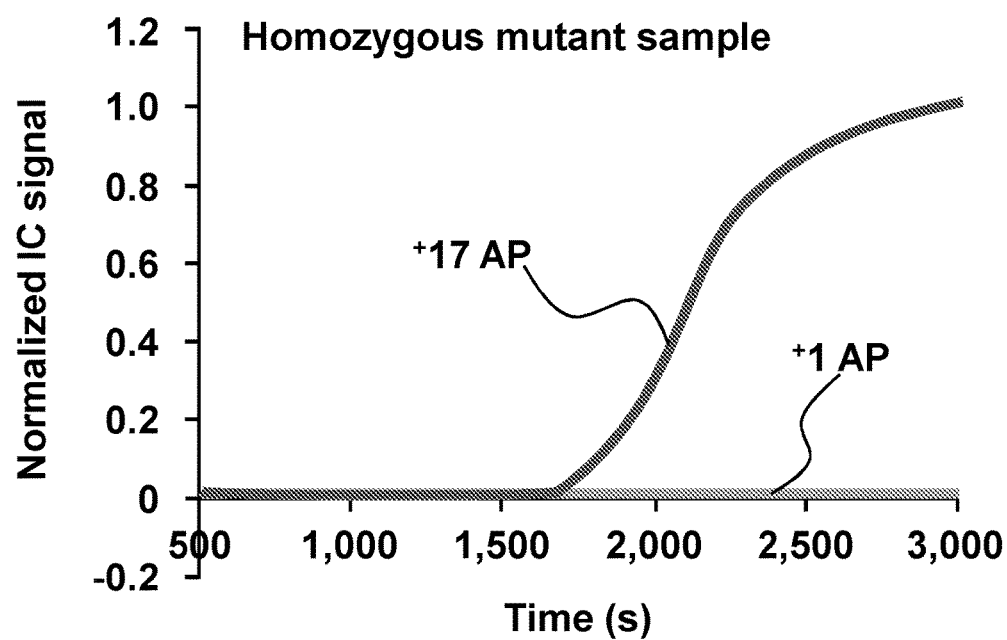
Figure 2A:
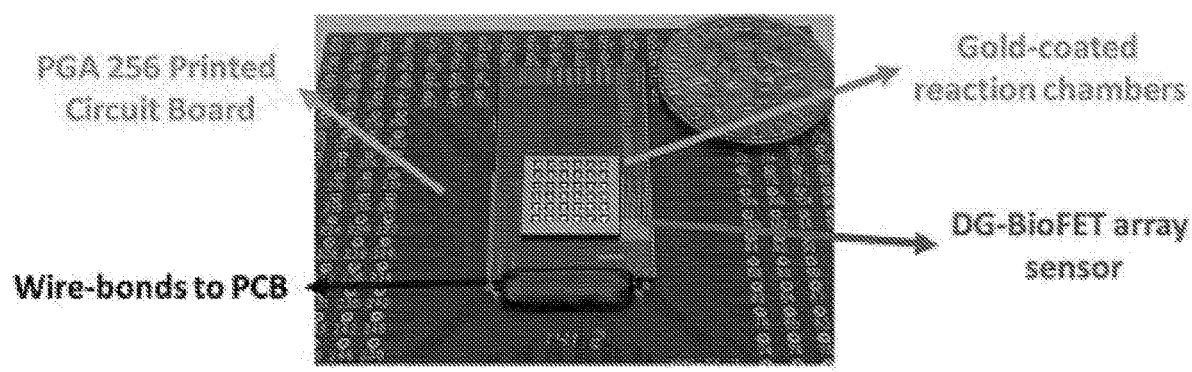
FIGS. 2A-2B. An ISFET chip with microwell array[19] (FIG. 2A), and the USB version of a similar ISFET chip[18] (FIG. 2B).
Figure 2B:
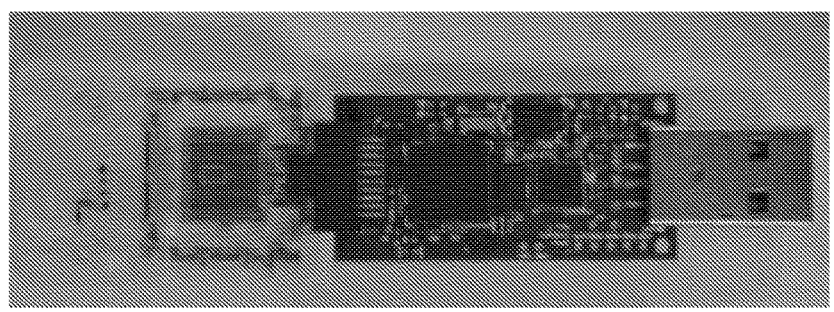

The incorporation of nucleotides into the elongating strand of nucleic acid in a LAMP reaction releases hydrogen ions which decrease the solution's pH. This drop in pH can be monitored electrically by the ISFETs (FIGS. 1A-1B). Our group has also recently demonstrated pH-LAMP reactions from purified DNA samples on a chip containing 1 million foundry-fabricated ISFETs (FIG. 2A)[19]. These devices use state-of-the-art CMOS fabrication techniques to produce a million sensors on a 7 mm*7 mm area. This greatly reduces the footprint of our device, and enables massively parallel reactions that can detect multiple targets at the same time in a single LAMP reaction (100-1000 ISFETs per reaction with 1 million ISFETs per chip=>1000 parallel reactions possible).

Apart from the massive targeted multiplexing, eliminating active microfluidic flow systems which require microfluidic pumps would not only help in bringing down the cost per test, but also simplify the process-flow and reduce the number of potential malfunctioning elements. Described herein is the testing from dried samples (blood from finger prick, saliva etc.) on wax paper or glass slide. Dried blood spots (DBS) have been used in NAATs for the direct detection of analytes with minimal sample purification[20]. The stability of nucleic acids in dried samples has also been well characterized with HIV-1 RNA being shown to be stable in dried blood spot for a year at room temperature[21].

Figure 3:
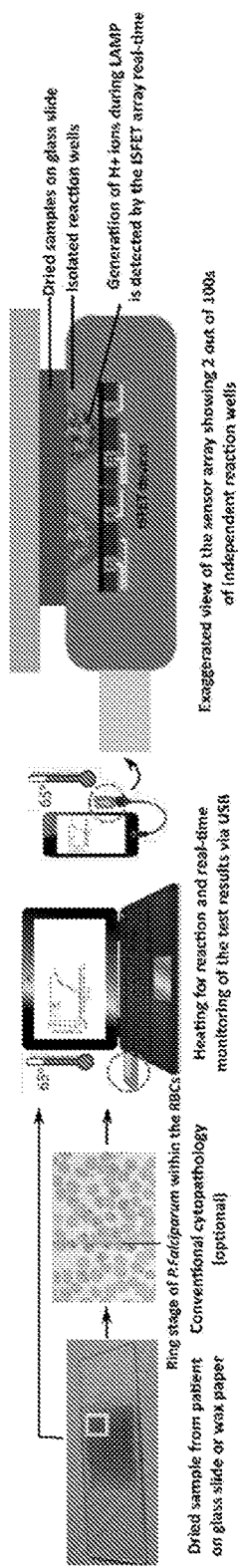
FIG. 3. Schematic showing the process flow of the USB-based molecular sensing technique.

Described herein is the combination of pH-LAMP reactions on commercially available chips with the process of drying crude biological samples on a glass slide or wax paper with microwell array. These slides or wax papers are pre-printed with the primers of a panel of chosen nucleic acid biomarkers or pathogen sequences using cheap commercially available microarray printing technology[22]. FIG. 3 shows the schematic and the overall process flow for our technique. Briefly, dried biological samples (blood, saliva, urine etc.) on a glass slide/wax paper with microwells interface with our transistor chip. The template-free amplification reagents will be loaded into the wells from a single input and LAMP reaction will be performed at 65 C. The dried template in the crude sample will rehydrate in the LAMP solution and initiate amplification reaction once a matching template-primer pair is found, and, the real-time change in pH during the reaction is monitored by the ISFET sensor surface.

Figure 4B:
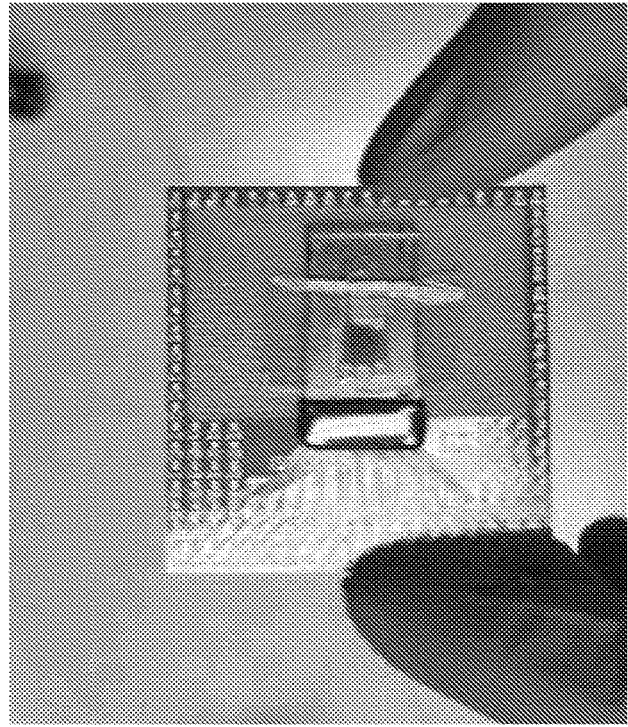
FIGS. 4A-4B. Glass slide with dried blood (FIG. 4A), and glass slide interfacing the ISFET chip with patterned microwell array (FIG. 4B).
Figure 4A:
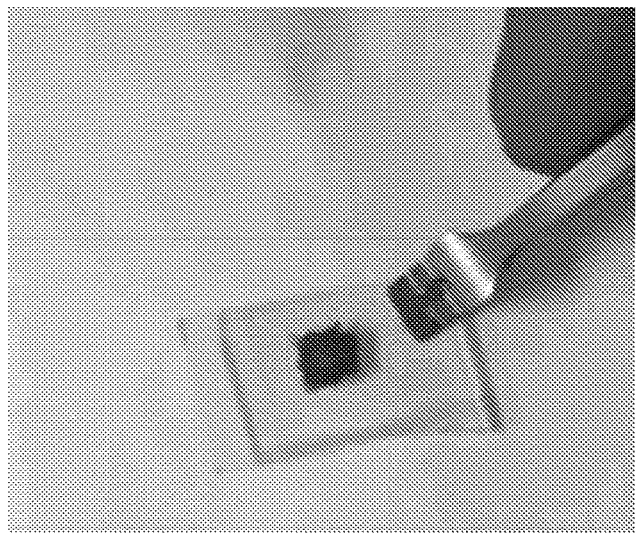
Figure 5:
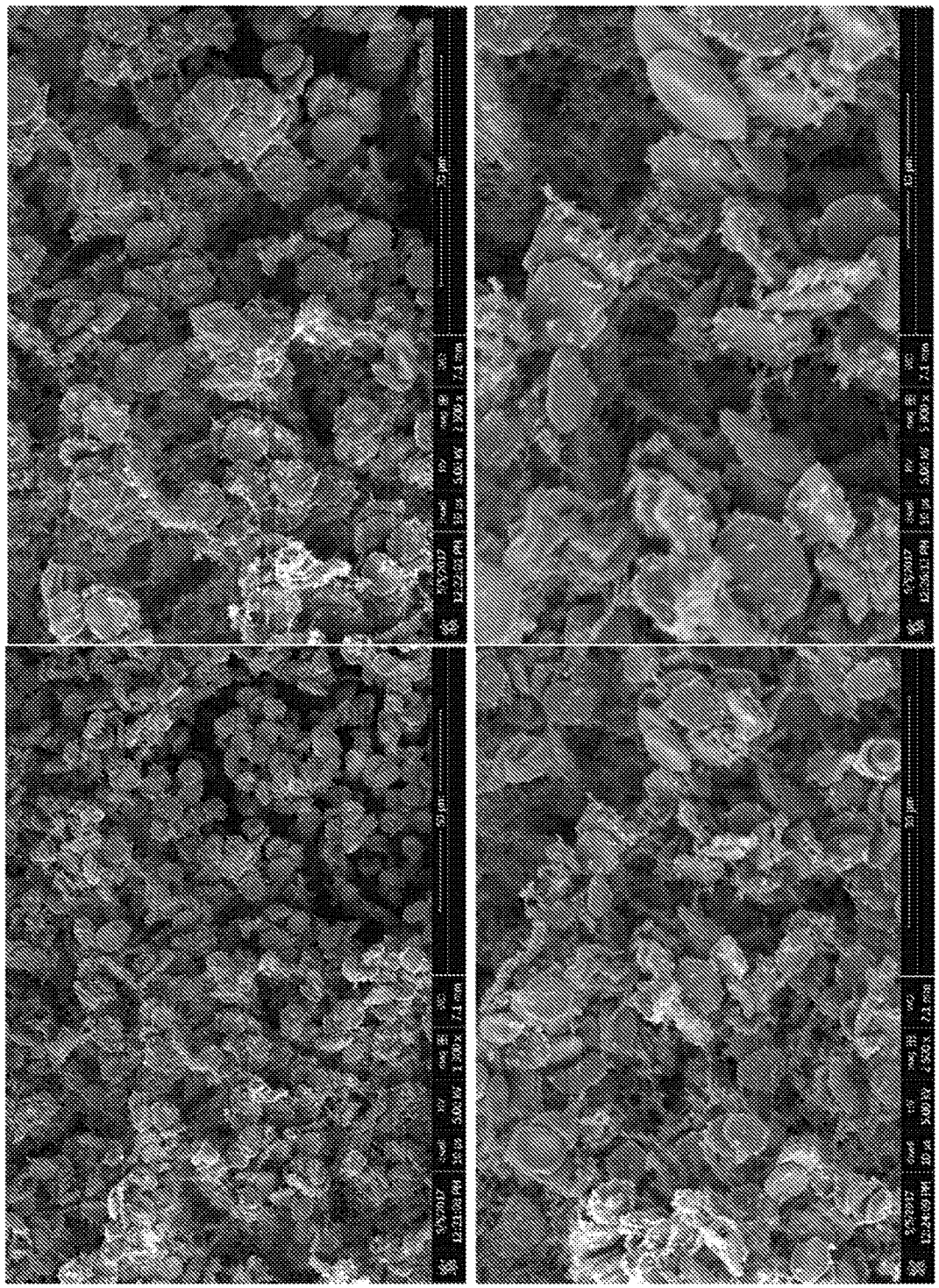
FIG. 5. Provides SEM images of dried blood samples.
Figure 6:
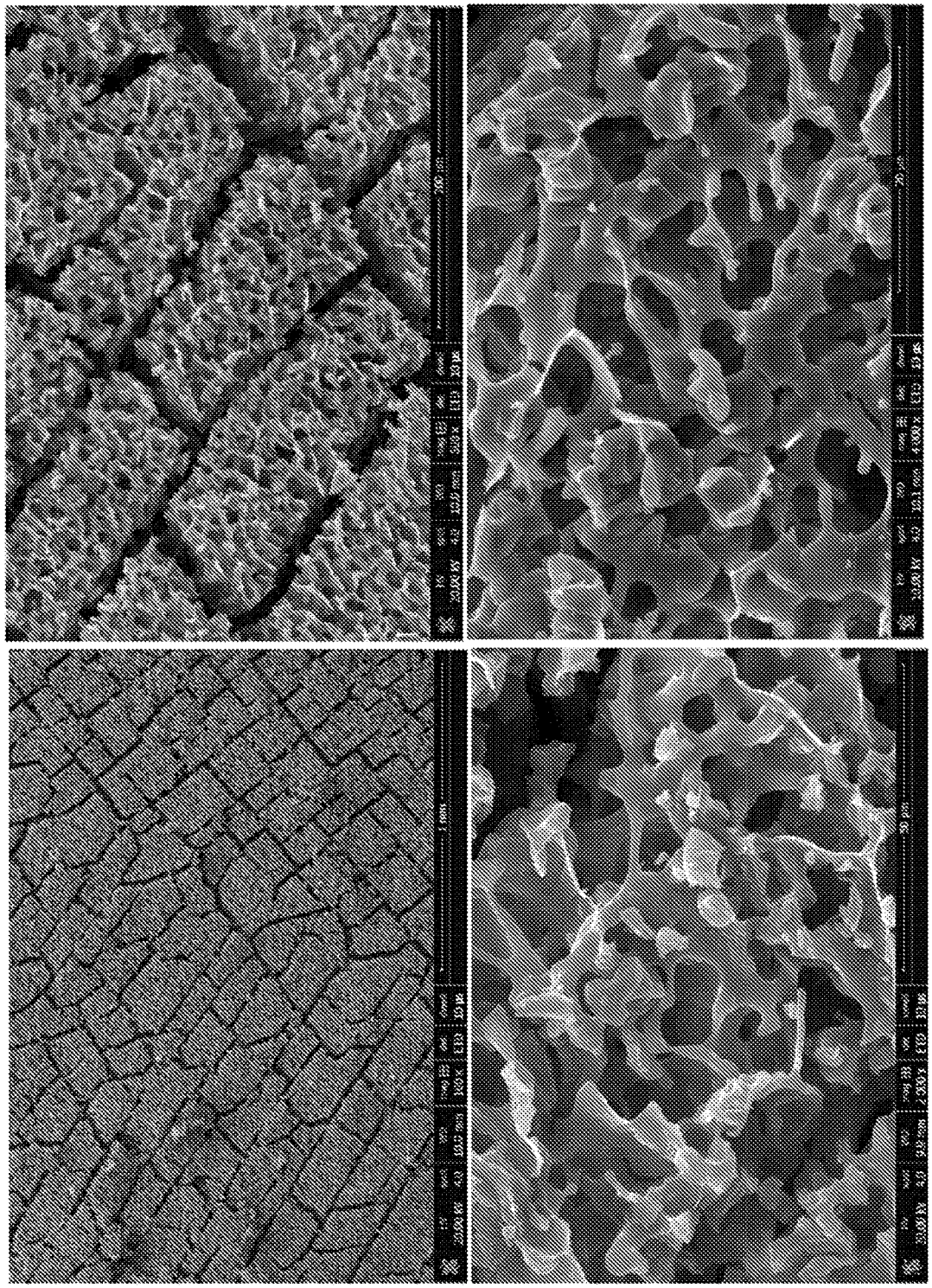
FIG. 6. Provides SEM images of high surface areas structures generated by microbubbles formed by mixing gas with the liquid sample before or during the drying step.

The use of glass slide as an optional substrate also enables conventional cytopathology to be done on the same slide prior to the molecular testing in a primary healthcare facility. FIGS. 4A-4B show a sample chip bonded to a glass slide containing dried blood for pH-lamp measurement. Electrical detection of LAMP reaction will significantly reduce the footprint of the system and enable the sensing system to be coupled to a USB stick (FIG. 3). This allows end users to use the 5V output from laptop or smartphones to perform the isothermal amplification reaction and immediately view the results on their devices.

Impact: To summarize, described is a technique that follows through on all the parameters discussed in significance—No sample preparation and rapid, highly multiplexed, sensitive, quantitative and very low-cost. As the trends are shifting towards molecular diagnostics, the ability to visualize a panel of 100-1000 or more nucleic acid biomarkers and pathogens from the same starting sample within 30 minutes will cause a paradigm shift towards data-centered diagnostics and decision making. With our commercially available ISFET devices from Taiwan semiconductor manufacturing company (TSMC), major chip fabrication players (INTEL or TSMC) can be an active part of the product manufacturing pipeline, significantly reducing the time-to-market and costs (for reference, a 4 GB USB with billions of transistor costs <2$ off the shelf[23-25]), and bringing their expertise in electronic device fabrication.

For home based diagnostics or surveillance, the product market is currently restricted only to a few basic devices since the 1970s, such as glucose monitoring for diabetic patients. There are no at-home tests for cancer molecular screening, common infections or for recurring measurements in response to treatment such as for HIV patients. As we move towards quantitative data driven medical science and treatment decisions, our one-step, rapid, cheap, massively multiplexed and simple detection of molecular biomarkers or pathogens will not only impact primary healthcare facilities but also cater to the huge market of home-based molecular diagnostics.

Higher Blood Processing Through Blood Drying:

Diseases such as sepsis where the pathogen count is a few cfu/ml require high blood volume processing capabilities to detect the pathogen of interest. The current mode of diagnosis is blood culture which takes 3-5 days and the chances of mortality during this time are extremely high. The conventional purification steps with commercial RNA/DNA extraction kits are not efficient in extracting rare pathogen DNA in the presence of significantly more abundant human nucleic acids. We process dry blood on chip, pixelate it and perform digital PCR or LAMP directly from the pixelated dried blood.

Use of Microbubbles to Create a High Surface Area Structures:

Microbubbles filled with gas and mixed with whole blood will create higher surface area microstructures within the dried blood and expose the bacteria, allowing easy access of enzymes to the pathogen for amplification.

REFERENCES

1. Lundborg, C., Mölstad, S. & Olsson, E. Antibiotic prescribing in outpatients: a 1-week diagnosis-prescribing study in 5 counties in Sweden. Scand. J. (2002).
2. Akhmetov, I. & Bubnov, R. V. Assessing value of innovative molecular diagnostic tests in the concept of predictive, preventive, and personalized medicine. EPMA J. 6, 19 (2015).
3. Fauci, A. S. & Morens, D. M. The Perpetual Challenge of Infectious Diseases. N Engl. J. Med. 366, 454-461 (2012).
4. Mabey, D., Peeling, R. W., Ustianowski, A. & Perkins, M. D. Diagnostics for the developing world. Nat. Rev. Microbiol. 2, 231-240 (2004).
5. Brittain-Long, R. et al. Multiplex real-time PCR for detection of respiratory tract infections. J. Clin. Virol. 41, 53-56 (2008).
6. Gunson, R., Collins, T. & Carman, W. Real-time RT-PCR detection of 12 respiratory viral infections in four triplex reactions. J. Clin. Virol. (2005).
7. Lawn, S. D. et al. Advances in tuberculosis diagnostics: The Xpert MTB/RIF assay and future prospects for a point-of-care test. Lancet Infect. Dis. 13, 349-361 (2013).
8. McNerney, R. & Daley, P. Towards a point-of-care test for active tuberculosis:
obstacles and opportunities. Nat. Rev. Microbiol. 9, 204-213 (2011).
9. Cepheid|GeneXpert IV. Available at: http://www.cepheid.com/us/cepheid-solutions/systems/genexpertsystems/genexpert-iv. (Accessed: 30 Apr. 2017)
10. Bain, B. J. Diagnosis from the Blood Smear. N. Engl. J. Med. 353, 498-507 (2005).
11. WHO|A WHO external quality assurance scheme for malaria nucleic acid amplification testing. Meeting report. WHO (2016).
12. WHO|Global tuberculosis report 2016. WHO (2017).
13. Notomi, T. et al. Loop-mediated isothermal amplification of DNA. 28, (2000).
14. Priye, A. et al. A smartphone-based diagnostic platform for rapid detection of Zika, chikungunya, and dengue viruses. Sci. Rep. 7, 44778 (2017).
15. Curtis, K., Rudolph, D., Nejad, I. & Singleton, J. Isothermal amplification using a chemical heating device for point-of-care detection of HIV-1. PLoS One (2012).
16. Damhorst, G. L. et al. Smartphone-Imaged HIV-1 Reverse-Transcription Loop-Mediated Isothermal Amplification (RT-LAMP) on a Chip from Whole Blood. Eng. (Beijing, China) 1, 324-335 (2015).
17. Song, J. et al. Instrument-Free Point-of-Care Molecular Detection of Zika Virus. Anal. Chem. 88, 7289-7294 (2016).
18. Toumazou, C. et al. Simultaneous DNA amplification and detection using a pH-sensing semiconductor system. Nat. Methods 10, 641-6 (2013).
19. Duarte-Guevara, C. et al. On-chip electrical detection of parallel loop-mediated isothermal amplification with DG-BioFETs for the detection of foodborne bacterial pathogens. RSC Adv. 6, 103872-103887 (2016).
20. Barker, R. H. et al. A simple method to detect Plasmodium falciparum directly from blood samples using the polymerase chain reaction. Am. J. Trop. Med. Hyg. 46, 416-426 (1992).
21. Brambilla, D. et al. Multicenter Evaluation of Use of Dried Blood and Plasma Spot Specimens in Quantitative Assays for Human Immunodeficiency Virus RNA: Measurement, Precision, and RNA Stability Multicenter Evaluation of Use of Dried Blood and Plasma Spot Specimens in Quan. *J. Clin. Microbiol.* 41, 1888-1898 (2003).
22. Arrayit Microarray Printing Pins and Printheads—Professional 946 Stealth ChipMaker™ Spotting Gene Chips Bead Array Manufacturing. Available at: http://www.arrayit.com/Products/Microarray_Printing/microarray_printing.html. (Accessed: 30 Apr. 2017)
23. A Flash Storage Technical and Economic Primer. flashstorage.com (2015).
24. Taiwan engineers defeat limits of flash memory. phys.org
25. Micron Technology, Inc.—3D XPoint™ Technology. Available at: https://www.micron.com/about/ourinnovation/3d-xpoint-technology. (Accessed: 30 Apr. 2017)

Example 2: Detection of Bacteria in a Dried Blood Sample

Detecting extremely low target analyte or pathogen count (1-10 CFU/ml or lower) has been a fundamental challenge in the medical diagnostics' and food testing industry[2] due to extremely low signal to noise ratio. Cell culture, which usually take 1-5 days, is the only way of detecting these low pathogen levels in any sample.[1,3,4] Sepsis, a clinical syndrome that results from dysregulated inflammatory response to infection leading to organ dysfunction has very high morbidity and mortality.[4] It is also estimated to be the most costly inpatient diagnosis, accounting for more than $23 billion annually in US alone.[5] Since sepsis usually has very low pathogen counts (1-3 CFU/ml)[6] the only way for diagnosis is culture followed by nucleic acid amplification or direct molecular detection after a positive blood culture.[3] Blood cultures (or other sample cultures) are very time consuming (1-5 days), have a very high false negative rate and do not work for fastidious pathogens such as *Chlamydia pneumoniae* which are harder to culture.[3,7]

Our approach involves directly amplifying (nucleic acid amplification) target analyte from dried crude biological samples. We perform this amplification in a pixelated petri dish with an array of wells making the whole approach "Digital"—The number of wells which give positive amplification give the exact count of the copy number of analytes. This is a practical way of doing digital amplification with extremely high sensitivity (1 cfu/ml or lower) from crude, unprocessed samples, while processing large quantities (1-10 mL) of the biological sample. The processing of large amount of the biofluid is required to effectively sample the target analyte or pathogen which is present in very low concentrations. We have shown that for reactions from crude samples, bi-phasic reactions, consisting of separate dried sample phase and separate solution phase (with the amplification enzymes and reaction mix) have lower threshold times and are fundamentally superior compared to single phase (mixed) reactions where the crude sample is mixed with the amplification enzymes and buffers. This is likely because the interaction between inhibitory contaminants in crude samples and the amplification enzymes are reduced in the scenario where the sample is dried and does not mix with the enzyme solution above. We have also shown that this nucleic acid amplification reaction, post thermal lysis (universally applicable) of the target, initiates both in the solid phase (dried sample) and in the solution phase through the simultaneous diffusion of enzymes and buffer components into the dried sample cake and the diffusion of the target DNA (e.g. Pathogen DNA) into the solution above.

We start by drying the body fluid sample (blood, urine, saliva, stool, nasopharyngeal sample etc.), or food sample slurry (after grinding), in a pixelated petri dish with an array of wells. (The well numbers can range from 1e3 to 1e6 or higher, and, the well volume can vary from 10 picoliters to few nanoliters). The pixelation or partitioning of the sample into many (1e3 to 1e6 or higher) sub samples in separate wells helps in improving the signal-to-noise ratio and the efficiency of the reaction by performing independent reactions in each well. For example, if 1 ml of blood containing only 1 bacteria (starting concentration=1 bacteria/ml) is equally partitioned into 1e6 number of wells, then that one bacteria will end up going in one of the wells and the final bacteria concentration for that well will become 6 orders of magnitude higher (1 bacteria/nanoliter). The drying of the sample has the following roles:

1. Reduces the effective sample size to handle. For example, whole blood has approximately 50% plasma and so after drying, 1 mL of whole blood will become approximately 0.5 mL of dried blood cake.
2. Traps the target of interest in the wells.
3. Preserves the RNA/DNA for months at room temperature avoiding the need for cold chain for sample storage and stability. We confirm the stability of dried blood samples and repeatability of amplification from dried blood with spiked pathogens (*E. coli* or *S. Aureus*) for up to 28 days.
4. Drying of crude biological sample allows nucleic acid amplification to occur in the wells even with very high abundance of contaminants (For e.g. —Erythrocytes and other cell types in blood, Extracellular matrices etc.). The contaminants remain as a cake at the bottom of the wells behaving similar to a precipitate in the solution and have minimal effect on the reaction.
5. The dried sample tethers to the substrate (wells) and behaves like a single solid object which is easier to handle and store.

Figure 7A:
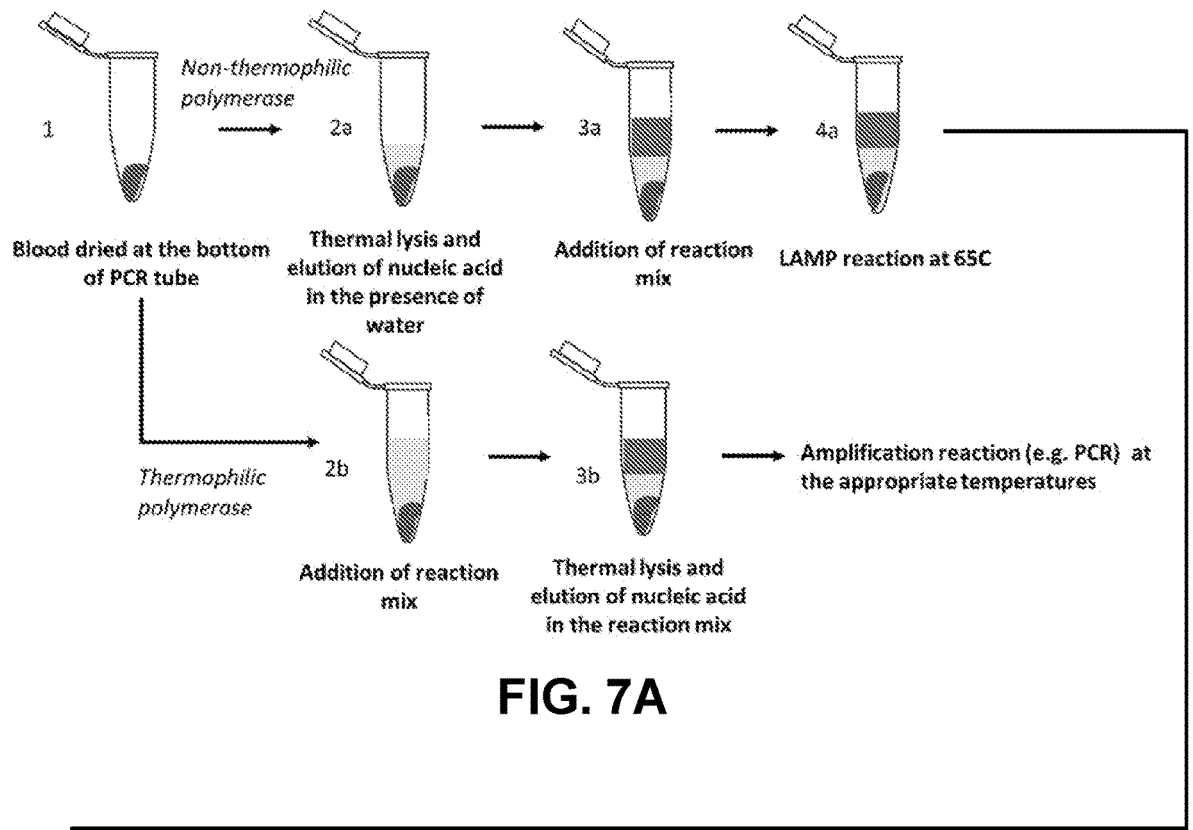
FIGS. 7A-7B. Process flow of the dried liquid sample bi-phasic reaction.
Figure 7B:
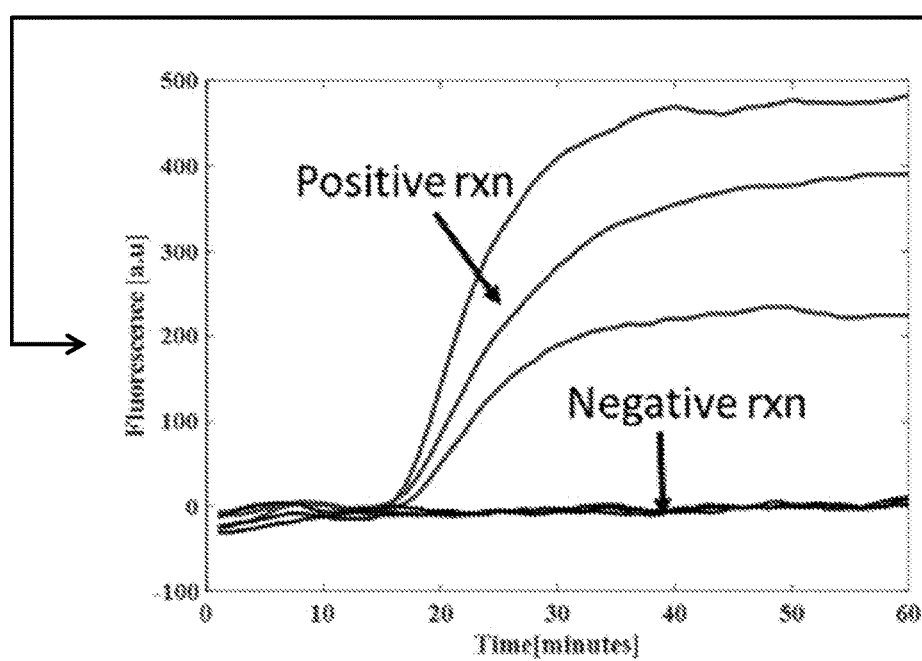

Bi-Phasic Amplification Reaction:

To validate the reaction mechanism of our bi-phasic reaction approach, we carried out tube-based loop mediated isothermal amplification reaction (LAMP) for the detection of wzy gene for the O157:H7 strain of *E. coli* in whole blood (FIGS. 7A-7B). Unprocessed whole blood spiked with the spiked *E. coli* was dried at the bottom of PCR tubes, followed by elution of bacterial DNA in the presence of nuclease-free water by thermal lysis at 95 C. Thermal lysis is a standard procedure of lysing cells (also works with viruses, and other pathogens) and eluting their nucleic acids (gram-positive and gram-negative bacteria).[8-10] Upon lysis of the cells, the reaction mix is added and LAMP amplification is carried out at 65° C. In our bi-phasic reaction, the dried blood and associated contaminants at the bottom of the tube remains as a solid single phase with minimal diffusion into the reaction mix above. Inhibitors remain as precipitates at the bottom of the tubes, and do not become part of the reaction. The amplification reaction initiates both in the solid phase (dried sample) and in the solution phase through the simultaneous diffusion of enzymes and buffer components into the dried sample cake and the diffusion of the target DNA (e.g. Pathogen DNA) into the solution described herein.

Our bi-phasic reaction approach can be made compatible with any sample type (urine, saliva, food) to test for the presence of any nucleic acid markers via any nucleic acid amplification test (NAAT).

Figure 8A:
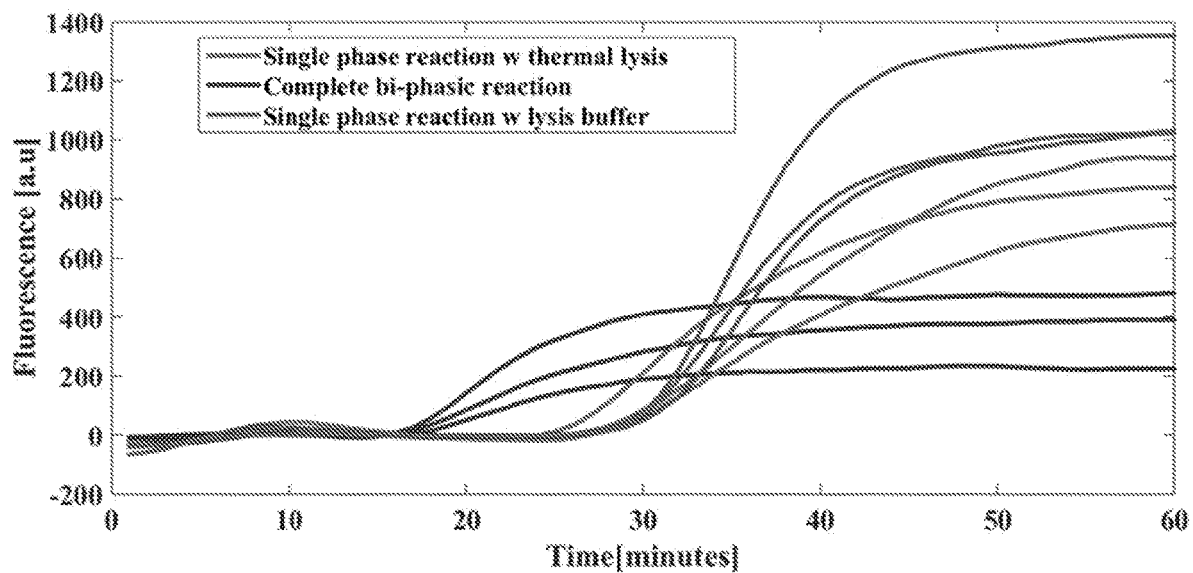
FIGS. 8A-8B. Comparison of the described dried blood reaction with other whole-blood based LAMP technique.
Figure 8B:
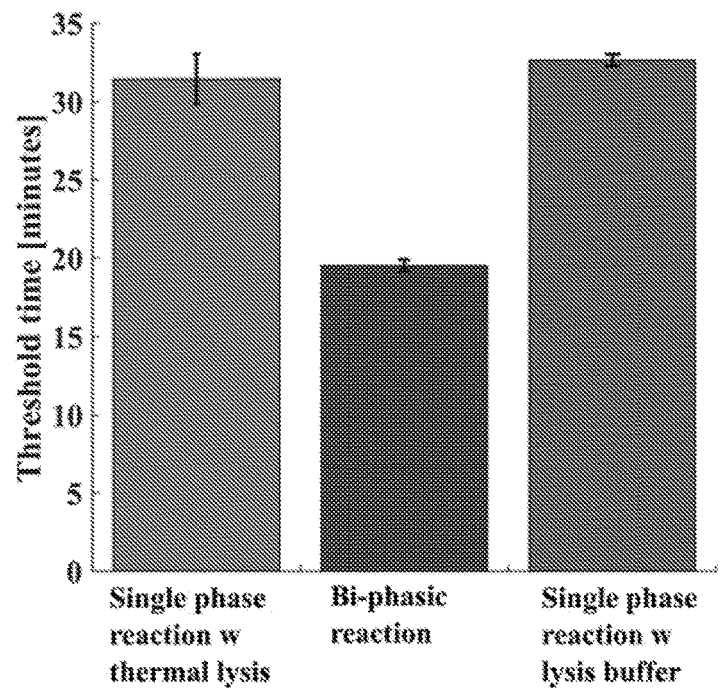

To validate that the described bi-phasic reaction is superior to other single phase reactions, we compare the reaction approach to other LAMP reaction techniques that use unprocessed whole blood. The final reaction concentration of the spiked pathogen was kept the same at 1.25e3 CFU/uL across all the splits tested. The bi-phasic reaction using the dried sample yielded much shorter threshold times compared to the two other alternate techniques. (FIGS. 8A-8B).

Figure 9A:
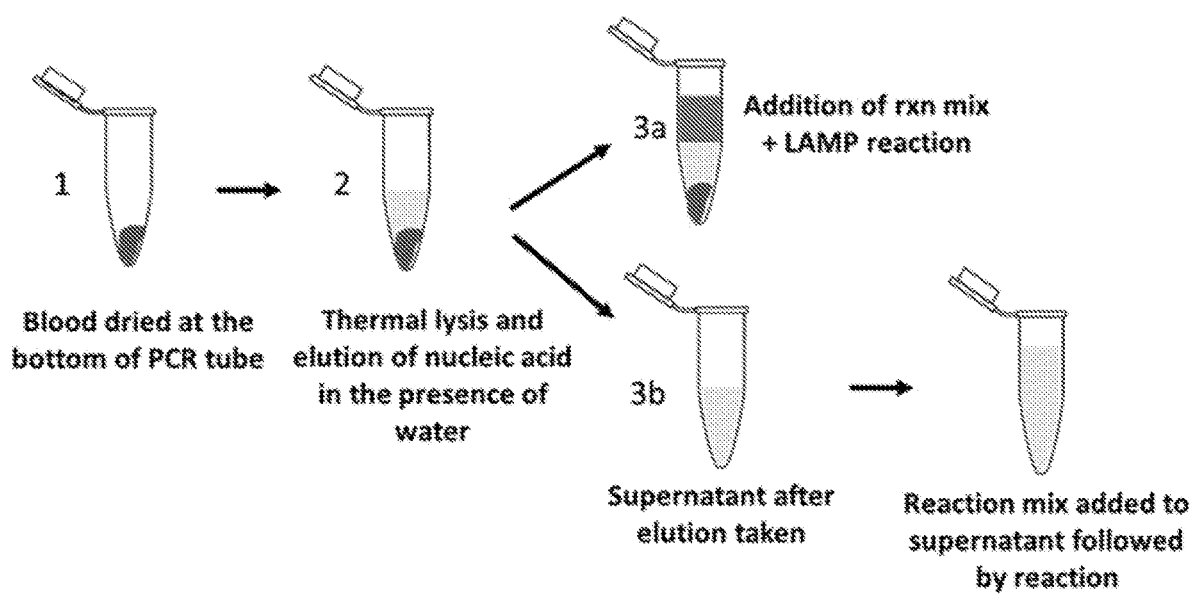
FIGS. 9A-9B. Template accessibility test.
Figure 9B:
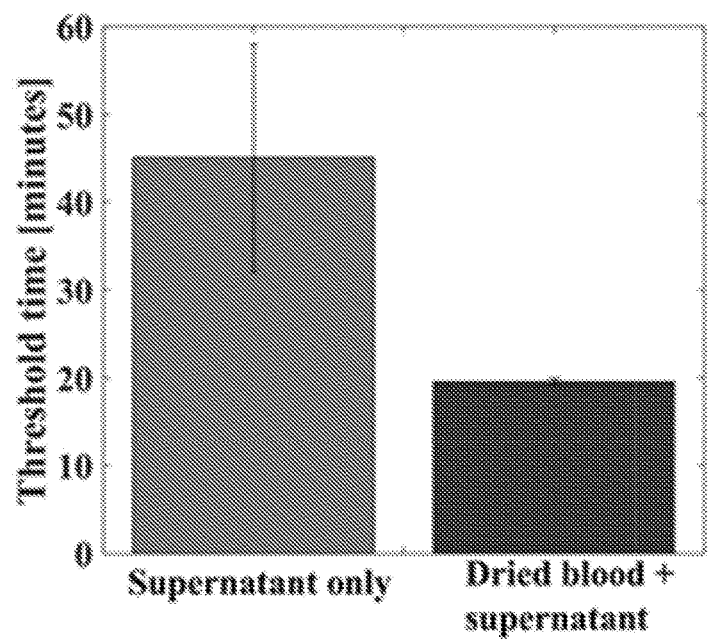

The bi-phasic reaction using dried blood is initiated in both the solid dried blood phase and the liquid phase (with the eluted DNA). (FIGS. 9A-9B) Reaction carried out with only supernatant water post elution gave much higher threshold times compared to the usual dried blood reaction (dried blood+supernatant solution). This indicates that not all of the pathogen DNA is eluted into the solution above the dried blood cake and indicates the presence of target DNA in the dried blood cake. The accessibility of the Polymerase enzyme to this trapped DNA in the dried blood cake is not an issue as evident by the consistent and repeatable threshold times across experiments. The final concentration of the O157:H7 strain of E. coli was 1.25e3 CFU/mL for both the experiments.

Figure 10A:
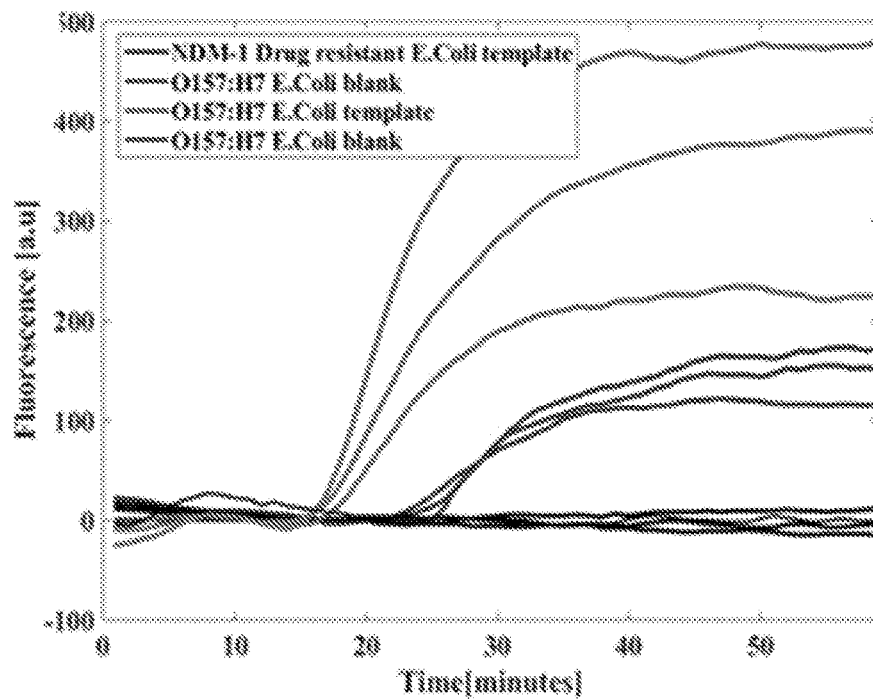
FIGS. 10A-10B. Dried blood reaction compatibility testing.
Figure 10B:
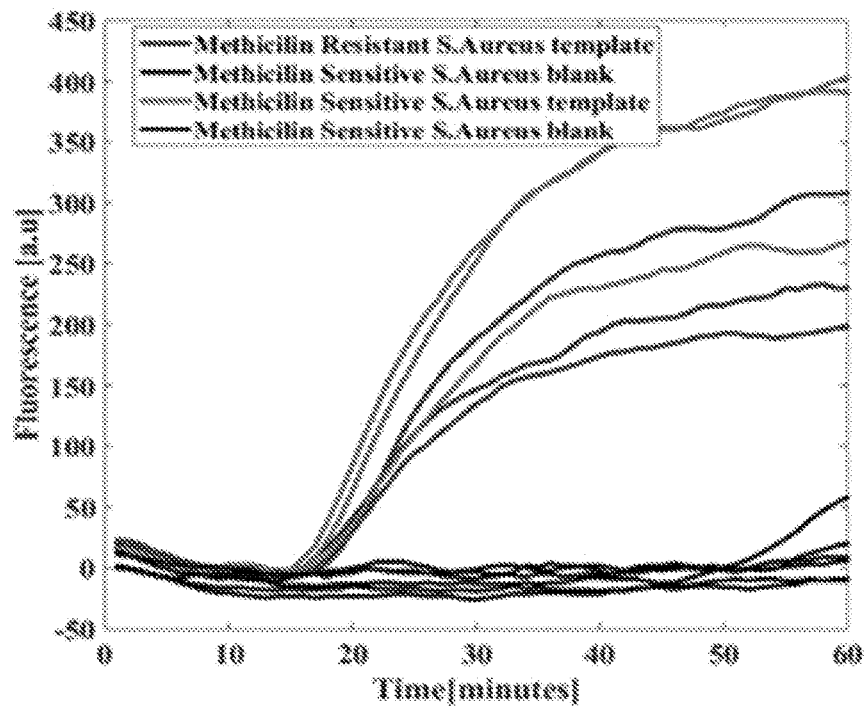
Figure 11A:
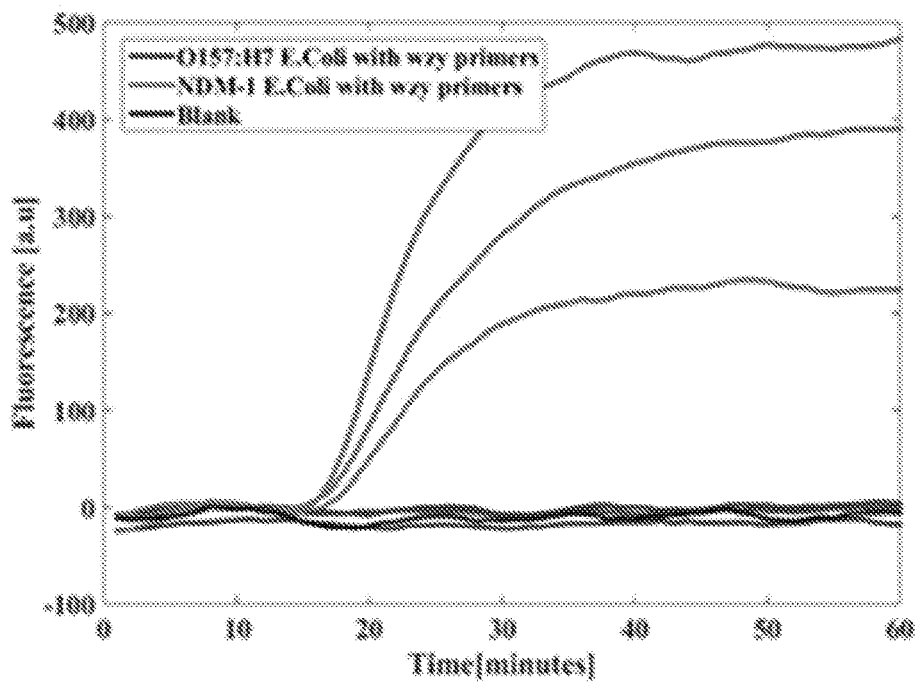
FIGS. 11A-11D. Primer cross-reactivity test. Real-time fluorescence curves of the LAMP amplification reactions used to validate the primer specificity.
Figure 11B:
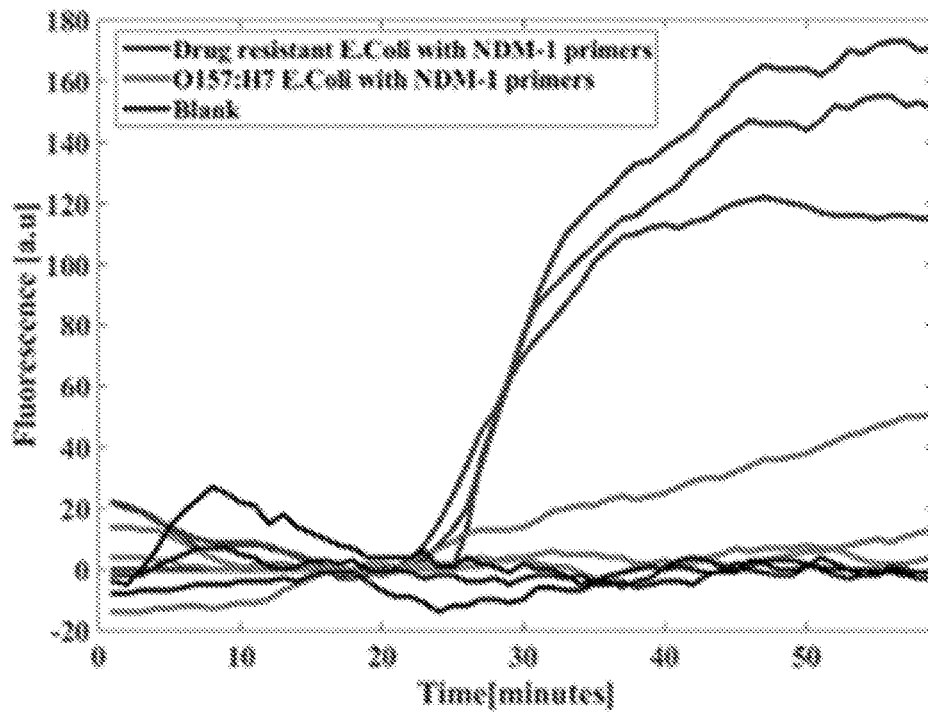
Figure 11C:
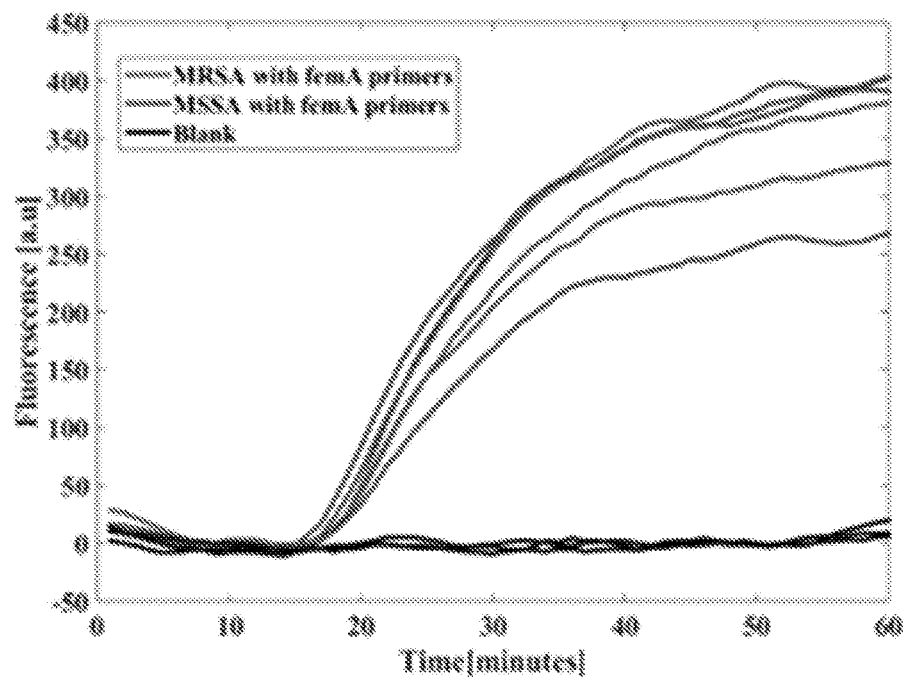
Figure 11D:
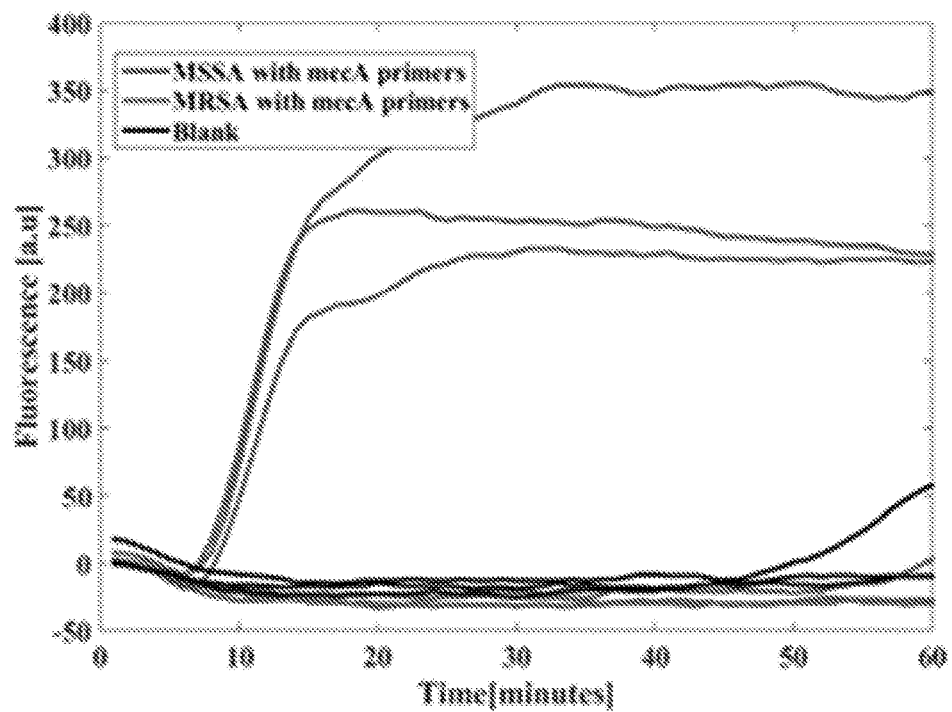

Bi-Phasic Reaction with Different Pathogens:

Elution protocol via the thermal lysis proved to be efficient for the detection of both gram-negative and gram-positive using our bi-phasic reaction approach. LAMP reactions were carried for the detection of two gram-negative bacteria (carbapenem sensitive and carbapenem-resistant of E. coli), and two gram-positive bacteria (methicillin sensitive and methicillin resistant strain of S. Aureus). (FIGS. 10A-10B) The detection of these targets was specific and yielded no non-specific amplification. The cross-reactivity of each primer sets was also confirmed using our bi-phasic reaction approach (FIGS. 11A-11D).

Figure 12:
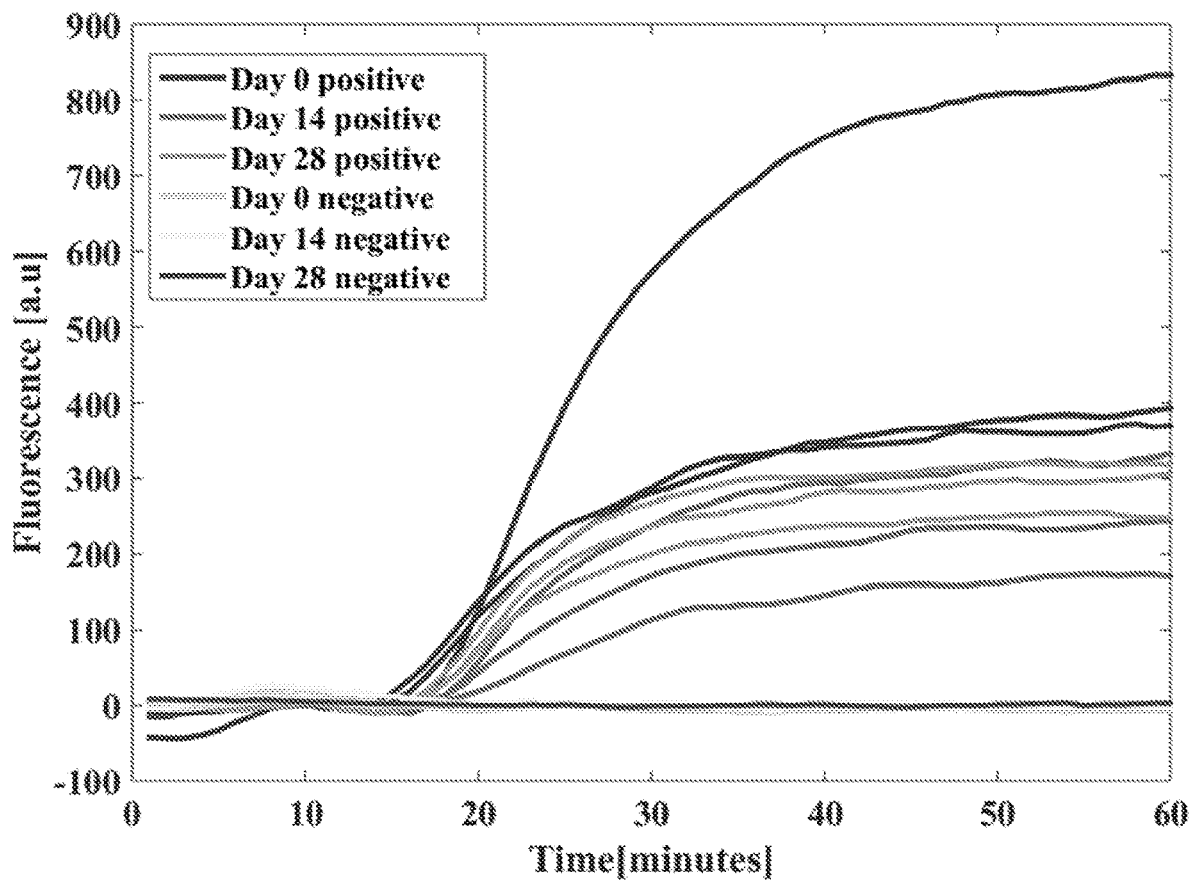
FIG. 12. Stability of dried blood over time. Real-time fluorescence curves of the LAMP amplification reactions to test the dried blood stability. Blood dried up to 28 days were tested. The threshold times for the positive amplification at day 0 were found to be identical to the threshold times for positive amplification at day 28. No non-specific amplification was observed even with blood dried for 28 days.
Figure 13A:
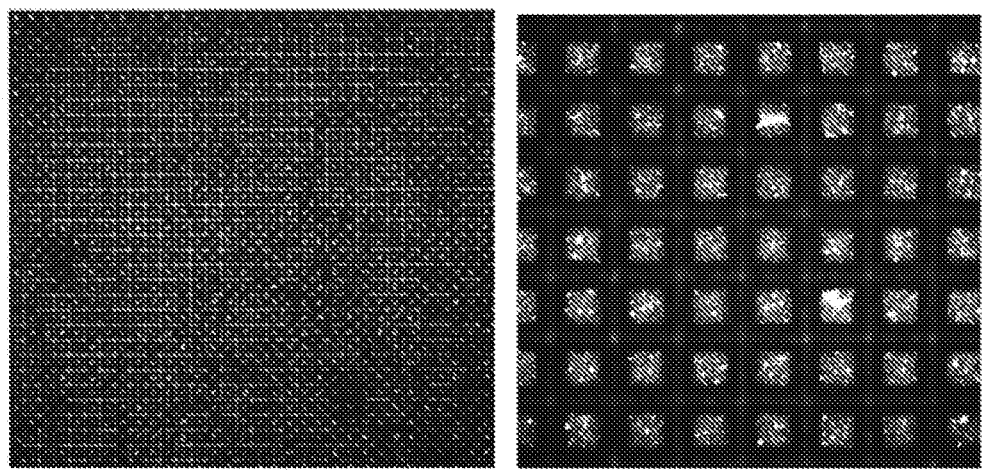
FIGS. 13A-13C. On-chip blood loading. Microscopy images of dried blood in (FIG. 13A) 100 um, (FIG. 13B) 300 um, (FIG. 13C) 500 um wells. The well edges are clearly visible in all of the chip types indicating minimal cross-talk between adjacent wells. The filling was also observed to be uniform in the wells.
Figure 13B:
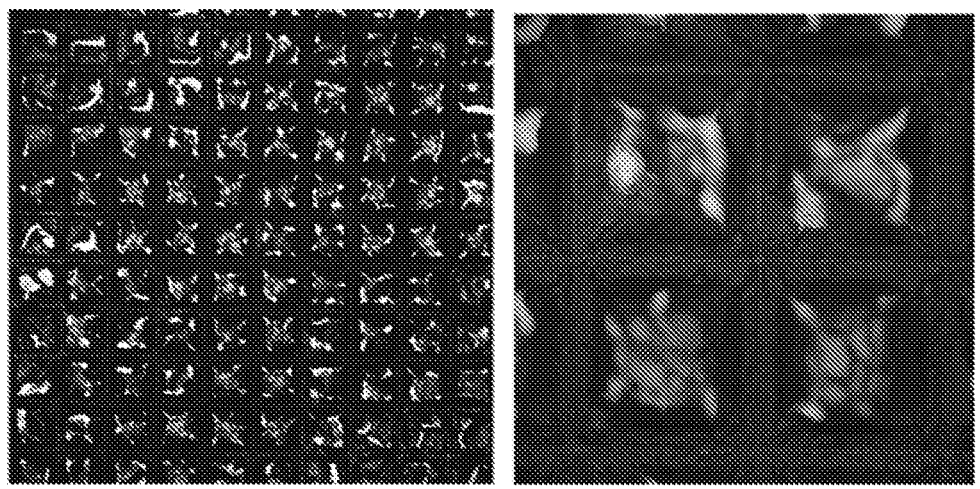
Figure 13C:
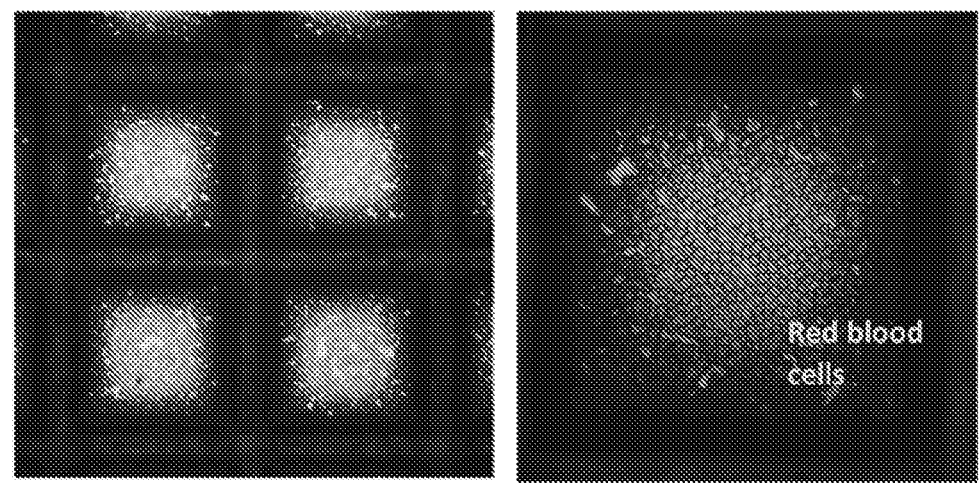

On-Chip Digital Amplification Reaction:

To increase the sensitivity of the bi-phasic reaction, the bi-phasic reactions are combined with digital nucleic acid amplification reaction. The digital amplification is carried out by reaction in microfluidic chips (silicon, glass, plastic) with >1e6 wells. The sample is loaded into the million wells and then dried on our chip. The low starting pathogen count, low volume of liquid per well and large number of partitions implies that there is either 1 or 0 target (pathogen) per well (poison statistics for digital amplification). Moreover, the low volume per well increases the effective concentration of the template in the positive reaction. The digital amplification reaction can be monitored end-point using a fluorescent microscope or a portable fluorescence reader. The number of positive wells, characterized by greater fluorescence at the end-point, indicates the number of pathogens/target in the starting sample. The blood loading protocol is optimized on-chip to achieve uniform filling per well with minimal cross-talk between wells. (FIG. 12.) The chips are made hydrophilic (using Amino silane or PLL), and an excess amount of whole blood is loaded onto the chip to ensure all the wells were filled with blood. Upon complete filling, excess blood is removed by blowing air with a $N_2$ gun. The blood equivalent to a well volume is retained in each well due to dominant capillary forces and the excess is removed due to air pressure. This rapid sample loading technique takes only a few seconds to load greater than million wells (with picoliter to nanoliters of volume) homogenously. Then, the blood is allowed to dry, and chip filling was qualitatively assessed via optical microscopy.

Enzyme for Amplification Reaction:

After loading the blood on chip, the target DNA/RNA is eluted in the reaction mix at 95° C. for 1-2 minutes. The reagent loading may be done in either a one-step, or, a two-step process depending on the thermal stability of the polymerase. In the case of polymerase chain reaction which requires thermal cycling, or isothermal amplification reactions utilizing a thermophilic enzyme (stable at 95° C. for a few minutes), the reaction mix with the enzymes is added to the wells with dried blood and the nucleic acids are eluted at 95° C. For amplification reactions not using a thermostable polymerase, such as LAMP Bst polymerase which gets denatured above 70° C., the polymerase is introduced into reaction mix separately after the DNA/RNA elution step via thermal lysis. The elution step in such scenario is done in an amplification compatible buffer mix containing all the ingredients for amplification except the enzyme (everything except enzymes are thermostable at 95° C.).

There are two broad strategies for the introduction of non-thermophilic polymerase post DNA/RNA elution as follows:

a. Bead-based lyophilized enzyme delivery
b. Lyophilizing enzymes on micropillars and introducing into the wells as a cover to the chip Both the techniques utilize the lyophilization of polymerase enzymes either on beads or micropillars.

Figure 14:
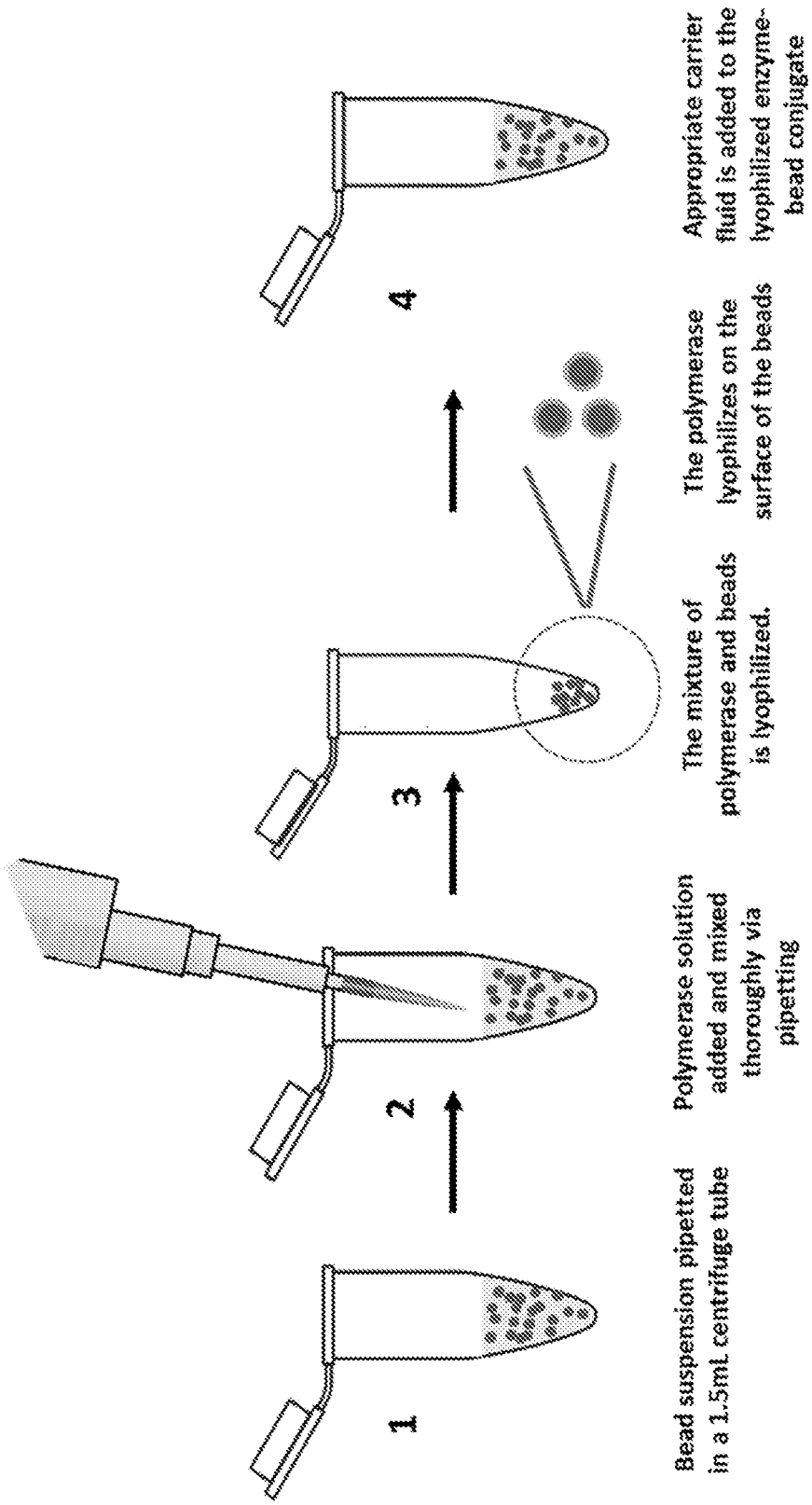
FIG. 14. Mechanism of polymerase lyophilization on beads. 1. Beads are added to a 1.5 mL centrifugation tube. 2. Polymerase enzyme solution is added to the tube with beads and mixed thoroughly by pipetting. 3. The mixture of beads and polymerase is lyophilized. The polymerase lyophilizes on the surface of the beads. 4. Prior to the amplification reaction, the appropriate carrier fluid is added each to lyophilized tube and mixed thoroughly before being pipetted into the reaction.

Bead-Based Enzyme Delivery:

FIG. 14 show the principle for lyophilizing enzymes on beads. The large number of beads per tube minimizes the lyophilization of beads on tube walls and maximizes enzyme retention on beads. Once the enzymes have been lyophilized on beads, a carrier fluid is used to pick up the beads and transfer them on chip and into the wells. The considerations for this step are:

1. A solvent that is miscible or soluble with the reaction mix (already in wells) may not be directly used to pick up the beads. Since the wells are already filled with buffer mix in the prior nucleic acid elution step, adding more of soluble/miscible solvent will cause overflow of the solvent and allow cross-talk between adjacent wells. This violates the independent well criteria required for independent and isolated reactions.

2. An immiscible solvent may be used which is lower in density than reaction mix solution to pick up the beads. This allows the carrier fluid to float on top of the wells while the denser beads with enzymes can fall into the underlying wells.

3. A miscible solvent (soluble with water/reaction mix) may be used as a carrier fluid if we have a separating layer of immiscible fluid in between. See the tri-layered approach described herein for explanation.

4. A miscible solvent can be used if the reaction mix is frozen post elution and the bead loading is done in sub-zero temperatures (degree C.). This prevents the molecular diffusion and mixing of the 2 miscible liquids (reaction mix and carrier fluid). The freezing temperature of the carrier fluid in such scenario should be below 0° C. and below the operating temperature of the process, so it remains as a liquid even when the reaction mix is frozen.

Based on the above criteria, the bead based polymerase delivery can be divided into 3 sub-categories.

i. Bi-layered approach (uses immiscible (with reaction mix) solvent as carrier fluid).
ii. Tri-layer approach (uses miscible/soluble solvent as carrier fluid with a separating immiscible fluid in between).
iii. Loading at sub-zero temperatures (uses low freezing point miscible/soluble solvent as carrier fluid at sub-zero temperatures).

Bead-Based Bi-Layered Approach:

In the bi-layered approach to introduce polymerase into the reaction wells, the lyophilized beads are suspended in a mixture of a carrier fluid and a surfactant. The carrier fluid is both immiscible in and lighter than water so that it can stay afloat on top of the buffer mix in our microfluidic chip. The surfactant allows good mixing of the beads in carrier fluid by reducing the surface energy of the beads and keeping them de-agglomerated in the carrier fluid (otherwise the interactions between polar lyophilized beads and non-polar carrier solvent are not energetically favorable resulting in poor mixing). The lyophilized beads are polar (due to the enzymes present on them), and they are solubilized in a non-polar solvent (immiscible liquid—e.g. mineral oil, hexane, toluene) through the formation of nanoscale reverse micellar structures by the surfactant molecules. The mechanism for the polymerase lyophilization is described in FIG. 14. Both surfactants were tested with both low hydrophile-lipophile balance (HLB) such as PEF-2000, and high HLB such as Triton-X 100.

Figure 15:
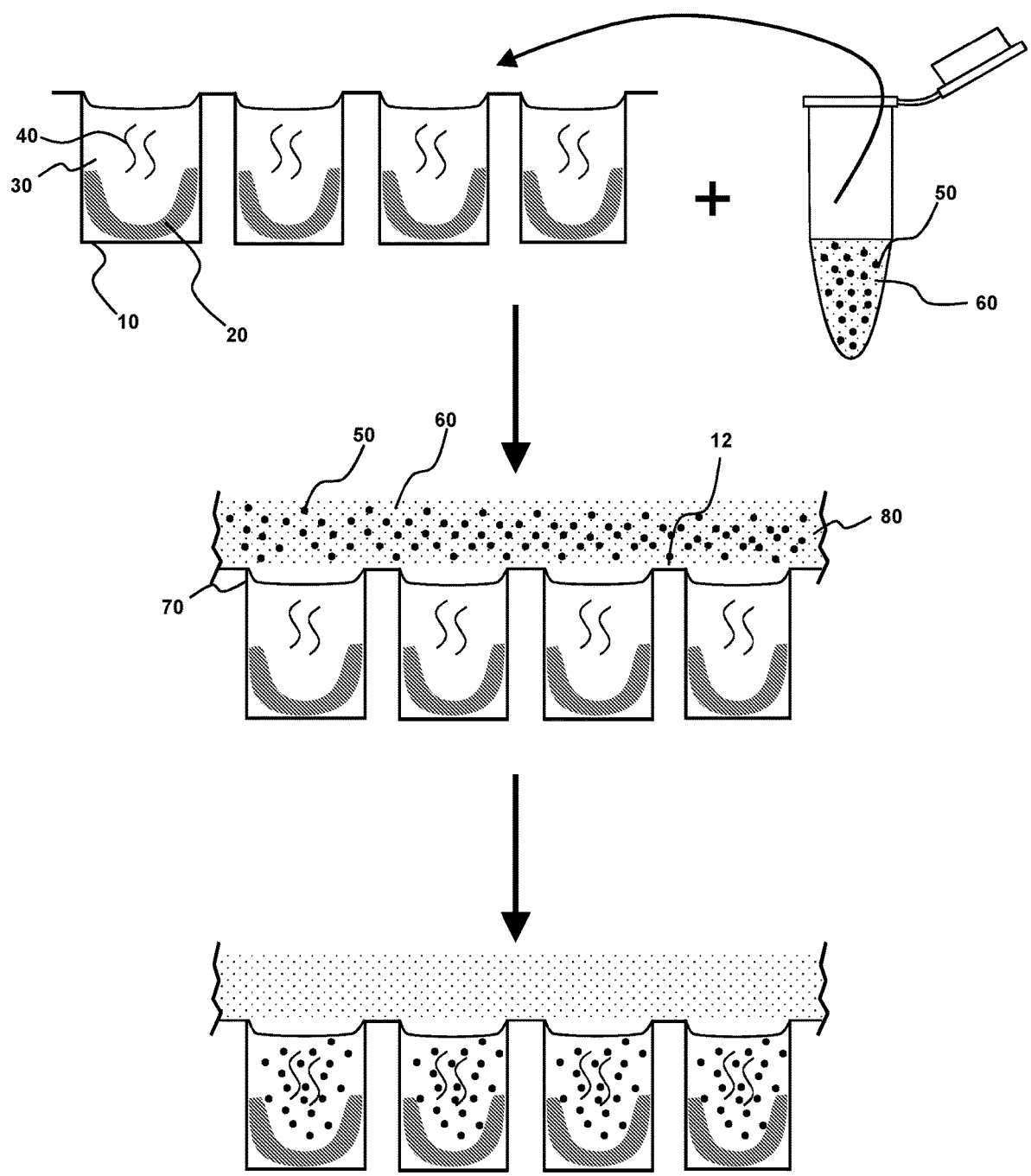
FIG. 15. On-chip process flow for a bi-layered fluid bead technique.

The on-chip schematic with the process flow (steps 1-4) for this bi-layer approach is illustrated in FIG. 15, illustrating the system having a plate with a plurality of microwells 10, dried fluid sample 20, liquid phase 30 in the microwells 10 and target nucleic acid 40. Beads 50 are provided in barrier layer (also referred to as a carrier fluid) 60. The beads are forced into the liquid phase, such as by application of release force, e.g., centrifugation or passive settling under gravity. In the top panel, wells with dried blood are filled with buffer mixture, after DNA/RNA elution, as illustrated by nucleic acid 40 in the buffer mixture liquid phase 30. A reagent (also referred herein as a biomolecule), such as a lyophilized enzyme on beads 50 suspended in an immiscible carrier fluid 60, is introduced to the plate with wells 10. The middle panel illustrates carrier fluid 60 with beads 50 to form a barrier layer (also referred herein as a hydrophobic substrate 80) over a top portion 70 of the microwell 10. Adjacent microwells 10 are separated by a separation surface 12. The bottom panels shows beads pulled from the hydrophobic substrate to the wells using centrifugation or other force, such as magnetic force for magnetic or magnetizable beads 50. In this manner, the hydrophobic substrate 80, with beads that may have a biomolecule, connects to the micorwell separation surface 12 to fluidically seal adjacent microwells and prevent fluid transmission between microwells, thereby reliably preventing unwanted cross-talk.

Figure 16A:
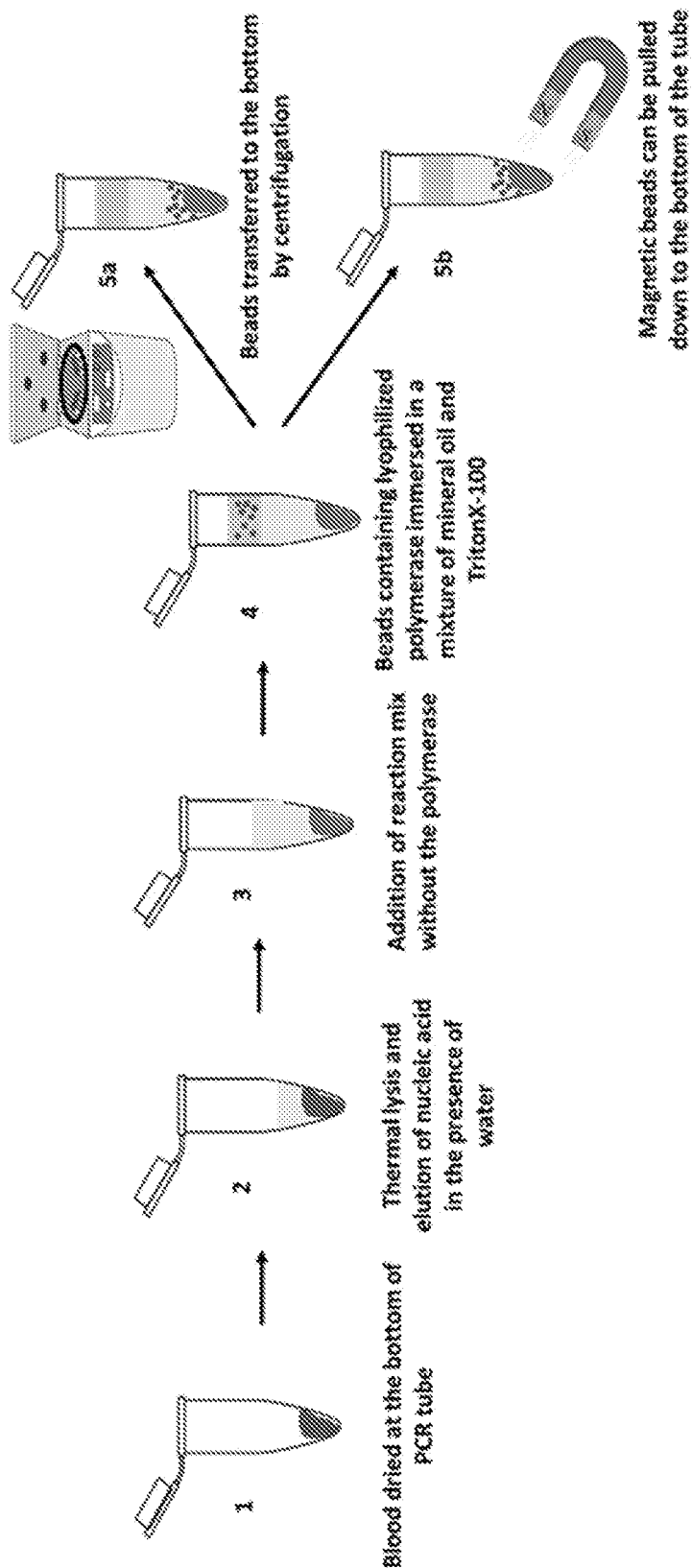
FIGS. 16A-16C. Tube-based bi-layer bead loading approach.
Figure 16B:
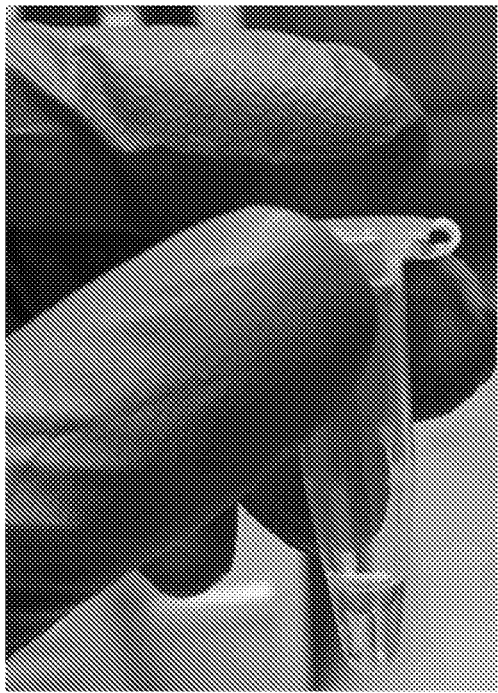
Figure 16C:
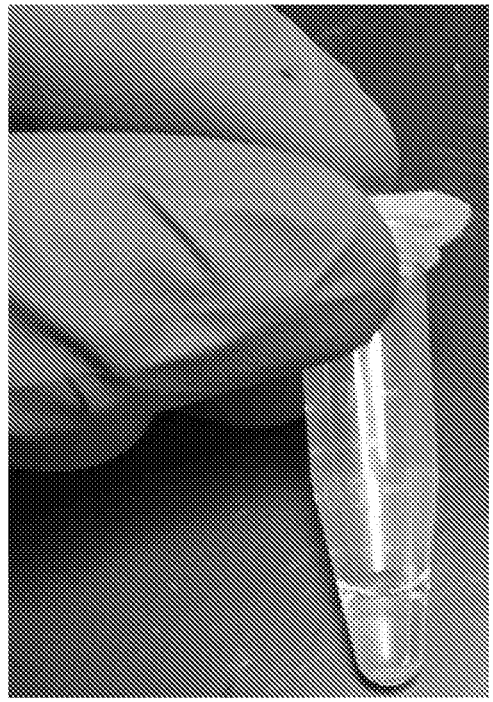
Figure 17A:
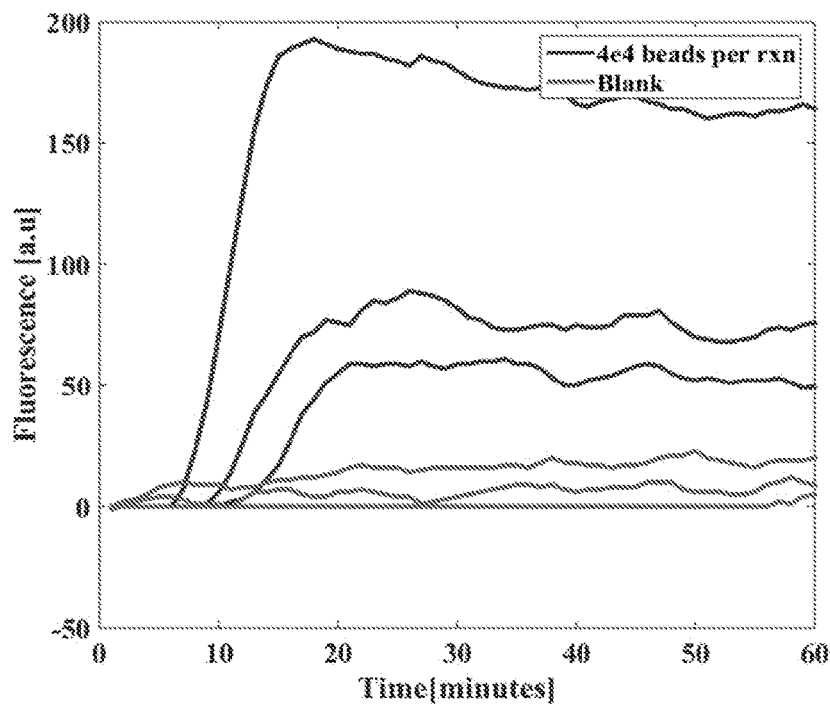
FIGS. 17A-17B. Bi-layered approach enzyme delivery LAMP reaction. LAMP amplification curves using the bi-layer approach with (FIG. 17A) 40000 polystyrene beads per reaction, and (FIG. 17B) 4000 magnetic beads per reaction.
Figure 17B:
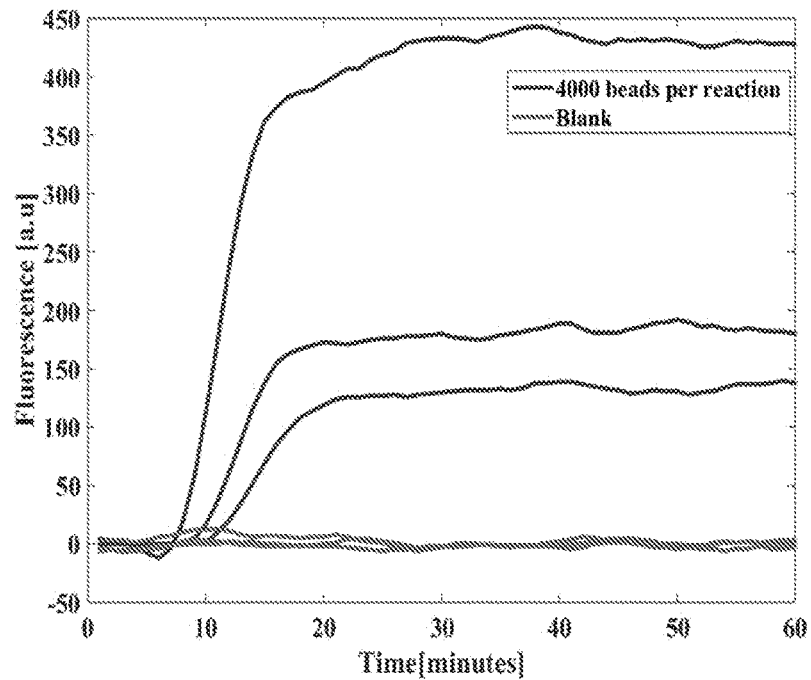
Figure 18A:
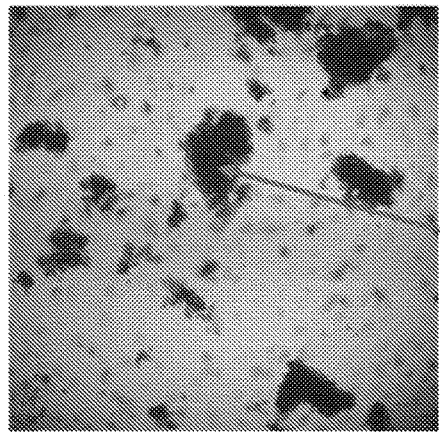
FIGS. 18A-18H. Microscopic validation of the bi-layered bead loading approach.
Figure 18B:
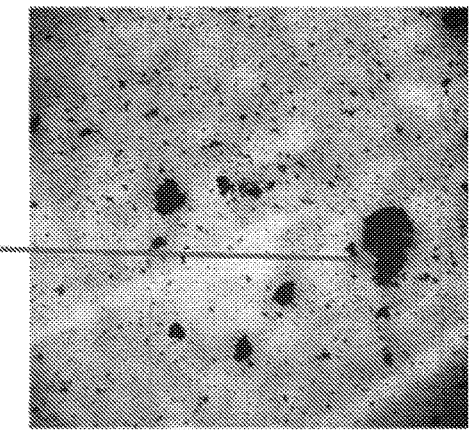
Figure 18C:
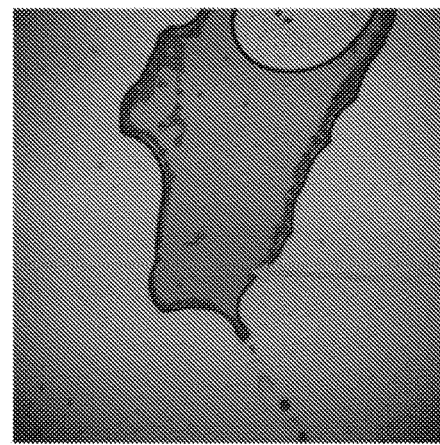
Figure 18D:
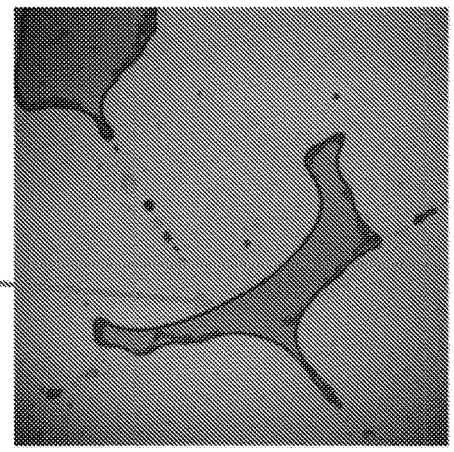
Figure 18E:
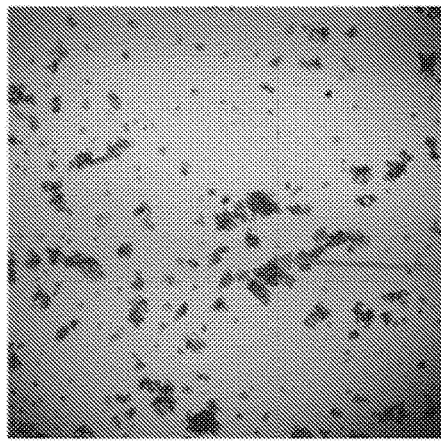
Figure 18F:
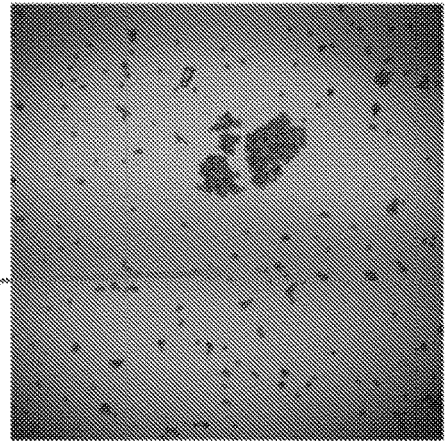
Figure 18G:
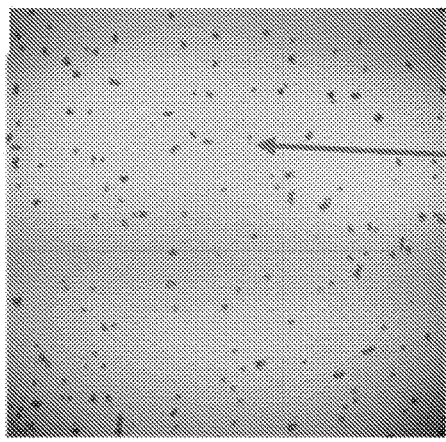
Figure 18H:
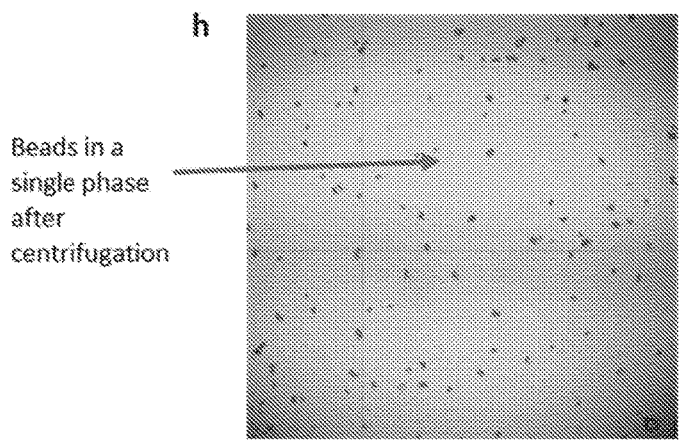

To validate this technique, a tube-based LAMP amplification reaction was carried out using this setup (FIGS. 16A-16C) using a mixture of mineral oil (other hydrocarbon based solvents such as hexane or toluene are also compatible) and Triton-X 100 as the carrier fluid. The beads are pulled to the bottom of the reaction either via centrifugation for polystyrene beads or via a strong magnet when using magnetic beads. LAMP amplification curves validating this technique and the microscopic validation of this technique are shown in FIGS. 17A-17B and FIGS. 18A-18H respectively.

Bead-Based Tri-Layered Approach:

The tri-layered approach utilizes a polar solvent, such as ethanol which can solubilize beads easily but is less dense than water and the immiscible middle layer (e.g. mineral oil) as the carrier fluid. The bottom-most layer of the tri-layer system is water. The middle layer is an immiscible liquid lighter than water with or without a surfactant (similar to the top layer in the bi-layer approach). The topmost layer is the lyophilized beads suspended in a mixture of surfactant and a polar solvent. The topmost layer must be immiscible and less dense than the middle layer. It is important to note that the stability of polymerase enzymes may be compromised in solvents such as ethanol.[11] When using solvents such as ethanol which have the required low density for this method, the enzymes need to be protected from such solvents due to the solvents' denaturing effects on proteins. The protection of enzymes in denaturing solvents such as ethanol is shown by forming nanoscale micellar structures surrounding the bead with lyophilized enzymes through the use of surfactants. In this method, the surfactant in water (0.1% Triton-X 100-water-based) was first added to the lyophilized beads to initially form micelles around the beads with lyophilized enzymes. The ethanol was added after this step. This sequence of steps showed positive amplification. On the contrary, when ethanol came into direct contact with the enzymes, without any prior presence of the surfactant, no positive reaction was observed. The protection of enzymes in the presence of denaturing solvents was tested to be effective for 4 hours (not tested for more than 4 hours).

Figure 19:
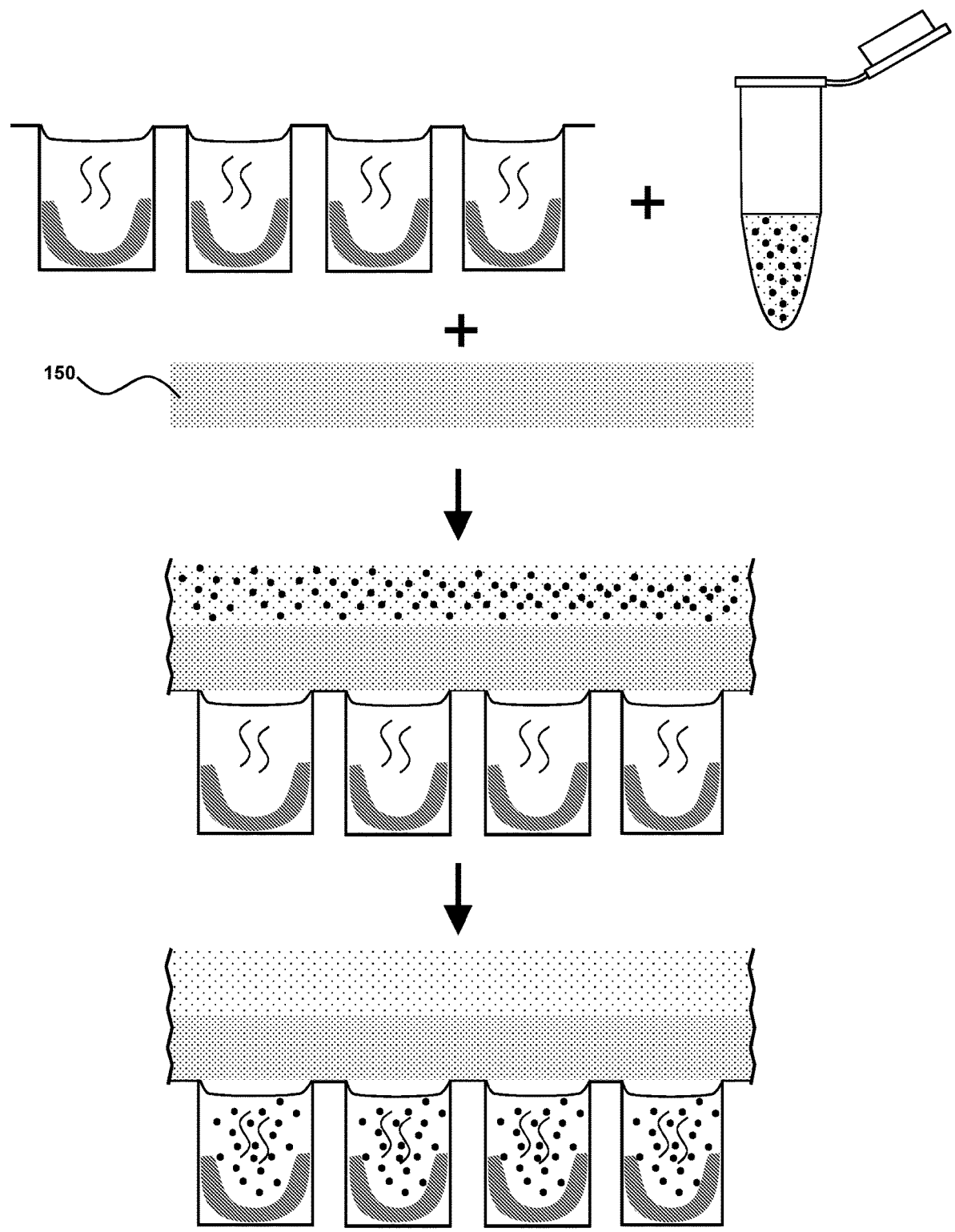
FIG. 19. On-chip process flow for the tri-layered bead loading technique.
Figure 20A:
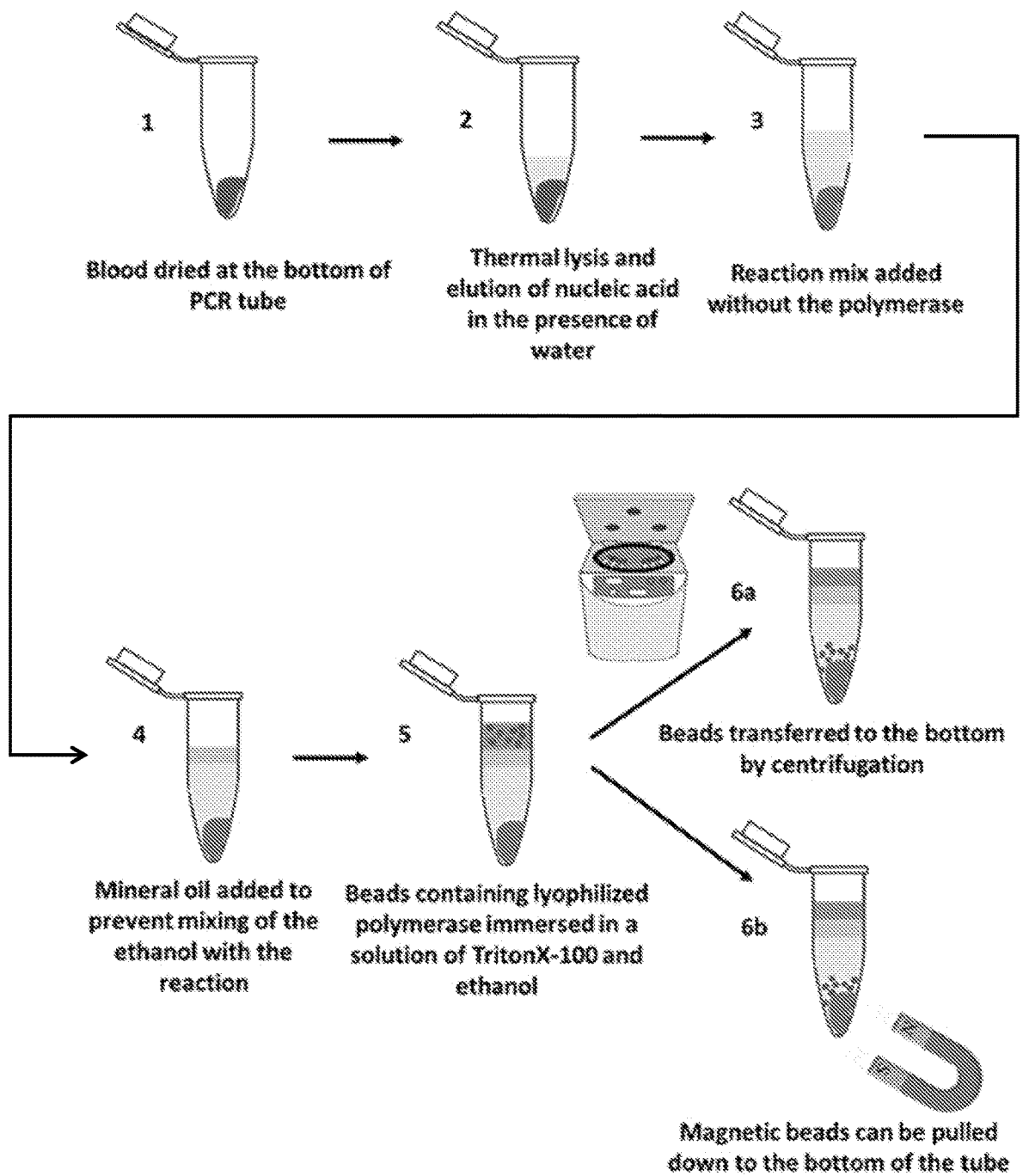
FIGS. 20A-20C. Tube based tri-layer bead loading approach.
Figure 20B:
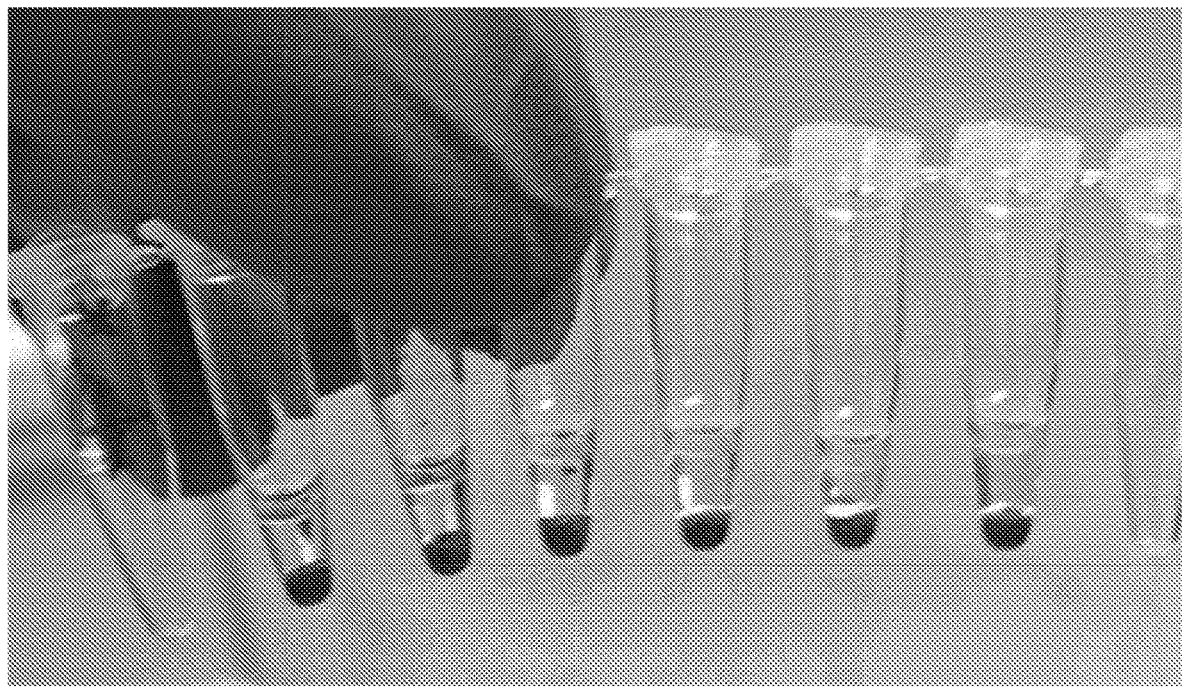
Figure 20C:
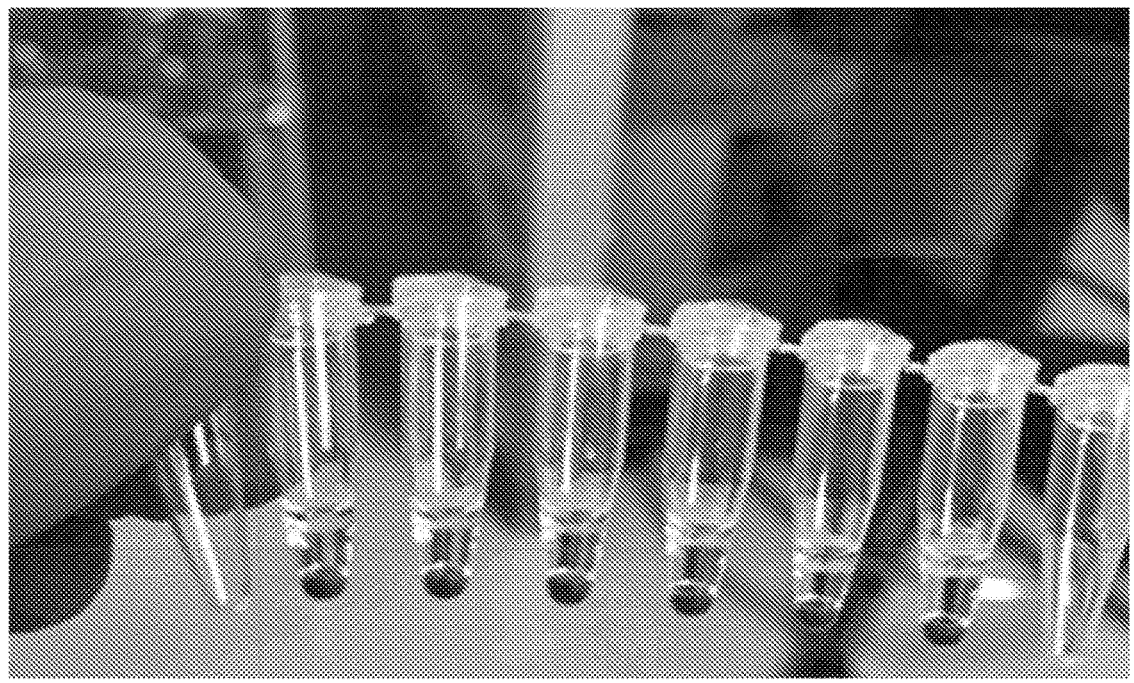
Figure 21A:
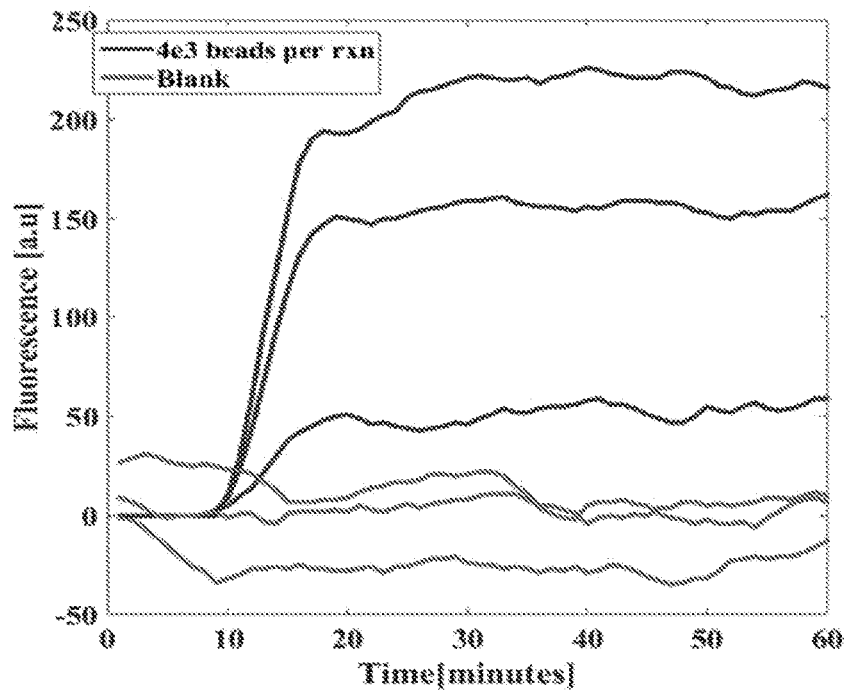
FIGS. 21A-21B. Tri-layered approach enzyme delivery LAMP reaction. LAMP amplification curves of the tri-layer approach carried out using (FIG. 21A) 4000 polystyrene beads per reaction, and (FIG. 21B) 4,000,000 magnetic beads per reaction.
Figure 21B:
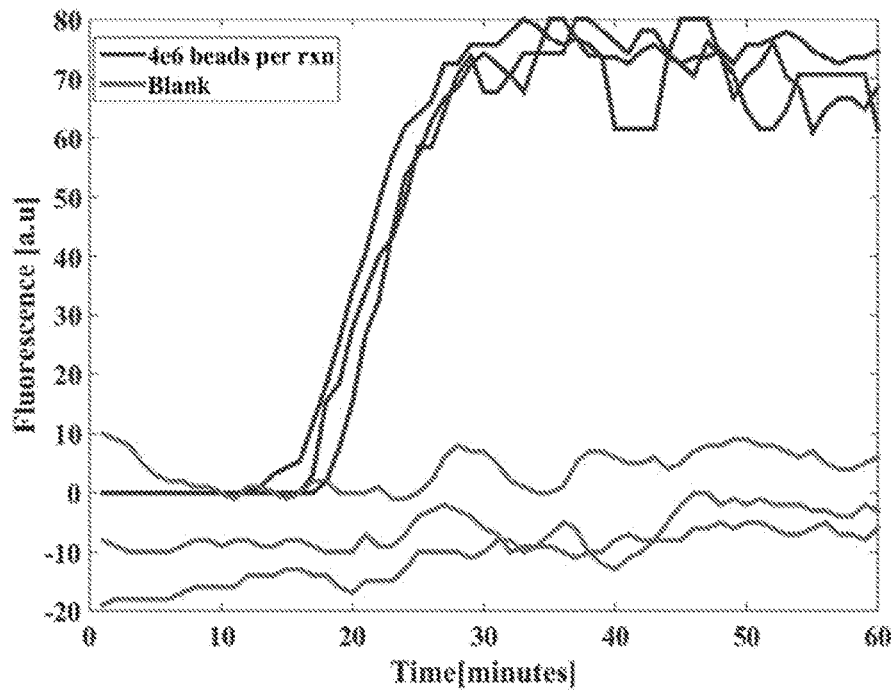
Figure 22A:
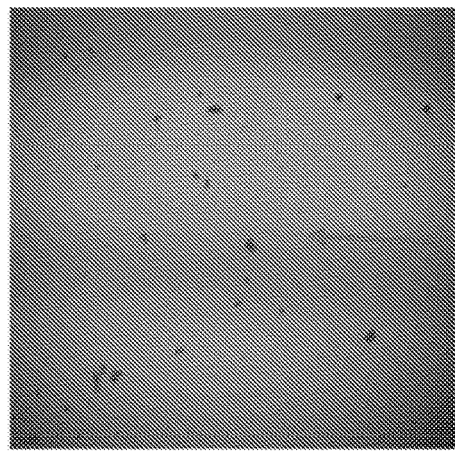
FIGS. 22A-22D. Microscopic validation of the tri-layered bead loading approach.
Figure 22B:
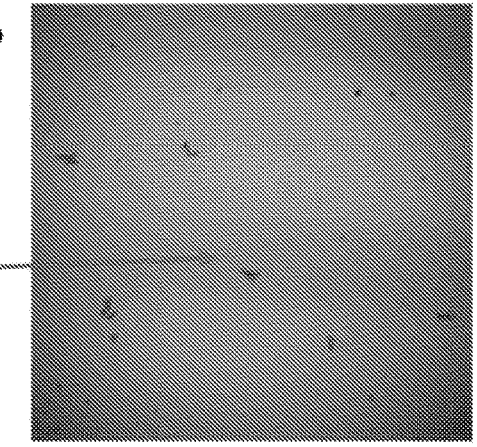
Figure 22C:
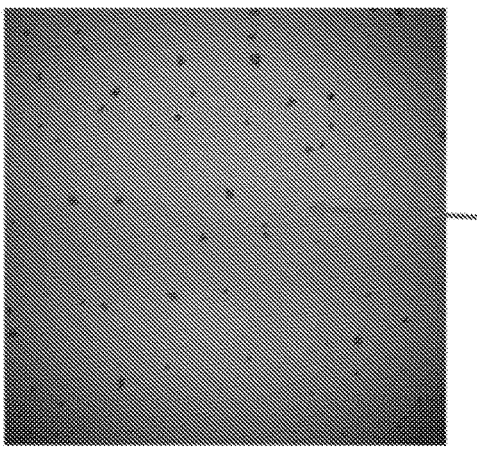
Figure 22D:
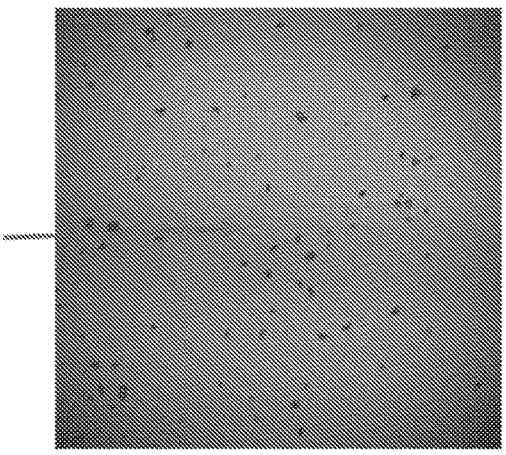

The on-chip schematic with the process flow (steps 1-4) for this bi-layer approach is illustrated in FIG. 19, where wells with dried blood, filled with buffer mixture and eluted nucleic acid are combined with lyophilized enzyme on beads suspended in a carrier fluid, such as ethanol, and a surfactant. Immiscible separating layer 150 forms an additional barrier layer, with the carrier fluid positioned on top of layer 150. Beads with desired reagents are pulled into the wells. This is referred to as a tri-layer, with two barrier layers and a liquid in the wells together forming three separate and well-defined liquids.

To validate this technique, we have carried out LAMP reactions where 1% Triton-X 100 followed by the addition 100% ethanol served as the carrier fluid for the beads. The beads were pulled down into the reaction mix in the same ways described in the bi-layered approach herein. The reaction schematics, LAMP amplification curves, and optical microscopy validation of the technique are shown in FIGS. 20A-20C, FIGS. 21A-21B and FIGS. 22A-22D, respectively.

Figure 23:
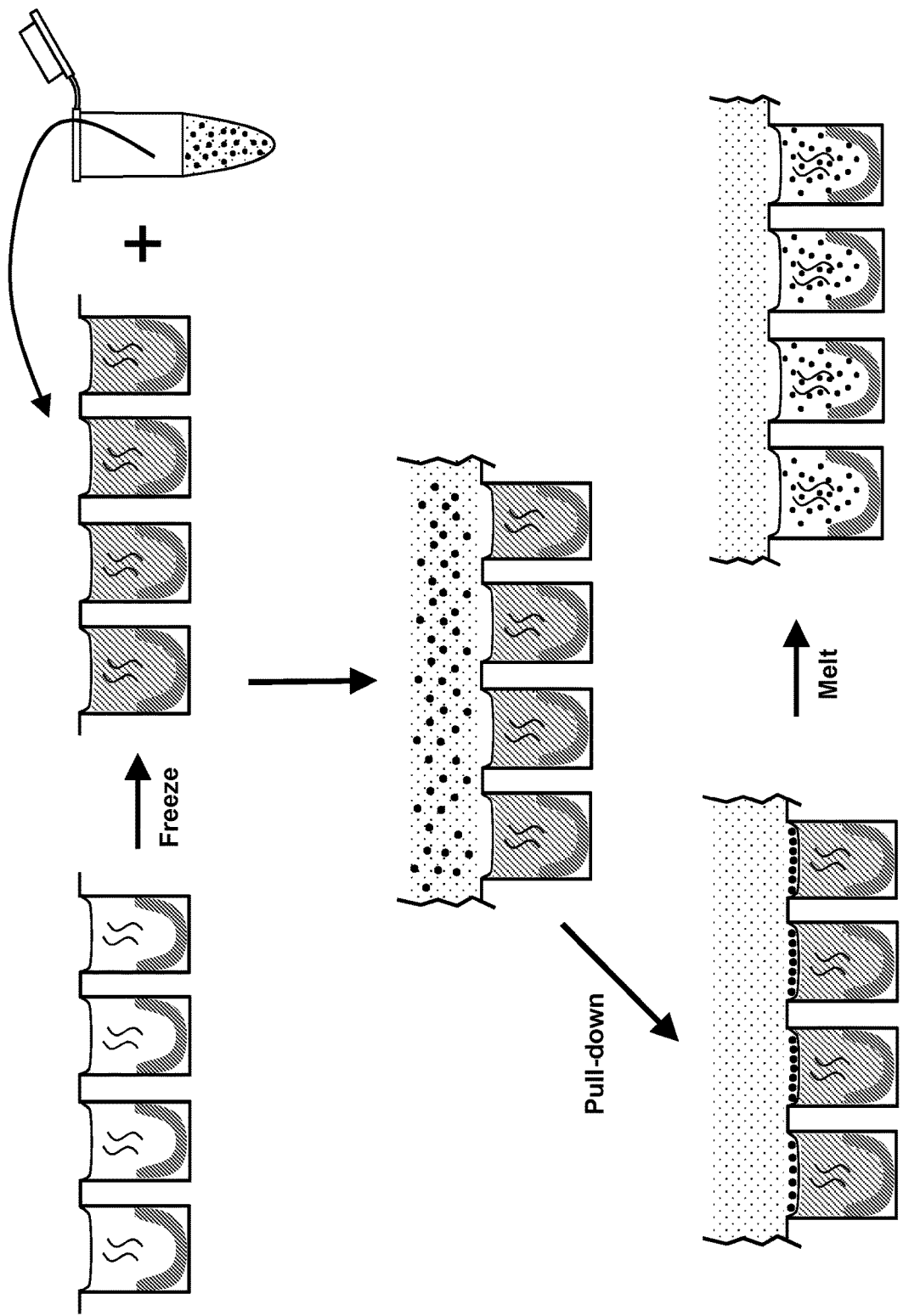
FIG. 23. On-chip process flow for bead loading at sub-zero temperature.

Loading at Sub-Zero Temperatures:

A miscible solvent can be used if the reaction mix is frozen post elution and the bead loading is done in sub-zero temperatures (degree C.). This prevents the molecular diffusion and mixing of the 2 miscible liquids (reaction mix and carrier fluid). The freezing temperature of the carrier fluid in such scenario should be below 0° C. and below the operating temperature of the process, so it remains as a liquid even when the reaction mix is frozen. Upon freezing of the reaction mix in wells at the appropriate temperature, a cold centrifugation or a magnetic pull-down (when using magnetic beads) will be carried out to pull down the beads to the interface of the frozen layer. The top layer, which will remain a liquid at the operating temperature, can then be removed by pipetting, and/or doing a series of cold washes, and/or letting it evaporate at sub-zero temperatures. After removal of the top layer, the bottom layer is thawed and the beads will be automatically incorporated into the reaction. The schematics for the on-chip process flow (steps 1-6) for this approach is illustrated in FIG. 23. The top panel illustrates freezing of the wells with buffer mixture and dried sample. Addition of the carrier fluid with beads results in a barrier layer on the top surface and beads pulled onto the top available frozen surface. Upon melting, the beads are pulled into the wells. The carrier fluid freezing point is lower than that of the water-based buffer or reaction mixture, to ensure the barrier layer is not frozen even if the liquid in the wells are frozen.

Micropillars Based Amplification Enzyme Delivery:

In this approach, needle-like micropillar structures are fabricated where polymerase enzymes will be lyophilized, more generally referred to as microstructures. Once the target nucleic acid has been eluted in the buffer mix on-chip in filled wells, the microneedles with the lyophilized polymerase are aligned and interfaced with the chip from the top.

Figure 24:
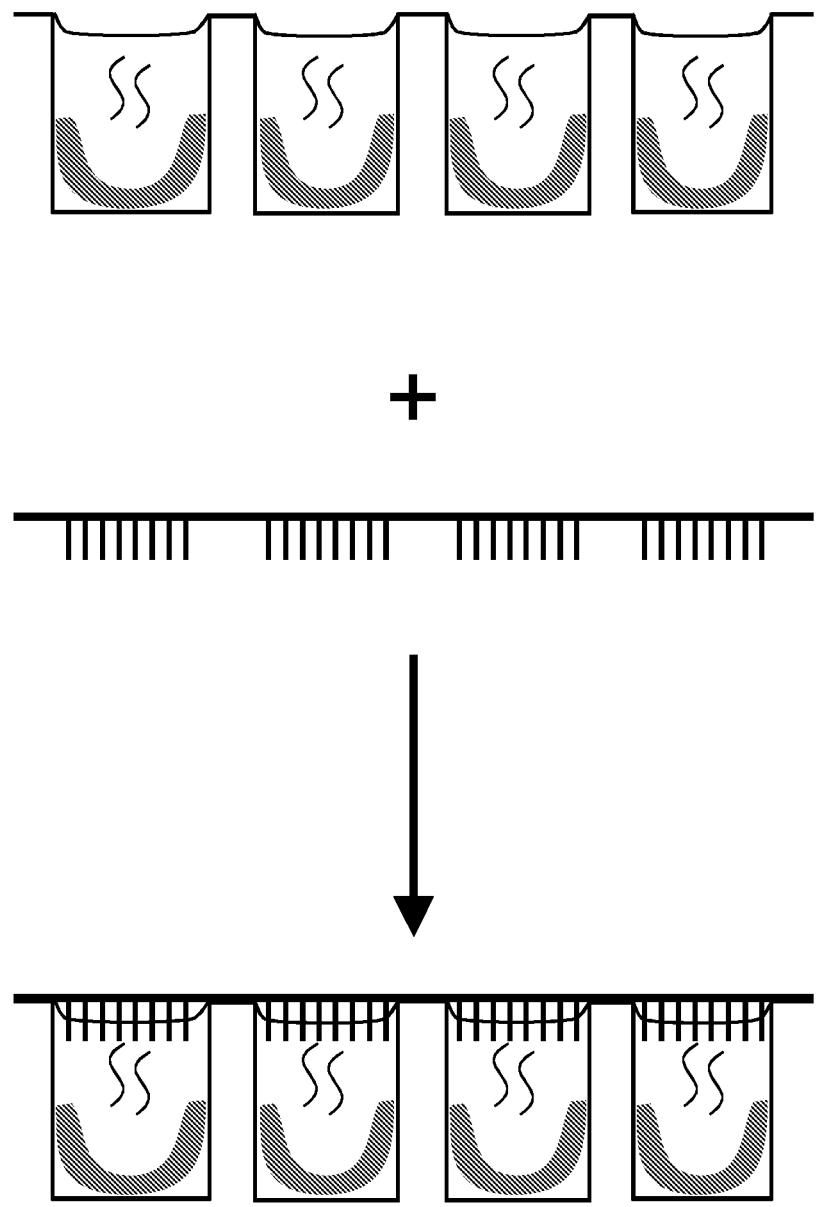
FIG. 24. On-chip process flow for microrelief or micropillars-based amplification enzyme delivery.

Each well can interact with multiple micro-needles. The lyophilized polymerase will hydrate and diffuse into the reaction once the needles come in contact with the buffer mix. The micro-needles can either be removed or clamped to the microfluidic chip to make one final device. The schematics for the process flow micropillars-based enzyme delivery are illustrated in FIG. 24. Briefly, wells with dried fluid sample, such as blood, are filled with a liquid phase, such as a buffer mixture. Nucleotide target (e.g., DNA/RNA) has been eluted from the sample (top panel). Micropillars with lyophilized enzymes (middle panel) are used to cover the wells (bottom panel). The micropillars introduce the enzyme into the reaction mixture while also forming a seal to prevent evaporation and unwanted cross-talk between wells.

5.c Bead Loading Through Emulsion:

In yet another version, an emulsion of polar solvent in another immiscible solvent is prepared where the beads will be in the compatible polar phase. Then this emulsion be used a carrier fluid for bead loading.

REFERENCES

1 A. Perner, A. Gordon, D. De Backer and G. Dimopoulos, *Intensive care*, 2016.
2 F. Wang, Q. Yang, J. A. Kase, J. Meng, L. M. Clotilde, A. Lin and B. Ge.
3 R. P. Peters, M. A. van Agtmael, S. A. Danner, P. H. Savelkoul and C. M. Vandenbroucke-Grauls, *Lancet Infect. Dis.*, 2004, 4, 751-760.
4 J. Vincent, S. Opal and J. Marshall, *Lancet* (London, 2013.
5 A. B. Martin, M. Hartman, J. Benson and A. Catlin, *Health Aff.*, 2016, 35, 150-160.
6 A. J. M. Loonen, M. P. Bos, B. van Meerbergen, S. Neerken, A. Catsburg, I. Dobbelaer, R. Penterman, G. Maertens, P. van de Wiel, P. Savelkoul and A. J. C. van den Brule, *PLoS One*, 2013, 8, 1-7.
7 N. Mancini, S. Carletti, N. Ghidoli and P. Cichero, *Clin. Microbiol.*, 2010.
8 M. S. Islam, A. Aryasomayajula and P. R. Selvaganapathy, 2017.
9 M. M. Packard, E. K. Wheeler, E. C. Alocilja and M. Shusteff, 2013, 105-116.
10 O. M. De Bruin and H. C. Birnboim, *BMC Microbiol.*, 2016, 1-10.
11 R. Chaloupkova and J. Damborsky, 2013.
12 A. Ganguli, A. Ornob, H. Yu, G. L. Damhorst, W. Chen and F. Sun, 2017, 1-13.

Example 3: Lyophilized/Dried Biomolecule Delivery to Micro/Nano-Well Arrays and Strategies for End-Point Multiplexed Detection of Nucleic Acid Targets To deliver material, including biomolecules, enzymes and the like, into a micro-well array in a multi-step process, the material can be lyophilized or dried on a fluid barrier, such as beads-on-a-wax paper, and pulled down into the wells using centrifugation or magnetic pull down. Since in a micro-well array, cross contamination between two adjacent wells is a challenge, loading the enzyme through beads on a wax paper allows simultaneous loading of a large array of wells (>1e6) in a single step requiring less than 1 minute. The fluid barrier may be a substrate with a hydrophobic coating, such as wax paper with its hydrophobic wax coating. Various barriers are compatible with the methdos and systems provided herein, so long as the barrier prevents any fluid exchange between adjacent wells during the process.

Figure 25:
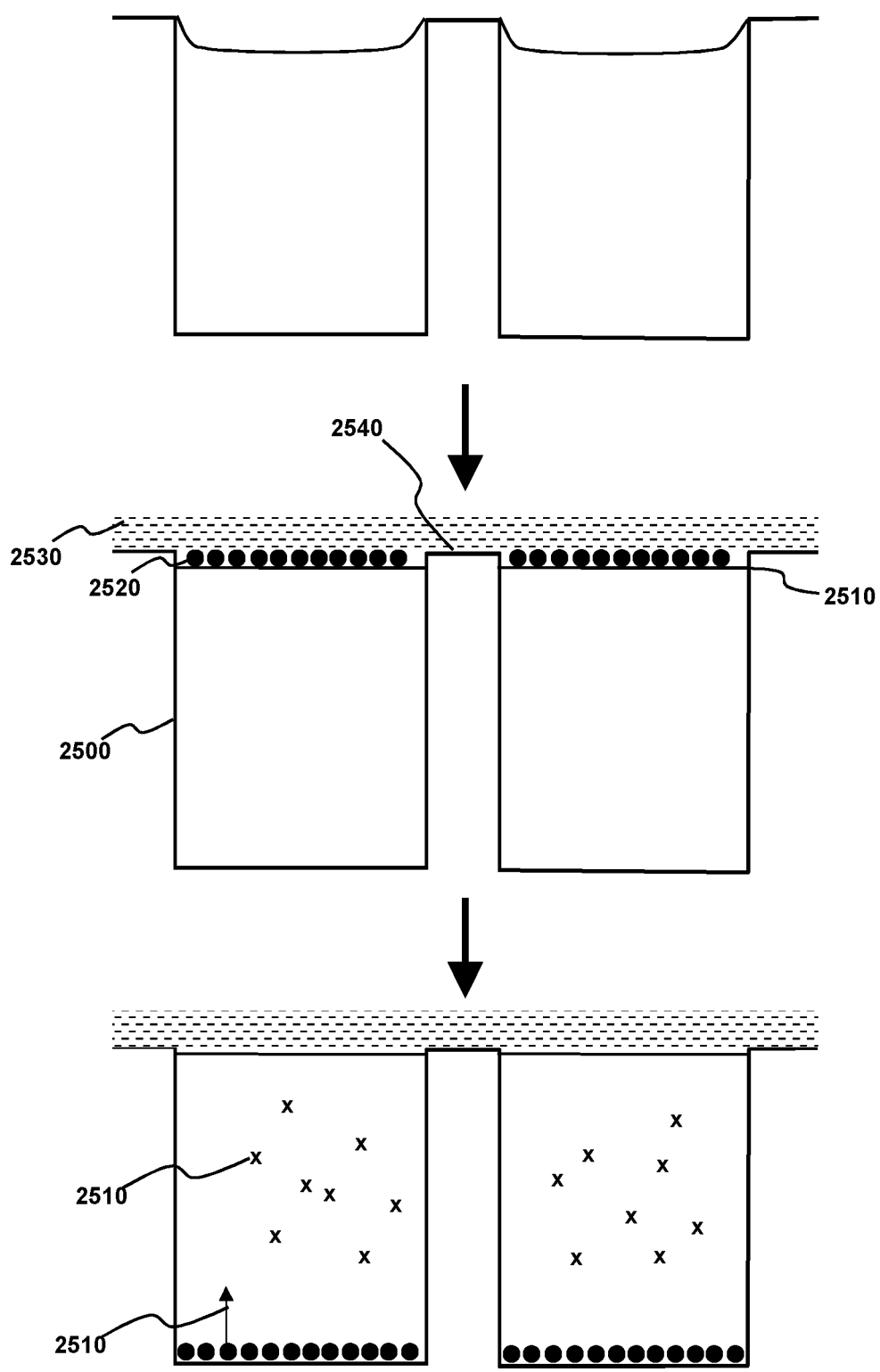
FIG. 25 schematically illustrates the introduction of a lyophilized or a dried material (e.g., a biomolecule) on a substrate for homogeneous delivery to individual wells of a microwell array. The left panel illustrates wells of a microwell array filled with reagent. The middle panel illustrates a hydrophobic substrate with dried biomolecules connected thereto over the wells. The biomolecules are pulled down into the wells, such as by a gravitation force, centrifugal force, or magnetic force.

A schematic illustration of the beads-on-barrier example is provided in FIG. 25. In this example, lyopholized/dried biomolecules are provided on beads 2520, with the beads connected to a hydrophobic substrate, so as to provide a platform for homogeneous delivery of material into a microwell array, including reliable delivery to individual microwells of the array. Reagents 2510 are provided in the microwells 2500. Material 2520, illustated as beads containing lyopholized/driead biomaterial, is connected to a hydrophobic substrate 2530 provided to the top 2501 of the microwells. The substrate 2530 functions to fluidically seal 2540 adjacent microwells, thereby preventing any unwanted cross-talk between adjacent microwells. Application of a release force 2550 releases the biomolecules (reagents) 2510 to the microwell. The biomolecules may be actively dispersed in the well by a mixing force and/or may passively disperse by diffusion.

Advantages of a process such as the one illustrated in FIG. 25 include: (1) Loading lyophilized enzymes/biomolecule while preventing any cross-talk between adjacent wells; (2) Sequential loading can allow multiple loading steps, each taking a relatively short time, such as less than a minute; (3) Uniform distribution of loading achieved as the distribution of beads on paper substrate is the same as the distribution transferred into the micro-well array. Of course, as desired, the beads may be distributed over the substate release surface as desired, including in a non-uniform or spatially vayring pattern, so that certain wells receive more biomolecule compared to other wells; and (4) No need for any other solvent/liquid for the loading process.

Example 4: Multiplexing Using Enzymes as End Point Detection Step for a High Number of Targets, Including CRISPR Proteins For digital amplification from dried whole blood in a micro-well array, we can use the CRISPR-cpf1 (or similar protein/biological molecules) for an end-point detection step of a high number of targets. The digital amplification chip isolates different targets in different wells allowing unique detection reactions in each well. Unique Crispr-cpf1 enzymes are designed for each nucleic acid target and then the target specific crispr-cpf1 enzymes are lyophilized on different sets of beads. The enzymes on beads are dispersed in an immiscible solution using surfactants and sequentially introduced into the digital amplification chip. Other methods of enzyme introduction into the microwell array are also compatible. After each step of introduction of the target specific crispr-cpf1 beads, the chip is measured for any positive detection. After the first round of bead introduction and detection, the next round begins with a different target-specific crispr-cpf1 beads. This can be repeated as many times as desired, such as for up to 100 targets, or even more than 100 targets, and each detection takes a very short time since the on-chip reaction volumes are very low (nanoliters to picoliters) and it will be easy for the cpf1 to quickly find its target in that volume (effective target concentration become high since volume becomes low after sample partitioning). A preamplification step to increase the copy numbers of the target can be performed to aid in the detection process. This technique is compatible with any sample digitization setup, with or without amplification. When combined with digital amplification it can be used to detect extremely low pathogen concentration (1 copy/ml or lower) for any number of applications including, for example, Sepsis diagnosis.

Figure 26:
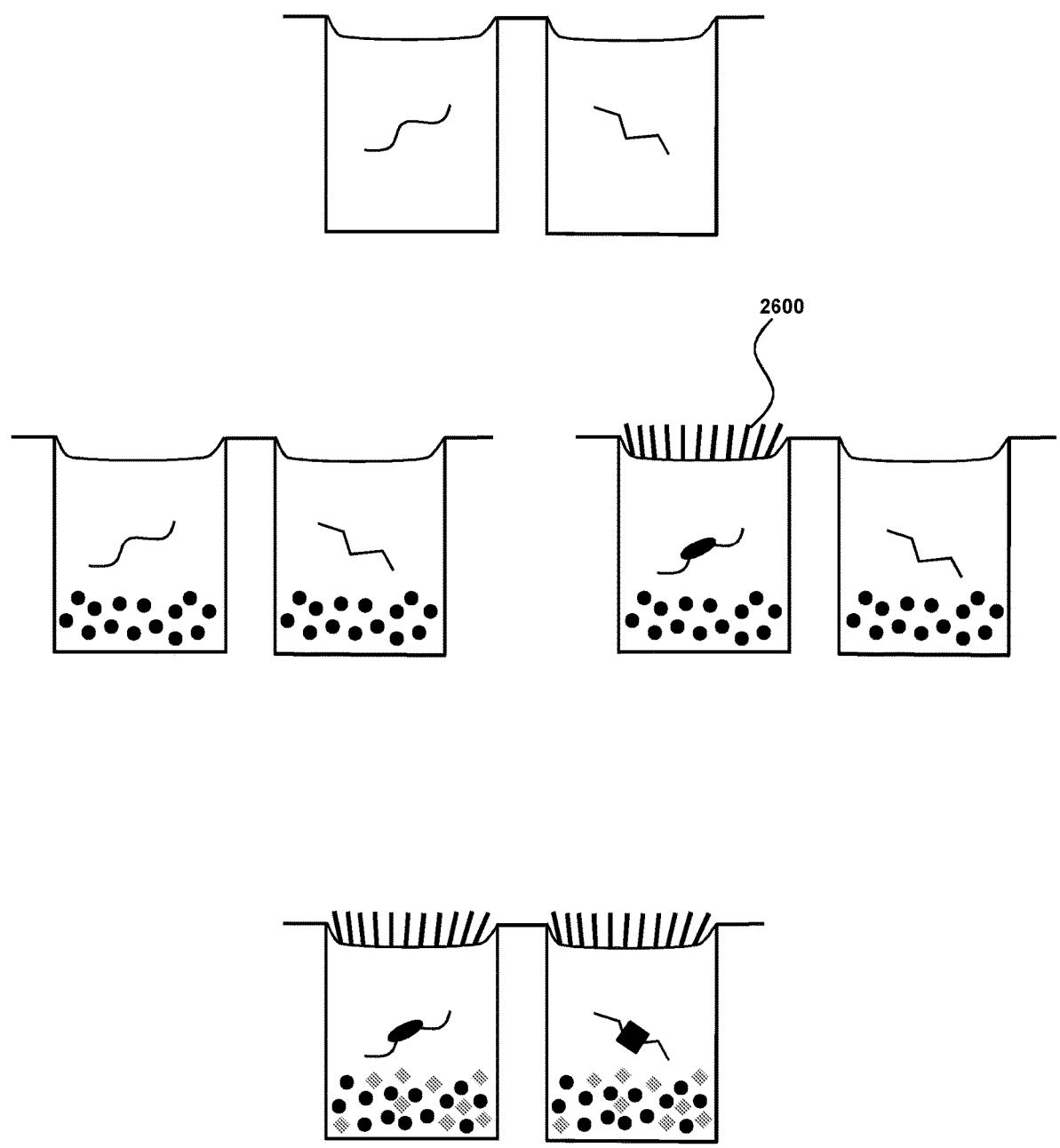
FIG. 26 is a schematic illustration of use of an enzyme, Crispr-cpf1, for multiplexed detection of nucleic acid targets with any of the digitized platforms provided herein. The left panel illustrates one unique target molecule per well, a configuration referred to herein as "sample partitioning". Beads with Crisper-cpf1 enzyme may be introduced, including by a process similar to that illustrated in FIG. 25, as shown in the middle panels. The introduction may be sequential, so that many different targets are analyzed by sequential analysis of a fluorescent signal, wherein a positive fluorescent signal from any well indicates the presence of the target corresponding to cpf1 delivered (right panel).

This example is schematically illustated in FIG. 26, where a single target is provided in each well by sample digestion-sample partitioning. The remaining steps show sequential delivery of target specific Crispr-cpf1 biomolecules in a microwell array, including by sequential delivery by the sequential process of FIG. 25. After each delivery of a Crispr-cpf1 enzyme system, the array is scanned for fluorescence and a positive fluorescent signal from any well indicates the presence of a target corresponding to the delivered cpf1. This sequential delivery and detection can be done for a large number of targets, such as up to 100 to 1000, 100 to 200, or greater than 100. Large target numbers are achieved by selecting the bead volume as about 3-4 orders of magnitude lower than the well volume. FIG. 26 shows Crispr-Cpf1 for multiplexed detection of nucleic acid targets in a digitized platform. Two wells are illustrated with different targets. Sample digitization-sample partitioning achieve a one target molecule per partition (e.g., well) (top panel). The remaining panels show sequential delivery of target specific crisp-cpf1 biomolecule in a microwell array. After each delivery, the array is optically scanned for fluorescence, and a positive flourescent signal 2600 from a well indicates the presence of a target corresponding to delivered cpf1. Sequential delivery and detection can be performed for a large number of targets (e.g., >150) by selecting a bead volume which is 3-4 orders of magnitude lower than the cell volume (bottom panel).

Advantages of this multiplexing example includes: (1) This technique allows combining digital amplification (PCR, LAMP, etc) in microwell array (or other formats) with end-point highly multiplexed and specific detection of the targets. In the digital format, the detection would also serve as quantitation since statistically only 1 or 0 copy of the target nucleic acid is present per well; (2) One cycle can be defined as loading of target-specific crispr-cpf1 followed by fluorescence detection/scanning of the array. N such cycles can be repeated, where N is up to 100 or even greater than 100. The wells lighting up (fluorescing) for a given cycle number will have the corresponding target molecule. (3) Crispr-cpf1, crispr-cas13 and similar proteins bind specifically to their target molecule through their "engineered guide RNA" and once bound, they start degrading/cutting any and all unbound nucleic acid molecules. Hence, a reporter nucleic acid molecule with a quenched fluorescence (quencher) can be used, whose fluorescence is retrieved once the molecule is cut by the cpf1 or similar enzyme. (4) A pre-amplification step will increase the copy numbers of the target per well and reduce the time to detection for each cycle/target. (5) No two targets can be in the same well as only 1 target would be detectable in such case and the other degraded by the active enzyme. Hence, there is a need for sample digitizing and partitioning system (droplet/well etc) to perform multiplexed end point detection. (6) Crispr-cpf1 can be replaced by other target specific hybridization strategies such as fluorescence, in situ hybridization, and the like.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, such as compositions, physical dimensions or temperatures, all individual members of the group and all combinations and sub-combinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, a volume range, a ratio range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of detecting one or more target analytes from a liquid sample, the method comprising the steps of:
    applying a liquid sample to a substrate, wherein the substrate has an array of wells;
    drying the liquid sample to generate a plurality of dried sample islands, with each sample island confined to a unique well;
    applying a liquid having a reagent suspended in a liquid buffer to each well, wherein the reagent is used for nucleic acid detection;
    eluting a nucleic acid from the dried sample islands with a liquid phase having the applied reagent;
    detecting a target nucleic acid if present in a dried sample island by a bi-phasic reaction, that occurs in both the dried sample islands and in the liquid having the reagent suspended in the liquid buffer, wherein the detecting is by electrical or optical detection;
thereby detecting the one or more target analytes from the liquid biological sample.

2. The method of claim 1, wherein the eluting comprises:
    forming microchannels and/or nanochannels in the dried sample islands to facilitate introduction of reagent-containing liquid into an interior portion of the dried sample islands;
    wherein eluted nucleic acid remains in the microchannels and/or nanochannels; diffuses from the microchannels and/or nanochannels to the liquid phase that is a supernatant to the dried sample islands; or both.

3. The method of claim 1, wherein the eluting step comprises one or more of thermally, chemically and enzymatically eluting the nucleic acid of the dried sample islands.

4. The method of claim 1, wherein the liquid sample is a biological sample.

5. The method of claim 4, wherein the liquid sample is minimally processed, including an unprocessed raw sample, without any purification steps.

6. The method of claim 1, wherein the applying the liquid having the reagent step is before or after the applying the liquid sample step.

7. The method of claim 1, wherein the detecting step comprises amplifying a target nucleic acid in the liquid phase.

8. The method of claim 1, wherein the bi-phasic reaction comprises the dried sample island and the reagent suspended in the liquid buffer, wherein the liquid buffer is positioned over the dried sample island in the well.

9. The method of claim 1, further comprising a step of forming high surface area structures in the plurality of dried sample islands and/or the liquid having the reagent positioned over the dried sample islands.

10. The method of claim 9, wherein the high surface area structures are formed by mixing gas with the liquid sample before or during the drying step.

11. The method of claim 9, wherein the high surface area structures comprise a reagent-connected bead suspended in the liquid having the reagent.

12. The method of claim 1, comprising a bead-based molecule delivery system, wherein the molecule is used in an amplifying or detecting step.

13. The method of claim 12, wherein said molecule is an enzyme.

14. The method of claim 12, wherein said bead-based molecule delivery system comprises a liquid bi-layer application, wherein:
    the liquid having the reagent suspended in the liquid buffer covers the dried sample islands;
    a carrier fluid having said bead-molecule suspended therein is disposed over said liquid having the reagent suspended in the liquid buffer; and
    the method further comprising a step of forcing said bead-molecule into the liquid having the reagent suspended in the liquid buffer.

15. The method of claim 12, wherein said bead-based molecule delivery system comprises a liquid tri-layer application, wherein:
    a buffer mixture covers the dried sample islands;
    an immiscible separating fluid that covers said buffer mixture;
    a carrier fluid having said bead-molecule suspended therein is disposed over said immiscible separating fluid, wherein the carrier fluid further comprises a surfactant that forms micelles around the bead-molecule to protect the molecule from denaturing; and
    the method further comprising a step of forcing said bead-molecule into the buffer mixture.

16. The method of claim 12, wherein said bead-based molecule delivery system comprises a liquid layer and frozen liquid layer application, wherein:
    the liquid having the reagent suspended in the liquid buffer covers the dried sample islands;
    a carrier fluid having said bead-molecule suspended therein, wherein said carrier fluid has a freezing point less than a freezing point of said liquid having the reagent suspended in the liquid buffer; and
    the method further comprising the steps of:
        freezing the liquid having the reagent suspended in the liquid buffer mixture by cooling the liquid having the reagent suspended in the liquid buffer mixture to a temperature that is below the liquid having the reagent suspended in the liquid buffer mixture freezing point and that is above the carrier fluid freezing point;

applying the carrier fluid on top of the frozen liquid having the reagent suspended in the liquid buffer mixture;

forcing the bead-molecule to the frozen liquid having the reagent suspended in the liquid buffer liquid carrier fluid interface;

thawing the frozen liquid having the reagent suspended in the liquid buffer; and forcing said bead-molecule into the liquid having the reagent suspended in the liquid buffer.

17. The method of claim 9, wherein the high surface area structures comprise a microrelief structure having a molecule connected thereto, the method further comprising the steps of:

aligning the microrelief structure with the array of wells;

inserting the microrelief structure into liquid having the reagent suspended in the liquid buffer that occupies the wells and covers the dried sample islands; and wherein the inserted microrelief structure introduces a reagent molecule to the liquid having the reagent suspended in the liquid buffer and prevents evaporation from the wells.

18. The method claim 1, having a sensitivity as high as 1 copy of a target nucleic acid per reaction well in a total liquid sample volume of between 1 mL and 10 mL.

19. The method of claim 1, used in an application selected from the group consisting of:

cancer molecular screening;

pathogen detection from body fluids, including for diagnosis of sepsis;

treatment efficacy assessment;

detection of pathogens from food and water samples;

detection of rare cells in biological sample, including circulating tumor cells; and detection of cell-free DNA from a body fluid sample.

20. The method of claim 1, wherein the liquid sample is selected from the group consisting of: whole blood; saliva; urine; sweat; throat swab; vaginal swab; sputum; drinkable fluid; environmental sample and edible food.

21. The method of claim 1, wherein the nucleic acid amplification comprises PCR or isothermal processes.

22. The method of claim 1, wherein the one or more target analytes comprise a nucleic acid sequence indicative of a pathogen or a disease state.

23. The method of claim 1, wherein the liquid buffer comprises:

an amplification enzyme and primers for nucleic acid amplification of a target analyte; and the amplification occurs in both the solid phase dried sample and in the liquid having the reagent suspended in the liquid buffer through simultaneous diffusion of enzymes and buffer components into the dried fluid sample and target nucleic acid into the liquid buffer.

24. The method of claim 1, wherein each well has a well volume selected from the range of 1 pL to 10 µL.

25. The method of claim 1, further comprising a step of thermally lysing biological cells contained in the liquid sample.

26. The method of claim 1, wherein the substrate is part of a microfluidic chip formed of silicon, glass or plastic.

27. The method of claim 1, wherein the detecting step comprises optically detecting fluorescent output of each of the wells.

28. The method of claim 1, wherein the detecting step comprises electrically detecting an electrical parameter in each of the wells.

29. The method of claim 28, wherein the electrically detecting is by measuring a change in pH in each well by ion sensitive field effect transistors (ISFET).

30. The method of claim 1, further comprising the steps of:

filling all wells with the fluid sample; and removing excess biological fluid sample that is not contained in said wells by introducing a gas over said wells at a pressure that is sufficient to remove excess fluid while fluid in said wells are maintained with said wells by capillary forces.

31. The method of claim 30, wherein said gas is an inert gas.

32. The method of claim 1, further comprising the step of:

connecting a dried material to a hydrophobic substrate release surface;

fluidically sealing the array of wells by providing the hydrophobic substrate onto a top portion of the array of wells, wherein the substrate release surface faces toward the array of wells; and releasing the dried material from the hydrophobic substrate to wells.

33. The method of claim 32, wherein the dried material comprises a lyophilized or dried biomolecule connected to a bead surface.

34. The method of claim 32, wherein the releasing step comprises centrifuging the fluidically sealed array of wells and hydrophobic substrate to release the dried material from the hydrophobic substrate to the array of wells.

35. The method of claim 32, wherein the dried materials comprises Crispr-cpf1.

36. The method of claim 35, wherein at least 100 different target analytes are identifiable by sequential addition of Crispr-cpf1 and corresponding sequential optical detection of a fluorescent signal generated by bound cpf1 to a target analyte.

37. A system for introducing a biomolecule to a plurality of wells in an array for target analyte detection, the system comprising:

a plate having a plurality of microwells, each microwell having:

a well surface;

a top portion that is physically accessible; and wherein adjacent microwells are separated by a separation surface and each microwell is configured to receive a liquid having a reagent suspended in a liquid buffer;

a hydrophobic substrate having a release surface, wherein the hydrophobic substrate comprises an immiscible carrier fluid that is lighter than water and a surfactant;

a biomolecule that is connected to beads, wherein the beads are dispersed in the immiscible carrier fluid;

wherein the hydrophobic substrate is configured to stay afloat on top of the liquid buffer in each of the microwells and connect to the microwell separation surface to fluidically seal the microwells to prevent fluid transmission between different microwells filled with a fluid and upon application of a force the beads are forced through the release surface and into the liquid in the microwells.

38. The system of claim 37, wherein the bead has a bead volume ($V_{bead}$) and the microwell has a microwell volume ($V_{well}$) and $V_{well}/V_{bead} > 1000$.

39. The system of claim 37, comprising a plurality of unique beads to form a plurality of unique hydrophobic substrates, wherein each hydrophobic substrate comprises a unique biomolecule that is different than any other hydrophobic substrate biomolecule, wherein the plurality of hydrophobic substrates provides multiplexed detection of target analytes.

40. The method of claim 4, wherein the liquid biological sample is unprocessed.

* * * * *

UNITED STATES PATENT AND TRADEMARK OFFICE
CERTIFICATE OF CORRECTION

| | | |
|---|---|---|
| PATENT NO. | : 11,732,293 B2 | Page 1 of 1 |
| APPLICATION NO. | : 16/649894 | |
| DATED | : August 22, 2023 | |
| INVENTOR(S) | : Bashir et al. | |

It is certified that error appears in the above-identified patent and that said Letters Patent is hereby corrected as shown below:

In the Claims

Column 32, Claim 16, Line 65, delete "mixture";

Column 32, Claim 16, Line 66, delete "mixture";

Column 33, Claim 16, Line 1, delete "mixture"; and

Column 33, Claim 16, Line 6, delete "mixture".

Signed and Sealed this
Seventh Day of November, 2023

Katherine Kelly Vidal
*Director of the United States Patent and Trademark Office*